US012629424B2

(12) United States Patent
Ji et al.

(10) Patent No.: US 12,629,424 B2
(45) Date of Patent: May 19, 2026

(54) TARGETING PLECKSTRIN-2 FOR TREATING CANCER

(71) Applicant: Northwestern University, Evanston, IL (US)

(72) Inventors: Peng Ji, Wilmette, IL (US); Gary E. Schiltz, Naperville, IL (US); Rama K. Mishra, Chicago, IL (US); Atul D. Jain, Chicago, IL (US)

(73) Assignee: Northwestern University, Evanston, IL (US)

( * ) Notice: Subject to any disclaimer, the term of this patent is extended or adjusted under 35 U.S.C. 154(b) by 1161 days.

(21) Appl. No.: 17/309,179

(22) PCT Filed: Nov. 1, 2019

(86) PCT No.: PCT/US2019/059462
§ 371 (c)(1),
(2) Date: May 3, 2021

(87) PCT Pub. No.: WO2020/092950
PCT Pub. Date: May 7, 2020

(65) Prior Publication Data

US 2022/0001018 A1 Jan. 6, 2022

Related U.S. Application Data

(60) Provisional application No. 62/754,121, filed on Nov. 1, 2018.

(51) Int. Cl.

| | |
|---|---|
| ***C07D 403/06*** | (2006.01) |
| ***A61K 47/54*** | (2017.01) |
| ***A61K 47/55*** | (2017.01) |
| ***A61P 35/00*** | (2006.01) |
| ***C07D 409/14*** | (2006.01) |

(52) U.S. Cl.
CPC .............. *A61K 47/55* (2017.08); *A61K 47/54* (2017.08); *A61P 35/00* (2018.01); *C07D 403/06* (2013.01); *C07D 409/14* (2013.01)

(58) Field of Classification Search
CPC ......... A61K 47/55; A61K 47/54; A61P 35/00; C07D 403/06; C07D 409/14; C07D 209/14; C07D 401/14; C07D 409/06
See application file for complete search history.

(56) References Cited

FOREIGN PATENT DOCUMENTS

WO 2008/115516 A2 9/2008

OTHER PUBLICATIONS

Wurz RP, Dellamaggiore K, Dou H, Javier N, Lo MC, McCarter JD, Mohl D, Sastri C, Lipford JR, Cee VJ. A "Click Chemistry Platform" for the Rapid Synthesis of Bispecific Molecules for Inducing Protein Degradation. J Med Chem. Jan. 25, 2018;61(2):453-461. (Year: 2018).*

Robinson, E., Leung, E., Matuszek, A. M., Krogsgaard-Larsen, N., Furkert, D. P., Brimble, M. A., Richardson, A., & Reynisson, J. (2015). Virtual screening for novel Atg5-Atg16 complex inhibitors for autophagy modulation. MedChemComm, 6(1), 239-246. (Year: 2015).*

STN (Year: 2024).*

STN_Applicant (Year: 2020).*

Ali et al. Input of Isosteric and Bioisosteric Approach in Drug Design., vol. 36, No. 1, 2014 (Year: 2014).*

Tomassoli, I., & Gündisch, D. (2015). The twin drug approach for novel nicotinic acetylcholine receptor ligands. Bioorganic & Medicinal Chemistry, 23(15), 4375-4389. (Year: 2015).*

Obach, R. S., LaChapelle, E. A., Brodney, M. A., Vanase-Frawley, M., Kauffman, G. W., & Sawant-Basak, A. (2016). Strategies toward optimization of the metabolism of a series of serotonin-4 partial agonists: investigation of azetidines as piperidine isosteres. Xenobiotica, 46(12), 1112-1121. (Year: 2016).*

STN search database (Year: 2025).*

PubChem CID 43912289 (Year: 2009).*

CAS Abstract of RN 950252-76-3 (Year: 2007).*

CAS Abstract of RN 950252-76-3 (Oct. 11, 2007) (Year: 2007).*

Registry STN on the Web, Database CA, RN823837-87-2, Jan. 2, 2007.

Zhao, Baobing, et al. "Pleckstrin-2 Plays an Essential Role in the Pathogenesis of JAK2V617F-Induced Myeloproliferative Neoplasms." Blood (2016) 128(22):798-798.

Levine RL, et al. Activating mutation in the tyrosine kinase JAK2 in polycythemia vera, essential thrombocythemia, and myeloid metaplasia with myelofibrosis. Cancer Cell. 2005;7(4):387-397.

Liepina I, Czaplewski C, Janmey P, Liwo A. Molecular dynamics study of a gelsolin-derived peptide binding to a lipid bilayer containing phosphatidylinositol 4,5-bisphosphate. Biopolymers. 2003;71(1):49-70. Epub Apr. 25, 2003 doi: 10.1002/bip.10375. PubMed PMID: 12712500.

(Continued)

*Primary Examiner* — James H Alstrum-Acevedo
*Assistant Examiner* — Pierre Paul Eleniste
(74) *Attorney, Agent, or Firm* — Quarles & Brady LLP

(57) ABSTRACT

Disclosed herein are compounds, compositions, and methods for treating cell proliferative diseases and disorders based on present inventors discovery that Pleckstrin-2 (Plek2) can be targeted to treat cell proliferative diseases and disorders. The compositions and methods disclosed herein include or utilize the disclosed compounds as therapeutic agents which inhibit the biological activity or expression of Pleckstrin-2 (Plek2) and collectively may be referred to as "Plek2 inhibitors." Disclosed are small molecule inhibitors of Plek2 biological activity. The compositions and method may be utilized for treating cell proliferative diseases and disorders that are characterized by elevated levels of Plek2 expression and/or by activation of the phosphatidylinositide 3-kinase (PI3K)/Akt pathway. Cell proliferative diseases and disorders that may be treated using the disclosed compositions and methods may include, but not limited to, myeloproliferative neoplasms (MPNs) such as Philadelphia (Ph)-negative MPNs, and cancers such as acute myeloid leukemia (AML) and cancers characterized by solid tumors.

14 Claims, 22 Drawing Sheets

(56) References Cited

OTHER PUBLICATIONS

Liu J, et al. Quantitative analysis of murine terminal erythroid differentiation in vivo: novel method to study normal and disordered erythropoiesis. Blood. 2013; 121(8):e43-e49.
Lonsdale R, Ward RA. Structure-based design of targeted covalent inhibitors. Chemical Society reviews. 2018;47(11):3816-30. Epub Apr. 6, 2018. doi: 10.1039/c7cs00220c. PubMed PMID: 29620097.
Lu M, et al. Treatment with the Bcl-XL inhibitor ABT-737 in combination with interferon a specifically targets JAK2V617F-positive polycythemia vera hematopoietic progenitor cells. Blood. 2010; 116(20):4284-4287.
Ma AD, Abrams CS. Pleckstrin induces cytoskeletal reorganization via a Rac-dependent pathway. J Biol Chem. 1999;274(40):28730-5. Epub Sep. 25, 1999. PubMed PMID: 10497244.
Marubayashi S, et al. HSP90 is a therapeutic target in JAK2-dependent myeloproliferative neoplasms in mice and humans. J Clin Invest. 2010;120(10):3578-3593.
McLaughlin S, Murray D. Plasma membrane phosphoinositide organization by protein electrostatics. Nature. 2005;438(7068):605-11. Epub Dec. 2, 2005. doi: 10.1038/nature04398. PubMed PMID: 16319880.
McLoman et al., “JAK2 V617F: A Single Mutation in the Myeloproliferative Group of Disorders,” Ulster Med. J., May 2006; 75(2):112-119.
Mishra RK, Wei C, Hresko RC, Bajpai R, Heitmeier M, Matulis SM, Nooka AK, Rosen ST, Hruz PW, Schiltz GE, Shanmugam M. In Silico Modeling-based Identification of Glucose Transporter 4 (GLUT4)-selective Inhibitors for Cancer Therapy. J Biol Chem. 2015;290(23):14441-53. Epub Apr. 8, 2015. doi: 10.1074/jbc.M114.628826. PubMed PMID: 25847249; PMCID: PMC4505511.
Mullally A, et al. Physiological Jak2V617F expression causes a lethal myeloproliferative neoplasm with differential effects on hematopoietic stem and progenitor cells. Cancer Cell. 2010;17(6):584-596.
Nangalia J, Grinfeld J, Green AR. Pathogenesis of myeloproliferative disorders. Annu Rev Pathol. 2016;11:101-126.
Neklesa et al., “Targeted protein degradation by PROTACs,” Pharma & Ther., vol. 174, Jun. 2017, pp. 138-144.
Nelson EA, et al. The STAT5 inhibitor pimozide decreases survival of chronic myelogenous leukemia cells resistant to kinase inhibitors. Blood. 2011;117(12):3421-3429.
Pardanani A, et al. Safety and efficacy of CYT387, a JAK1 and JAK2 inhibitor, in myelofibrosis. Leukemia. 2013;27(6):1322-1327.
Pasquier F, Cabagnols X, Secardin L, Plo I, Vainchenker W. Myeloproliferative neoplasms: JAK2 signaling pathway as a central target for therapy. Clin Lymphoma Myeloma Leuk. 2014;14 Suppl:S23-S35.
Passamonti F, Maffioli M. The role of JAK2 inhibitors in MPNs 7 years after approval. Blood. 2018;131(22):2426-35. Epub Apr. 14, 2018. doi: 10.1182/blood-2018-01-791491. PubMed PMID: 29650801.
Pellagatti A, et al. Gene expression profiling in polycythemia vera using cDNA microarray technology. Cancer Res. 2003;63(14):3940-3944.
Pikman Y, Lee BH, Mercher T, McDowell E, Ebert BL, Gozo M, Cuker A, Wernig G, Moore S, Galinsky I, DeAngelo DJ, Clark JJ, Lee SJ, Golub TR, Wadleigh M, Gilliland DG, Levine RL. MPLW515L is a novel somatic activating mutation in myelofibrosis with myeloid metaplasia. PLoS Med. 2006;3(7):e270. Epub Jul. 13, 2006. doi: 10.1371/journal.pmed.0030270. PubMed PMID: 16834459; PMCID: PMC1502153.
Porpaczy E, Tripolt S, Hoelbl-Kovacic A, Gisslinger B, Bago-Horvath Z, Casanova-Hevia E, Clappier E, Decker T, Fajmann S, Fux DA, Greiner G, Gueltekin S, Heller G, Herkner H, Hoermann G, Kiladjian JJ, Kolbe T, Kornauth C, Krauth MT, Kralovics R, Muellauer L, Mueller M, Prchal-Murphy M, Putz EM, Raffoux E, Schiefer AI, Schmetterer K, Schneckenleithner C, Simonitsch-Klupp I, Skrabs C, Sperr WR, Staber PB, Strobl B, Valent P, Jaeger U, Gisslinger H, Sexl V. Aggressive B-cell lymphomas in patients with myelofibrosis receiving JAK1/2 inhibitor therapy. Blood. 2018.
Puigdecanet E, et al. Gene expression profiling distinguishes JAK2V617F-negative from JAK2V617F-positive patients in essential thrombocythemia. Leukemia. 2008;22(7):1368-1376.
Rambaldi A, et al. A pilot study of the histonedeacetylase inhibitor Givinostat in patients with JAK2V617F positive chronic myeloproliferative neoplasms. Br J Haematol. 2010;150(4):446-455.
Rampal R, et al. Integrated genomic analysis illustrates the central role of JAK-STAT pathway activation in myeloproliferative neoplasm pathogenesis. Blood. 2014;123(22):e123-e133.
Schulz-Gasch T, Stahl M. Binding site characteristics in structure-based virtual screening: evaluation of current docking tools. J Mol Model. 2003;9(1):47-57. Epub Mar 15, 2003. doi: 10.1007/s00894-002-0112-y. PubMed PMID: 12638011.
Sheetz MP. Cell control by membrane-cytoskeleton adhesion. Nat Rev Mol Cell Biol. 2001;2(5):392-6. Epub May 2, 2001. doi: 10.1038/35073095. PubMed PMID: 11331914.
Sherman W, Day T, Jacobson MP, Friesner RA, Farid R. Novel procedure for modeling ligand/receptor induced fit effects. J Med Chem. 2006;49(2):534-53. Epub Jan. 20, 2006. doi: 10.1021/jm050540c. PubMed PMID: 16420040.
Sonbol MB, Firwana B, Zarzour A, Morad M, Rana V, Tiu RV. Comprehensive review of JAK inhibitors in myeloproliferative neoplasms. Ther Adv Hematol. 2013;4(1):15-35.
Tefferi A, Pardanani A. Myeloproliferative neoplasms: a contemporary review. JAMA Oncol. 2015;1(1):97-105.
Tenedini E, et al. Gene expression profiling of normal and malignant CD34-derived megakaryocytic cells. Blood. 2004;104(10):3126-3135.
Vannucchi AM, Harrison CN. Emerging treatments for classical myeloproliferative neoplasms. Blood. 2017;129 (6):693-703. Epub Dec. 29, 2016. doi: 10.1182/blood-2016-10-695965. PubMed PMID: 28028027.
Verstovsek S, et al. Efficacy, safety, and survival with ruxolitinib in patients with myelofibrosis: results of a median 3-year follow-up of Comfort-I. Haematologica. 2015;100(4):479-488.
Waibel M, et al. Combined targeting of JAK2 and Bcl-2/Bcl-xL to cure mutant JAK2-driven malignancies and overcome acquired resistance to JAK2 inhibitors. Cell Rep. 2013;51047-1059.
Wang Y, Chen X, Lian L, Tang T, Stalker TJ, Sasaki T, Kanaho Y, Brass LF, Choi JK, Hartwig JH, Abrams CS. Loss of PIP5KIbeta demonstrates that PIP5KI isoform-specific PIP2 synthesis is required for IP3 formation. Proc Natl Acad Sci USA. 2008;105(37):14064-9. Epub Sep. 6, 2008. doi: 10.1073/pnas.0804139105. PubMed PMID: 18772378; PMCID: PMC2544579.
Wang Y, Litvinov RI, Chen X, Bach TL, Lian L, Petrich BG, Monkley SJ, Kanaho Y, Critchley DR, Sasaki T, Birnbaum MJ, Weisel JW, Hartwig J, Abrams CS. Loss of PIP5KIgamma, unlike other PIP5KI isoforms, impairs the integrity of the membrane cytoskeleton in murine megakaryocytes. J Clin Invest. 2008; 118(2):812-9. Epub Jan. 12, 2008. doi: 10.1172/JCI34239. PubMed PMID: 18188447; PMCID: PMC2176194.
Wen QJ, Yang Q, Goldenson B, Malinge S, Lasho T, Schneider RK, Breyfogle LJ, Schultz R, Gilles L, Koppikar P, Abdel-Wahab O, Pardanani A, Stein B, Gurbuxani S, Mullally A, Levine RL, Tefferi A, Crispino JD. Targeting megakaryocytic-induced fibrosis in myeloproliferative neoplasms by AURKA inhibition. Nat Med. 2015;21(12):1473-80. Epub Nov. 17, 2015. doi: 10.1038/nm.3995. PubMed PMID: 26569382; PMCID: PMC4674320.
Wernig G, et al. The Jak2V617F oncogene associated with myeloproliferative diseases requires a functional FERM domain for transformation and for expression of the Myc and Pim protooncogenes. Blood. 2008; 111(7):3751-3759.
Witthuhn BA, et al. JAK2 associates with the erythropoietin receptor and is tyrosine phosphorylated and activated following stimulation with erythropoietin. Cell. 1993;74(2):227-236.
Yilmaz OH, Valdez R, Theisen BK, Guo W, Ferguson DO, Wu H, Morrison SJ. Pten dependence distinguishes haematopoietic stem cells from leukaemia-initiating cells. Nature. 2006;441(7092):475-82. Epub Apr. 7, 2006. doi: 10.1038/nature04703. PubMed PMID: 16598206.
Yu JW, Mendrola JM, Audhya A, Singh S, Keleti D, DeWald DB, Murray D, Emr SD, Lemmon MA. Genome-wide analysis of

(56) References Cited

OTHER PUBLICATIONS membrane targeting by S. cerevisiae pleckstrin homology domains. Mol Cell. 2004;13(5):677-88. Epub Mar. 17, 2004. PubMed PMID: 15023338.
Zhao B, et al. Targeted shRNA screening identified critical roles of pleckstrin-2 in erythropoiesis. Haematologica. 2014;99(7):1157-1167.
Zhou LP, Yang LH, Tilton S, Wang JL. Development of a high throughput equilibrium solubility assay using miniaturized shake-flask method in early drug discovery. J Pharm Sci-US. 2007;96(11):3052-71. doi: Doi 10.1002/ Jps.20913. PubMed PMID: WOS:000250618700018.
Zhao, B. et al. Loss of pleckstrin-2 reverts lethality and vascular occlusions in JAK2V617F-positive myeloproliferative neoplasms. J Clin Invest. 2018;128(1): 125-140.
International Search Report and Written Opinion issued in corresponding PCT Application No. PCT/US2019/059462, mailed Feb. 6, 2020.
Bartalucci N, Guglielmelli P, Vannucchi AM. Rationale for targeting the PI3K/Akt/mTOR pathway in myeloproliferative neoplasms. Clin Lymphoma Myeloma Leuk. 2013;13 Suppl 2:S307-9. Epub Dec. 7, 2013. doi: 10.1016/j.clml.2013.07.011. PubMed PMID: 24290217.
Robinson, E. et al. Virtual screening for novel Atg5 complex inhibitors for autophagy modulation. Med. Chem. Comm., 2014, 6(1), pp. 239-246.
Registry STN on the Web, Database CA, RN1185336-23-5, Sep. 17, 2009.
Registry STN on the Web, Database CA, RN1033200-86-0; 1033200-24-6; 1033198-49-0; 1033197-41-9, Sep. 7, 2008.
Registry STN on the Web, Database CA, RN950253-57-3; 950252-80-9; 950252-76-3; 950248-05-2; 950247-94-6; 950243-65-9; 950243-23-9; 950240-19-4; 950240-00-3; 950239-88-0, Nov. 10, 2007.
Registry STN on the Web, Database CA, RN942027-45-4, Oct. 7, 2007.
Registry STN on the Web, Database CA, RN923243-27-0; 923221-18-5; 923120-82-5; 923120-80-3, Feb. 26, 2007.
Abrams CS, Zhang J, Downes CP, Tang X, Zhao W, Rittenhouse SE. Phosphopleckstrin inhibits gbetagamma-activable platelet phosphatidylinositol-4,5-bisphosphate 3-kinase. J Biol Chem. 1996;271(41):25192-7. Epub Oct. 11, 1996. PubMed PMID: 8810277.
Adams BD, Baker R, Lopez JA, Spencer S. Myeloproliferative disorders and the hyperviscosity syndrome. Hematol Oncol Clin North Am. 2010;24(3):585-602.
Akada H, Yan D, Zou H, Fiering S, Hutchison RE, Mohi MG. Conditional expression of heterozygous or homozygous Jak2V617F from its endogenous promoter induces a polycythemia vera-like disease. Blood. 2010;115(17):3589-3597.
Araki M, Yang Y, Masubuchi N, Hironaka Y, Takei H, Morishita S, Mizukami Y, Kan S, Shirane S, Edahiro Y, Sunami Y, Ohsaka A, Komatsu N. Activation of the thrombopoietin receptor by mutant calreticulin in CALRmutant myeloproliferative neoplasms. Blood. 2016;127(10):1307-16. Epub Jan. 29, 2016. doi: 10.1182/blood-2015-09-671172. PubMed PMID: 26817954.
Armin J, Grant RT, Pels H, Reeve EB. The plasma, cell and blood volumes of albino rabbits as estimated by the dye (T 1824) and 32P marked cell methods. J Physiol (Lond). 1952;116(1):59-73.
Baby PM, et al. A novel method for blood volume estimation using trivalent chromium in rabbit models. Indian J Plast Surg. 2014;47(2):242-248.
Bach TL, et al. PI3K regulates pleckstrin-2 in T-cell cytoskeletal reorganization. Blood. 2007;109(3):1147-1155.
Barbui T, Finazzi G, Falanga A. Myeloproliferative neoplasms and thrombosis. Blood. 2013;122(13):2176-2184.
Bar-Natan M, Nelson EA, Walker SR, Kuang Y, Distel RJ, Frank DA. Dual inhibition of Jak2 and STAT5 enhances killing of myeloproliferative neoplasia cells. Leukemia. 2012;26(6):1407-1410.
Bartalucci N, et al. Co-targeting the PI3K/mTOR and JAK2 signalling pathways produces synergistic activity against myeloproliferative neoplasms. J Cell Mol Med. 2013;17(11):1385-1396.
Baxter EJ, et al. Acquired mutation of the tyrosine kinase JAK2 in human myeloproliferative disorders. Lancet. 2005;365(9464):1054-1061.
Berkofsky-Fessler W, et al. Transcriptional profiling of polycythemia vera identifies gene expression patterns both dependent and independent from the action of JAK2V617F. Clin Cancer Res. 2010;16(17):4339-4352.
Bondeson et al., "Lesson in PROTAC Design from Selective Degradation with a Promiscuous Warhead," Cell Chemical Biology, vol. 25, No. 1, p. 78-87, (2018).
Butler KV, Ma A, Yu W, Li F, Tempel W, Babault N, Pittella-Silva F, Shao J, Wang J, Luo M, Vedadi M, Brown PJ, Arrowsmith CH, Jin J. Structure-Based Design of a Covalent Inhibitor of the SET Domain-Containing Protein 8 (SETD8) Lysine Methyltransferase. J Med Chem. 2016;59(21):9881-9. Epub Nov. 3, 2016. doi: 10.1021/acs.jmedchem.6b01244. PubMed PMID: 27804297; PMCID: PMC5148670.
Caroni P. New EMBO members' review: actin cytoskeleton regulation through modulation of PI(4,5)P(2) rafts. EMBO J. 2001;20(16):4332-6. Epub Aug. 14, 2001. doi: 10.1093/emboj/20.16.4332. PubMed PMID: 11500359; PMCID: PMC125564.
Cervantes F, et al. Three-year efficacy, safety, and survival findings from COMFORT-II, a phase 3 study comparing ruxolitinib with best available therapy for myelofibrosis. Blood. 2013;122(25):4047-4053.
Chen E, et al. Distinct clinical phenotypes associated with JAK2V617F reflect differential STAT1 signaling. Cancer Cell. 2010;18(5):524-535.
Chen VB, Arendall WB, 3rd, Headd JJ, Keedy DA, Immormino RM, Kapral GJ, Murray LW, Richardson JS, Richardson DC. MolProbity: all-atom structure validation for macromolecular crystallography. Acta Crystallogr D Biol Crystallogr. 2010;66(Pt 1):12-21. Epub Jan. 9, 2010. doi: 10.1107/S0907444909042073. PubMed PMID: 20057044; PMCID: PMC2803126.
Choong ML, Pecquet C, Pendharkar V, Diaconu CC, Yong JW, Tai SJ, Wang SF, Defour JP, Sangthongpitag K, Villeval JL, Vainchenker W, Constantinescu SN, Lee MA. Combination treatment for myeloproliferative neoplasms using JAK and pan-class I PI3K inhibitors. J Cell Mol Med. 2013;17(11):1397-409. Epub Nov. 21, 2013. doi: 10.1111/jcmm.12156. PubMed PMID: 24251790; PMCID: PMC4117552.
Corces MR, et al. Lineage-specific and single-cell chromatin accessibility charts human hematopoiesis and leukemia evolution. Nat Genet. 2016;48(10):1193-1203.
Deschaies, "Prime Time for Protacs," Nature Chem. Biol., 11, 634-635 (2015).
Elf S, et al. Mutant calreticulin requires both its mutant C-terminus and the thrombopoietin receptor for oncogenic transformation. Cancer Discov. 2016;6(4):368-381.
Elliott MA, Tefferi A. Thrombosis and haemorrhage in polycythaemia vera and essential thrombocythaemia. Br J Haematol. 2005;128(3):275-290.
Falanga A, Marchetti M. Thrombosis in myeloproliferative neoplasms. Semin Thromb Hemost. 2014;40(3):348-358.
Fischer B, Luthy K, Paesmans J, De Koninck C, Maes I, Swerts J, Kuenen S, Uytterhoeven V, Verstreken P, Versees W. Skywalker—TBC1D24 has a lipid-binding pocket mutated in epilepsy and required for synaptic function. Nat Struct Mol Biol. 2016;23(11):965-73. Epub Nov. 1, 2016. doi: 10.1038/nsmb.3297. PubMed PMID: 27669036.
Fiskus W, Verstovsek S, Manshouri T, Smith JE, Peth K, Abhyankar S, McGuirk J, Bhalla KN. Dual PI3K/AKT/mTOR inhibitor BEZ235 synergistically enhances the activity of JAK2 inhibitor against cultured and primary human myeloproliferative neoplasm cells. Mol Cancer Ther. 2013; 12(5):577-88. Epub Mar. 1, 2013. doi: 10.1158/1535-7163. MCT-12-0862. PubMed PMID: 23445613.
Gautier EF, et al. The cell cycle regulator CDC25A is a target for JAK2V617F oncogene. Blood. 2012; 119(5):1190-1199.
GenBank as NCBI Reference Sequence: NP_057529.1.

(56) References Cited

OTHER PUBLICATIONS

Goerttler PS, et al. Gene expression profiling in polycythaemia vera: overexpression of transcription factor NF-E2. Br J Haematol. 2005;129(1):138-150.
Gu et al., "PROTACs: An Emerging Targeting Technique for Protein Degradation in Drug Discovery," BioEssays, 2018, 40 17000247, 1-11.
Guerini V, et al. The histone deacetylase inhibitor ITF2357 selectively targets cells bearing mutated JAK2(V617F). Leukemia. 2008;22(4):740-747.
Guglielmelli P, et al. Safety and efficacy of everolimus, a mTOR inhibitor, as single agent in a phase 1/2 study in patients with myelofibrosis. Blood. 2011;118(8):2069-2076.
Hamaguchi N, Ihara S, Ohdaira T, Nagano H, Iwamatsu A, Tachikawa H, Fukui Y. Pleckstrin-2 selectively interacts with phosphatidylinositol 3-kinase lipid products and regulates actin organization and cell spreading. Biochem Biophys Res Commun. 2007;361(2):270-5. Epub Jul. 31, 2007. doi: 10.1016/j.bbrc.2007.06.132. PubMed PMID: 17658464.
Harrison C, et al. JAK inhibition with ruxolitinib versus best available therapy for myelofibrosis. N Engl J Med. 2012;366 (9):787-798.
Hresko RC, Murata H, Mueckler M. Phosphoinositide-dependent kinase-2 is a distinct protein kinase enriched in a novel cytoskeletal fraction associated with adipocyte plasma membranes. J Biol Chem. 2003;278(24):21615-22. Epub Apr. 19, 2003. doi: 10.1074/jbc. M302937200. PubMed PMID: 12682057.
Hu MH, Bauman EM, Roll RL, Yeilding N, Abrams CS. Pleckstrin 2, a widely expressed paralog of pleckstrin involved in actin rearrangement. J Biol Chem. 1999;274(31):21515-21518.
Isakoff SJ, Cardozo T, Andreev J, Li Z, Ferguson KM, Abagyan R, Lemmon MA, Aronheim A, Skolnik EY. Identification and analysis of PH domain-containing targets of phosphatidylinositol 3-kinase using a novel in vivo assay in yeast. EMBO J. 1998;17(18):5374-87. Epub Sep. 16, 1998. doi: 10.1093/emboj/17.18.5374. PubMed PMID: 9736615; PMCID: PMC1170863.
James C, et al. A unique clonal JAK2 mutation leading to constitutive signalling causes polycythaemia vera. Nature. 2005;434(7037):1144-1148.
Ji P, Jayapal SR, Lodish HF. Enucleation of cultured mouse fetal erythroblasts requires Rac GTPases and mDia2. Nat Cell Biol. 2008;10(3):314-321.
Ji P, Murata-Hori M, Lodish HF. Formation of mammalian erythrocytes: chromatin condensation and enucleation. Trends Cell Biol. 2011;21(7):409-415.
Kleppe M, et al. JAK-STAT pathway activation in malignant and nonmalignant cells contributes to MPN pathogenesis and therapeutic response. Cancer Discov. 2015;5(3):316-331.
Koppikar P, Bhagwat N, Kilpivaara O, Manshouri T, Adli M, Hricik T, Liu F, Saunders LM, Mullally A, Abdel-Wahab O, Leung L, Weinstein A, Marubayashi S, Goel A, Gonen M, Estrov Z, Ebert BL, Chiosis G, Nimer SD, Bernstein BE, Verstovsek S, Levine RL. Heterodimeric JAK-STAT activation as a mechanism of persistence to JAK2 inhibitor therapy. Nature. 2012;489(7414):155-9. Epub Jul. 24, 2012. doi: 10.1038/nature11303. PubMed PMID: 22820254; PMCID: PMC3991463.
Kralovics R, et al. A gain-of-function mutation of JAK2 in myeloproliferative disorders. N Engl J Med. 2005;352(17):1779-1790.
Kralovics R, et al. Altered gene expression in myeloproliferative disorders correlates with activation of signaling by the V617F mutation of Jak2. Blood. 2005;106(10):3374-3376.
Kurokawa T, Takasuga S, Sakata S, Yamaguchi S, Horie S, Homma KJ, Sasaki T, Okamura Y. 3' Phosphatase activity toward phosphatidylinositol 3,4-bisphosphate [PI(3,4)P2] by voltage-sensing phosphatase (VSP). Proc Natl Acad Sci U S A. 2012; 109(25):10089-94. Epub May 31, 2012. doi: 10.1073/pnas. 1203799109. PubMed PMID: 22645351; PMCID: PMC3382541.
Lamrani L, et al. Hemostatic disorders in a JAK2V617F-driven mouse model of myeloproliferative neoplasm. Blood. 2014;124(7):1136-1145.
Laux T, Fukami K, Thelen M, Golub T, Frey D, Caroni P. GAP43, Marcks, and CAP23 modulate PI(4,5)P(2) at plasmalemmal rafts, and regulate cell cortex actin dynamics through a common mechanism. J Cell Biol. 2000; 149(7):1455-72. Epub Jun. 28, 2000. PubMed PMID: 10871285; PMCID: PMC2175130.
Lemmon MA, Ferguson KM, Abrams CS. Pleckstrin homology domains and the cytoskeleton. FEBS Lett. 2002;513(1):71-6. Epub Mar. 26, 2002. PubMed PMID: 11911883.
Lemmon MA, Ferguson KM, O'Brien R, Sigler PB, Schlessinger J. Specific and high-affinity binding of inositol phosphates to an isolated pleckstrin homology domain. Proc Natl Acad Sci U S A. 1995;92(23):10472-6. Epub Nov. 7, 1995. PubMed PMID: 7479822; PMCID: PMC40633.
Lemmon MA. Membrane recognition by phospholipid-binding domains. Nat Rev Mol Cell Biol. 2008;9(2):99-111. Epub Jan. 25, 2008. doi: 10.1038/nrm2328. PubMed PMID: 18216767.
Brewitz, Lennart, et al. "Thiophene-fused γ-lactams inhibit the SARS-CoV-2 main protease via reversible covalent acylation." Chemical Science 15.20 (2024): 7667-7678.
Han, Xu, et al. "Pleckstrin-2 mediates the activation of AKT in prostate cancer and is repressed by androgen receptor." The American Journal of Pathology 194. 10 (2024): 1986-1996.

* cited by examiner

17d-PROTACS

ORTEP structure

TARGETING PLECKSTRIN-2 FOR TREATING CANCER

CROSS-REFERENCE TO RELATED APPLICATIONS

The present application is a national stage application, filed under 35 U.S.C. § 371, of International Application No. PCT/US2019/059462, filed Nov. 1, 2019, and claims the benefit of priority under 35 U.S.C. § 119 (e) to U.S. Provisional Application No. 62/754,121, filed on Nov. 1, 2018, the contents of each of which are incorporated herein by reference in its their entirety.

STATEMENT REGARDING FEDERALLY SPONSORED RESEARCH OR DEVELOPMENT

This invention was made with government support under DK102718 awarded by the National Institutes of Health. The government has certain rights in the invention.

REFERENCE TO A SEQUENCE LISTING SUBMITTED VIA EFS-WEB

The content of the ASCII text file of the sequence listing names "702581_01632_ST25.txt" which is 3.31 kb in size was created on Oct. 29, 2019 and electronically submitted via EFS-Web herewith the application is incorporated herein by reference in its entirety.

BACKGROUND

The field of the invention relates to methods for treating cancers. In particular, the field of the invention relates to methods for treating cancer by targeting Pleckstrin-2 (Plek2) in particular with small molecule inhibitors.

Myeloproliferative neoplasms (MPNs) are a group of bone marrow diseases with excessive production of myeloid cells, increased risk of arterial or venous thrombosis, and a propensity to transform into acute myeloid leukemia (AML). Current therapies for MPNs are not curative and have significant drug resistance and side effects, which necessitate new therapeutic strategies. For example, the Janus kinase 2 (JAK2) V617F mutation, which results in JAK2 dysregulation, is found in the majority of Philadelphia chromosome (Ph)-negative myeloproliferative neoplasms (MPNs). (See, e.g., McLoman et al., "JAK2 V617F: A Single Mutation in the Myeloproliferative Group of Disorders," Ulster Med. J., 2006 May; 75(2):112-119, the content of which is incorporated by reference in its entirety). As such, therapy using JAK2 inhibitors that are targeted at JAK2 dysregulation have been one of the mainstays for treating Ph-negative MPNs. However, JAK2 inhibitors face many challenges including drug resistance and severe side effects.

Our recent published work reveals a novel target, named Pleckstrin-2 (Plek2), which is highly expressed in MPNs. (See Zhao et al., "Loss of pleckstrin-2 reverts lethality and vascular occlusions in JAK2V617F-positive myeloproliferative neoplasms, J. Clin. Invest., Nov. 20, 2017, the content of which is incorporated herein by reference in its entirety). Having identified Plek2 as being highly expressed in MPNs, we performed screens and used medicinal chemistry to identify several novel small molecule inhibitors of Plek2. We determined that the identified inhibitors are potent in blocking the in vitro proliferation of hyperproliferative hematopoietic cells and in vivo thrombosis formation. We also determined that one mechanism of the compounds is that they cluster phosphatidylinositide 3-kinase (PI3K) products and recruit PI3K-Akt pathway effectors. Activation of the PI3K-Akt pathway is implicated in the proliferation of a number of cancers. Treatment of hyperproliferative hematopoietic cells with the identified Plek2 inhibitors significantly inhibits the phosphorylation of Akt within the PI3K-Akt pathway. As such, our novel Plek2 inhibitors will have a broad therapeutic application in MPNs, as well as cancers with high Plek2 expression, especially those that are characterized by activation of the PI3K-Akt pathway, including solid tumors.

The identified compounds are expected to have significant advantages over the current drugs for MPN treatment. In particular, the identified compounds may be administered to decrease the incidence of blood clot formation, which is a major risk of mortality and mobility in patients with MPNs. Further, the identified compounds may be administered to treat MPNs in the early stage of disease development and decrease the incidence of blood clot formation.

SUMMARY

Disclosed herein are compounds, compositions, and methods for treating cell proliferative diseases and disorders based on the present inventors discovery that Pleckstrin-2 (Plek2) can be targeted to treat cell proliferative diseases and disorders. The compositions and methods disclosed herein typically include or utilize the disclosed compounds as therapeutic agents which inhibit the biological activity or expression of Pleckstrin-2 (Plek2) and collectively may be referred to as "Plek2 inhibitors."

Particularly disclosed are small molecule inhibitors of Plek2 biological activity. The compositions and methods may be utilized for treating cell proliferative diseases and disorders that are characterized by elevated levels of Plek2 expression and/or by activation of the phosphatidylinositide 3-kinase (PI3K)/Akt pathway. Cell proliferative diseases and disorders that may be treated using the disclosed compositions and methods may include, but are not limited to, myeloproliferative neoplasms (MPNs) such as Philadelphia (Ph)-negative MPNs, and cancers such as acute myeloid leukemia (AML) and cancers characterized by solid tumors, such as colorectal carcinoma, pancreatic cancer, lung cancer, renal carcinoma, and breast cancer.

BRIEF DESCRIPTION OF THE FIGURES

FIG. 15A. RBC and WBC count of indicated mice after NUP-17d treatment. Two-month-old $JAK2^{V617F}$ knockin mice were treated with NUP-17d once every two days for three weeks. Wild type (WT) littermate control mice were used for comparison *P<0.05;  P<0.01; * P<0.001. FIG. 15B. H&E stain of the spleen and lung sections. Inserted panels with high magnification reveal vascular occlusions. Scale bars: 100 μm.

DETAILED DESCRIPTION

Figure 1:
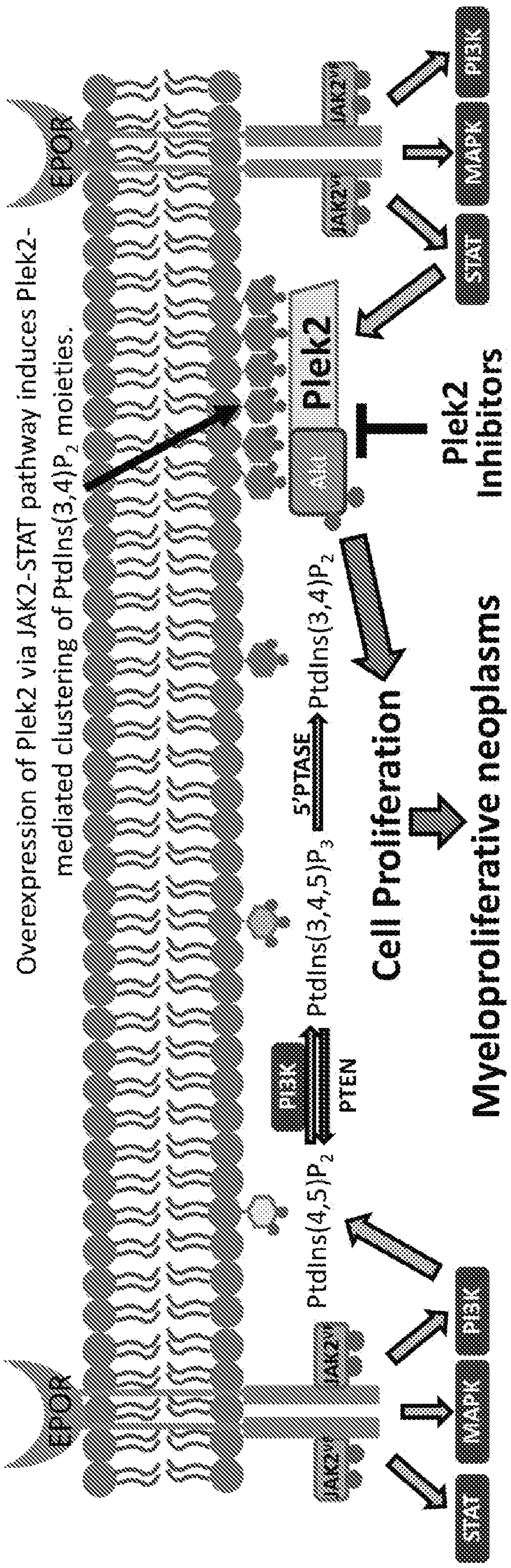
FIG. 1. Schematic view of the proposed mechanism of Plek2 function and drug target route. See text for details. JAK2VF represents JAK2V617F mutant.

The present invention is described herein using several definitions, as set forth below and throughout the application.

Definitions

Unless otherwise specified or indicated by context, the terms "a", "an", and "the" mean "one or more." For example, "a compound" or "an inhibitor" should be interpreted to mean "one or more compounds" and "one or more inhibitors," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, a "subject" may be interchangeable with "patient" or "individual" and means an animal, which may be a human or non-human animal, in need of treatment, for example, treatment by include administering a therapeutic amount of one or more therapeutic agents that inhibit the biological activity or expression of Pleckstrin-2 (Plek2). A "subject in need of treatment" may include a subject having a disease or disorder associated with expression or overexpression of Plek2, for example overexpression of an mRNA encoding the Plek2 protein. A "subject in need of treatment" may include a subject having a disease or disorder associated with activation of the phosphatidylinositide 3-kinase (PI3K)/Akt pathway.

The pleckstrin-2 (Plek2) protein is known in the art. The 353 amino acid sequence for the human Plek2 protein is deposited at GenBank as NCBI Reference Sequence: NP_057529.1. (See also SEQ ID NO:1).

A "subject in need of treatment" may include a subject having a cell proliferative disease, disorder, or condition such as cancer. Cancers may include, but are not limited to adenocarcinoma, leukemia, lymphoma, melanoma, myeloma, sarcoma, and teratocarcinoma and particularly cancers of the adrenal gland, bladder, blood, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

A "subject in need of treatment" may include a subject having a disease, disorder, or condition that is characterized as a myeloproliferative neoplasm (MPN). A "subject in need of treatment" may include a subject having a disease, disorder, or condition that is characterized as a Philadelphia chromosome (Ph)-negative MPN. A "subject in need of treatment" may include a subject having a disease, disorder, or condition that is characterized as acute myeloid leukemia (AML).

New Chemical Entities

New chemical entities and uses for chemical entities, for example as therapeutic agents, are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of an alkyl group (e.g., $-(CH_2)_n-$ where n is an integer such as an integer between 1 and 20). An exemplary alkylene group is $-CH_2CH_2-$.

The term "haloalkyl" refers to an alkyl group that is substituted with at least one halogen. For example, $-CH_2F$, $-CHF_2$, $-CF_3$, $-CH_2CF_3$, $-CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of

```
                                              SEQ ID NO: 1
  1  medgvlkegf lvkrghivhn wkarwfilrq ntlvyykleg grrvtppkgr illdgctitc

 61  pcleyenrpl liklktqtst eyfleacsre erdawafeit gaihagqpgk vqqlhslrns

121  fklpphislh rivdkmhdsn tgirsspnme qgstykktfl gsslvdwlis nsftasrlea

181  vtlasmlmee nflrpvgvrs mgairsgdla eqflddstal ytfaesykkk ispkeeisls

241  tvelsgtvvk qgylakqghk rknwkvrrfv lrkdpaflhy ydpskeenrp vggfslrgsl

301  vsaledngvp tgvkgnvqgn lfkvitkddt hyyiqasska eraewieaik klt
```

2-12, 2-10, or 2-6 carbon atoms, referred to herein as C2-C12-alkynyl, C2-C10-alkynyl, and C2-C6-alkynyl, respectively.

The term “cycloalkyl” refers to a monovalent saturated cyclic, bicyclic, or bridged cyclic (e.g., adamantyl) hydrocarbon group of 3-12, 3-8, 4-8, or 4-6 carbons, referred to herein, e.g., as “C4-8-cycloalkyl,” derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term “cycloalkylene” refers to a cycloalkyl group that is unsaturated at one or more ring bonds.

The term “partially unsaturated carbocyclyl” refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term “aryl” is art-recognized and refers to a carbocyclic aromatic group. Representative aryl groups include phenyl, naphthyl, anthracenyl, and the like. The term “aryl” includes polycyclic ring systems having two or more carbocyclic rings in which two or more carbons are common to two adjoining rings (the rings are “fused rings”) wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms “heterocyclyl” and “heterocyclic group” are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation “C3-C7” indicates that the heterocyclic ring contains a total of from 3 to 7 ring atoms, inclusive of any heteroatoms that occupy a ring atom position.

The terms “amine” and “amino” are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms “alkoxy” or “alkoxyl” are art-recognized and refer to an alkyl group, as defined above, having an oxygen radical attached thereto. Representative alkoxy groups include methoxy, ethoxy, tert-butoxy and the like.

An “ether” is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term “carbonyl” as used herein refers to the radical —C(O)—.

The term “oxo” refers to a divalent oxygen atom —O—.

The term “carboxamido” as used herein refers to the radical —C(O)NRR', where R and R' may be the same or different. R and R', for example, may be independently alkyl, aryl, arylalkyl, cycloalkyl, formyl, haloalkyl, heteroaryl, or heterocyclyl.

The term “carboxy” as used herein refers to the radical —COOH or its corresponding salts, e.g. —COONa, etc.

The term “amide” or “amido” or “amidyl” as used herein refers to a radical of the form —$R^1C(O)N(R^2)$—, —$R^1C(O)N(R^2)R^3$—, —$C(O)NR^2R^3$, or —$C(O)NH_2$, wherein $R^1$, $R^2$ and $R^3$, for example, are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term “stereoisomers” when used herein consist of all geometric isomers, enantiomers or diastereomers. These compounds may be designated by the symbols “R” or “S,” or “+” or “−” depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)” in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

Modulation of Pleckstrin-2 Activity and Expression

The compounds disclosed herein preferably modulate activity and/or expression of Pleckstrin-2 (Plek2). Modulation may include inhibiting or decreasing Plek2 activity or expression. Modulation also may include activating or increasing Plek2 activity or expression. Plek2 activity or expression may be assessed utilizing methods known in the art and the methods disclosed herein, including the methods disclosed in the Examples provided herein. In some embodiments, the compounds decrease or increase Plek2 activity or expression relative to a control (e.g., by at least about 10%, 20%, 30%, 40%, 50%, 60%, 70%, 80%, 90%, 100%, 200%, 300%, 400%, 500%, 600%, 700%, 800%, 900%, 1000% or more (or within a range bounded by any of these values)). In some embodiments, an $IC_{50}$ value for a compound in regard to modulating activity or expression of Plek2 may be determined and preferably the compound has an $IC_{50}$ value of less than about 10 μM, 5 μM, or 1 μM, 0.5 μM, 0.1 μM, 0.05 μM, 0.01 μM, 0.005 μM, or 0.001 μM (or within a range bounded by any of these values).

Pharmaceutical Compositions and Methods of Administration

The compounds disclosed herein may be administered as pharmaceutical compositions and, therefore, pharmaceutical compositions incorporating the compounds are considered to be embodiments of the subject matter disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that disrupts the SEC or inhibits the biological activity of the SEC may be administered as a single compound or in combination with another compound that disrupts the SEC or inhibits the biological activity of the SEC or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds disclosed herein or salts, esters, and/or amides, thereof. Solvate forms may include ethanol solvates, hydrates, and the like.

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein, the phrase "effective amount" shall mean that drug dosage that provides the specific pharmacological response for which the drug is administered in a significant number of subjects in need of such treatment. An effective amount of a drug that is administered to a particular subject in a particular instance will not always be effective in treating the conditions/diseases described herein, even though such dosage is deemed to be a therapeutically effective amount by those of skill in the art.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

When it is desired to administer the compound as a suppository, conventional bases can be used. Illustratively, cocoa butter is a traditional suppository base. The cocoa butter can be modified by addition of waxes to raise its melting point slightly. Water-miscible suppository bases, such as polyethylene glycols of various molecular weights, can also be used in suppository formulations.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

Targeting Pleckstrin-2 (Plek2) for Treating Cancer

The present inventors have determined that Pleckstrin-2 (Plek2) can be targeted to treat cell proliferative diseases and disorders. As such, the subject matter disclosed herein relates to compounds targeted to Plek2 and compounds and compositions and methods for treating cell proliferative diseases and disorders that include or utilize the disclosed compounds. The compositions and methods typically include or utilize the disclosed compounds as therapeutic agents which inhibit the biological activity or expression of Pleckstrin-2 (Plek2) and collectively may be referred to as "Plek2 inhibitors." Particularly disclosed are small molecule inhibitors of Plek2 biological activity.

In some embodiments, the disclosed compounds have the following Formula I or a salt, hydrate, or solvate thereof.

I

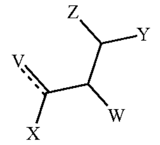

wherein:

V is hydrogen, hydroxyl, or keto;

W is hydrogen, hydroxyl, or alkyoxy;

X is 1H-indol-3-yl, N-alkyl-indol-3-yl, 1H-indazol-3-yl, or N-alkyl-indazol-3-yl optionally substituted at one or more positions with a substituent (e.g., $R^1$) selected from alkyl (e.g., methyl), cycloalkyl (e.g., cyclopropyl), cycloheteroalkyl (e.g., N-azetidinyl), alkoxy (e.g., methoxy), halo (e.g., fluoro or chloro), haloalkyl (e.g., trifluoromethyl), amino, and cyano;

Y is a 5-membered or 6-membered carbocycle or heterocycle (e.g., an N-, O-, or S-containing heterocycle) which optionally is saturated or unsaturated at one or more bonds and optionally is substituted at one or more positions with a substituent (e.g., $R^2$) selected from alkyl (e.g., methyl), cycloalkyl (e.g., cyclopropyl), cycloheteroalkyl (e.g., N-azetidinyl), alkoxy (e.g., methoxy), halo (e.g., fluoro or chloro), haloalkyl (e.g., trifluoromethyl), amino, and cyano; and Z is selected from —$NR^3R^4$ or —$OR^5$, wherein $R^3$ and $R^4$ are selected from hydrogen, alkyl, cycloalkyl or cycloheteroalkyl optionally substituted with alkyl, or $R^3$ and $R^4$ together form a 5-membered or 6-membered heterocycle (e.g., an N-, O-, or S-containing heterocycle) which is saturated or unsaturated at one or more bonds and is substituted at one or more positions with a substituent selected from alkyl (e.g., methyl), cycloalkyl (e.g., cyclopropyl), cycloheteroalkyl (e.g., N-azetidinyl), alkoxy (e.g., methoxy), halo (e.g., fluoro or chloro), haloalkyl (e.g., trifluoromethyl), hydroxyalkyl (e.g., hydroxyethyl), amino, and cyano; $R^5$ is selected from hydrogen, alkyl, and cycloalkyl.

In particular, the disclosed compounds may include a keto group at position V of Formula I. Further, in some embodiments, the disclosed compounds may include a hydroxyl group at position W of Formula I.

In some embodiments of the compounds having Formula I, the compounds have an optionally substituted 1H-indol-3-yl group, N-alkyl-indol-3-yl group, 1H-indazol-3-yl group, or N-alkyl-indazol-3-yl group at position X. For example, in some embodiments, the disclosed compounds may have a formula selected from:

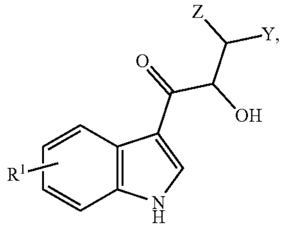

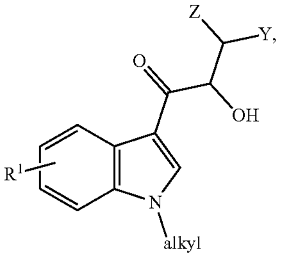

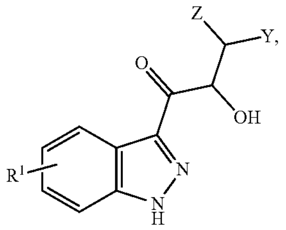

and

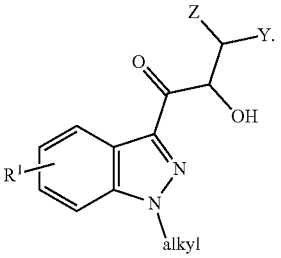

In particular, the disclosed compounds having Formula I may include compounds in which X is selected from:

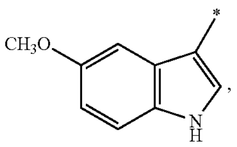

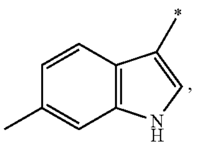

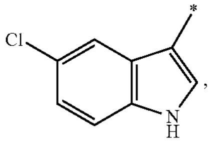

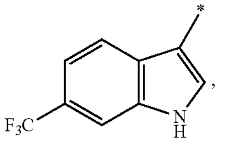

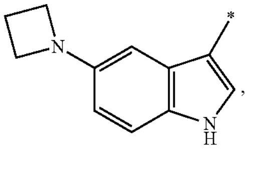

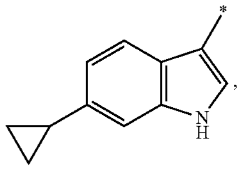

-continued

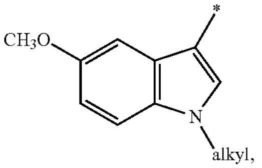
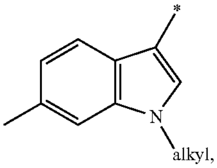
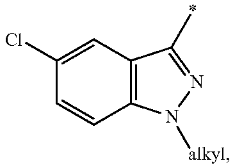
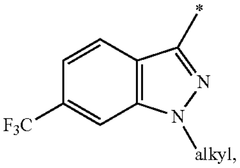
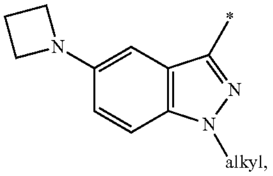
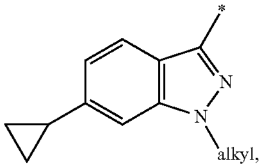
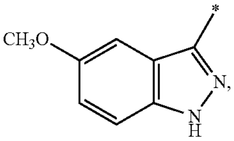
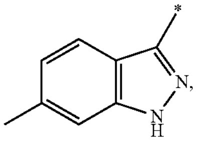
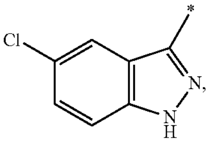
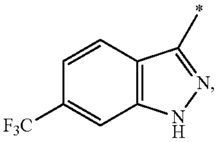
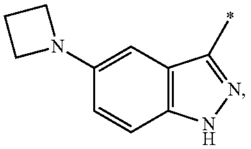
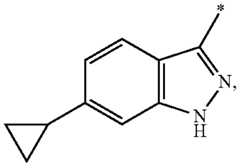
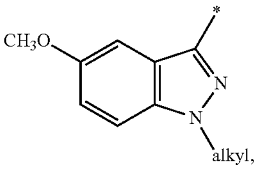
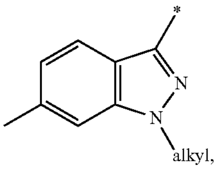
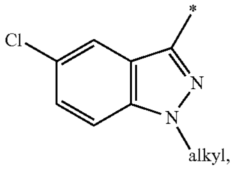
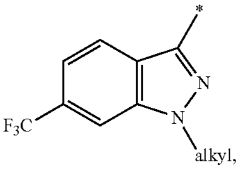
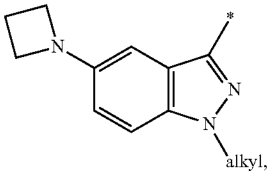 and
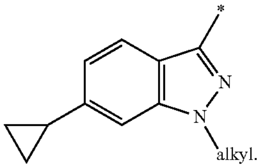

In the disclosed compounds having Formula I, Y is an optionally substituted 5-membered or 6-membered carbocycle or heterocycle (e.g., an N-, O-, or S-containing heterocycle) which optionally is saturated or unsaturated at one or more bonds. In some embodiments, Y is selected from phenyl, pyridinyl (e.g., pyridin-4-yl), and thiophenyl (e.g., thiophen-2-yl). In particular, the disclosed compounds having Formula I may include compounds in which Y is selected from:

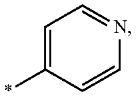
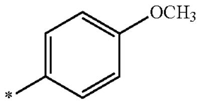 ,
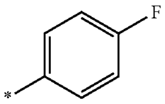 ,
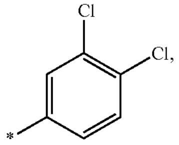
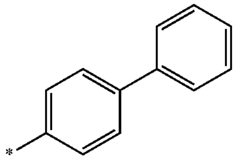 and
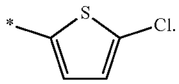

In the disclosed compounds having Formula I, Z is selected from —$NR^3R^4$ or —$OR^5$, wherein $R^3$ and $R^4$ are selected from hydrogen, alkyl, cycloalkyl or cycloheteroalkyl optionally substituted with alkyl, or $R^3$ and $R^4$ together form an optionally substituted 5-membered or 6-membered heterocycle (e.g., an N-, O-, or S-containing heterocycle) which is saturated or unsaturated at one or more bonds. In some embodiments of the disclosed compounds, Z is —$NR^3R^4$ and $R^3$ and $R^4$ are selected from hydrogen and alkyl. In other embodiments of the disclosed compounds having Formula I, Z is —$NR^3R^4$ and $R^3$ and $R^4$ together form a 5-membered or 6-membered heterocycle (e.g., an N-, O-, or S-containing heterocycle) which is saturated or unsaturated at one or more bonds and is substituted at one or more positions with a substituent selected from alkyl (e.g., methyl), cycloalkyl (e.g., cyclopropyl), cycloheteroalkyl (e.g., N-azetidinyl), alkoxy (e.g., methoxy), halo (e.g., fluoro or chloro), haloalkyl (e.g., trifluoromethyl), amino, and cyano; $R^5$ is selected from hydrogen, alkyl, and cycloalkyl. In further embodiments of the disclosed compounds having Formula I, Z is —$OR^5$ and $R^5$ is selected from hydrogen, alkyl, and cycloalkyl.

In particular, the disclosed compounds having Formula I may include compounds in which Z is selected from

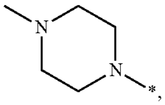
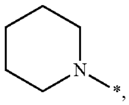
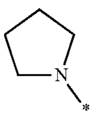
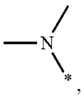
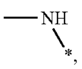
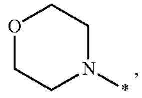
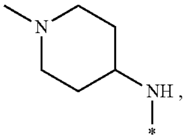 and
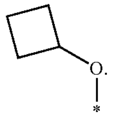

Particular compounds disclosed herein include compounds having a formula selected from:

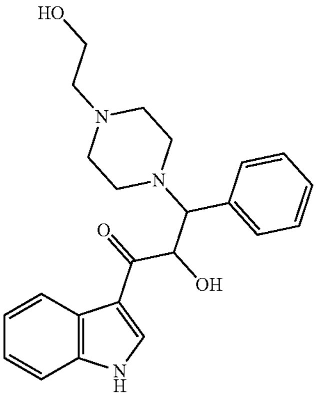
,

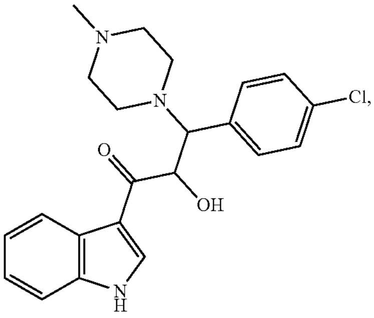
, and

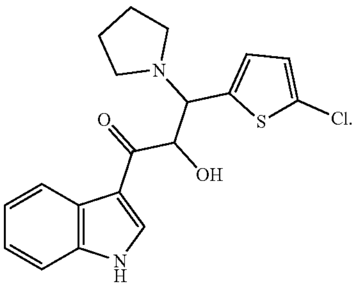
.

In some embodiments of the disclosed compounds, the compounds further may be conjugated to a moiety which targets Plesckin-2 (Plek2) for degradation. For example, the disclosed compounds may be utilized to prepare proteolysis-targeting chimeric molecules (PROTACs) that are targeted to Plek2. PROTACs are heterobifunctional small molecules that simultaneously bind a target protein and a ubiquitin ligase and are known in the art. (See, e.g., Deschaies, "Prime Time for PROTACS," Nature Chem. Biol., 11, 634-635 (2015); Neklesa et al., "Targeted protein degradation by PROTACs," Pharma & Ther., Vol. 174, June 2017, Pages 138-144; Gu et al., "PROTACs: An Emerging Targeting Technique for Protein Degradation in Drug Discovery," BioEssays, 2018, 40 17000247, 1-11; Bondeson et al., "Lesson in PROTAC Design from Selective Degradation with a Promiscuous Warhead," Cell Chemical Biology, Vol. 25, No. 1, P78-87, (2018); the contents of which are incorporated herein by reference in their entireties). As such, contemplated herein are PROTACs comprising the compounds disclosed herein which simultaneously bind Pleckstrin-2 (Plek2) and ubiquitin ligase.

In some embodiments of the disclosed compounds, the compounds further may be conjugated (e.g., covalently) to an ubiquitin ligase recruiter (e.g., an E3 ligase recruiter) as part of a PROTAC. In some embodiments, the E3 ligase recruiter has a formula:

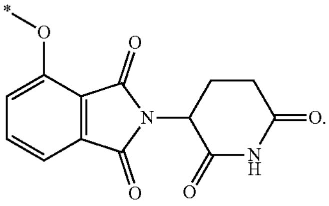 [SMILES: *Oc1cccc2c1C(=O)N(C1CCC(=O)NC1=O)C2=O]
.

Figure 14:
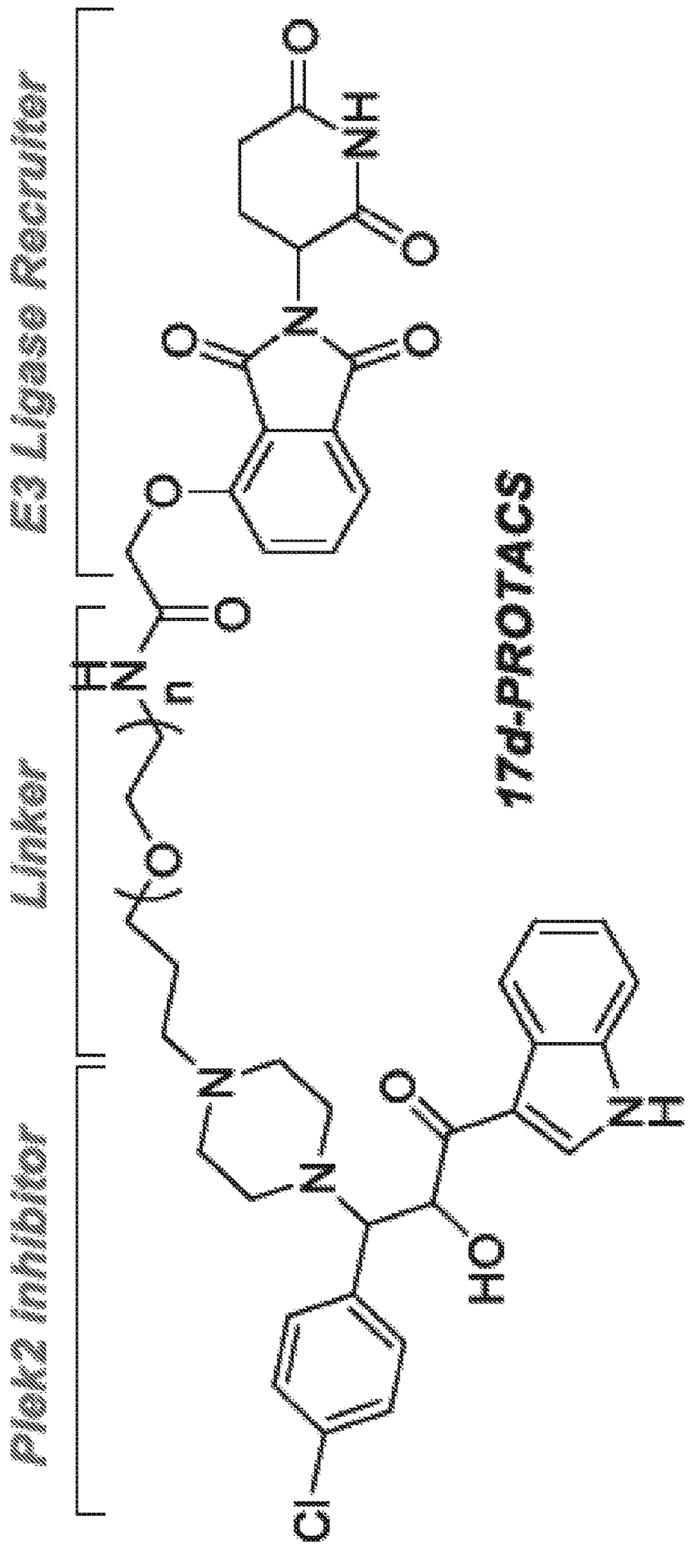
FIG. 14. Illustrative compound comprising Plek2 inhibitor linked to E3 Ligase recruiter.

The disclosed compounds may be disclosed directly or indirectly (e.g., via a linker) to an ubiquitin ligase recruiter such as an E3 ligase recruiter. In some embodiments, the compound is conjugated to an E3 ligase recruiter via a linker, optionally wherein the linker comprises a moiety having a formula $-(OCH_2CH_2)_n-NHC(O)-$ and n is 1-6. In particular, the disclosed compounds may be conjugated indirectly to an E3 ligase recruiter via a linker and may have a formula as illustrated in FIG. 14.

Also disclosed herein are pharmaceutical compositions. For example, disclosed herein are pharmaceutical compositions comprising the compositions disclosed herein optionally together with a suitable pharmaceutical carrier. The pharmaceutical compositions may be administered to a subject in need thereof to treat a disease or disorder as described herein.

In some embodiments, the disclosed pharmaceutical compositions are administered to a subject in need thereof, wherein the subject has a cell proliferative disease or disorder. Suitable cell proliferative diseases and disorders treated by the disclosed methods may include but are not limited to cell proliferative diseases and disorders that are characterized by overexpression of Pleckstrin-2 (Plek2) or activation of the phosphatidylinositide 3-kinase (PI3K)/Akt pathway. Suitable cell proliferative diseases and disorders treated by the disclosed methods may include but are not limited to myeloproliferative neoplasms such as Philadelphia chromosome (Ph)-negative MPNs. Suitable cell proliferative diseases and disorders treated by the methods may include but are not limited to leukemias such as acute myeloid leukemia (AML). In some embodiments, suitable cell proliferative diseases and disorders treated by the disclosed methods may include cancers characterized by a solid tumor.

ILLUSTRATIVE EMBODIMENTS

The following Embodiments are illustrative and should not be interpreted to limit the scope of the claimed subject matter.

Embodiment 1. A compound having the following formula or a salt, hydrate, or solvate thereof:

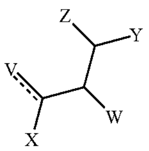

wherein:

V is hydrogen, hydroxyl, or keto;

W is hydrogen, hydroxyl, or alkyoxy;

X is 1H-indol-3-yl, N-alkyl-indol-3-yl, 1H-indazol-3-yl, or N-alkyl-indazol-3-yl optionally substituted at one or more positions with a substituent (e.g., $R^1$) selected from alkyl (e.g., methyl), cycloalkyl (e.g., cyclopropyl), cycloheteroalkyl (e.g., N-azetidinyl), alkoxy (e.g., methoxy), halo (e.g., fluoro or chloro), haloalkyl (e.g., trifluoromethyl), amino, and cyano;

Y is a 5-membered or 6-membered carbocycle or heterocycle (e.g., an N-, O-, or S-containing heterocycle) which optionally is saturated or unsaturated at one or more bonds and optionally is substituted at one or more positions with a substituent (e.g., $R^2$) selected from alkyl (e.g., methyl), cycloalkyl (e.g., cyclopropyl), cycloheteroalkyl (e.g., N-azetidinyl), alkoxy (e.g., methoxy), halo (e.g., fluoro or chloro), haloalkyl (e.g., trifluoromethyl), amino, and cyano; and Z is selected from —$NR^3R^4$ or —$OR^5$, wherein $R^3$ and $R^4$ are selected from hydrogen, alkyl, cycloalkyl or cycloheteroalkyl optionally substituted with alkyl, or $R^3$ and $R^4$ together form a 5-membered or 6-membered heterocycle (e.g., an N-, O-, or S-containing heterocycle) which is saturated or unsaturated at one or more bonds and optionally is substituted at one or more positions with a substituent selected from alkyl (e.g., methyl), cycloalkyl (e.g., cyclopropyl), cycloheteroalkyl (e.g., N-azetidinyl), alkoxy (e.g., methoxy), halo (e.g., fluoro or chloro), haloalkyl (e.g., trifluoromethyl), hydroxyalkyl (e.g., hydroxyethyl), amino, and cyano; $R^5$ is selected from hydrogen, alkyl, and cycloalkyl.

Embodiment 2. The compound of embodiment 1, wherein V is keto and W is hydroxyl.

Embodiment 3. The compound of embodiment 1 or 2, having a formula selected from:

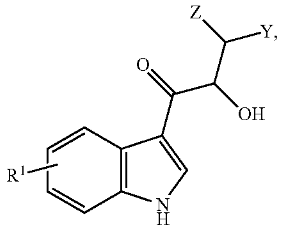
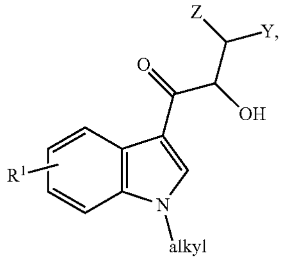
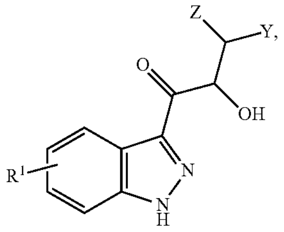
and
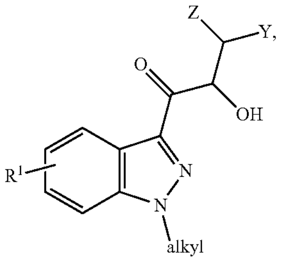

wherein $R^1$ selected from hydrogen, alkyl (e.g., methyl), cycloalkyl (e.g., cyclopropyl), cycloheteroalkyl (e.g., N-azetidinyl), alkoxy (e.g., methoxy), halo (e.g., fluoro or chloro), haloalkyl (e.g., trifluoromethyl), amino, and cyano Embodiment 4. The compound of any of the foregoing embodiments wherein X is selected from:

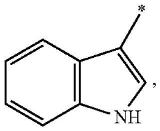
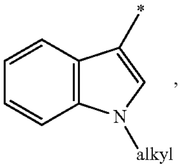
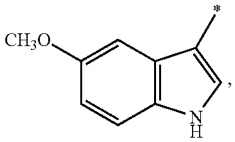
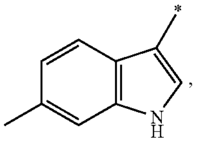
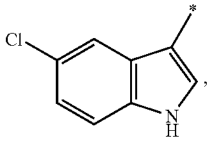
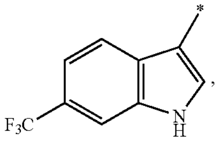
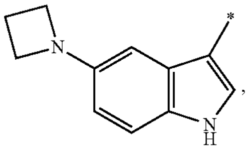
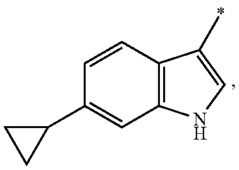
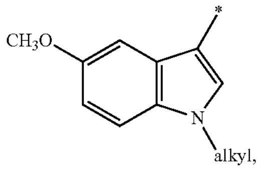
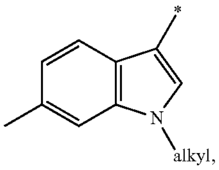
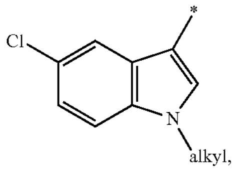
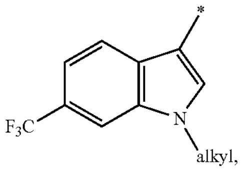
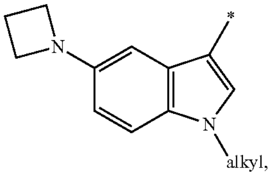
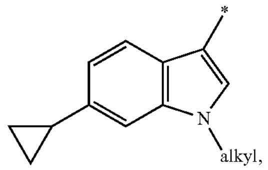
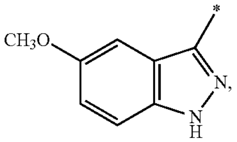
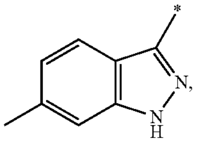
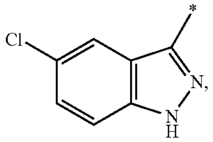
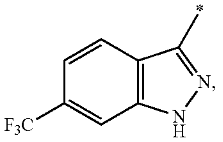
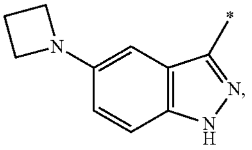
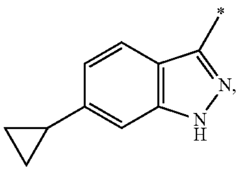

-continued

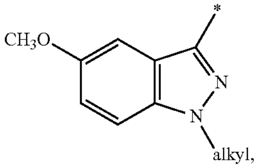

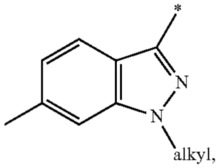

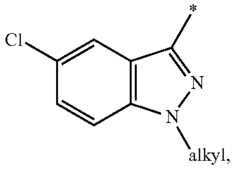

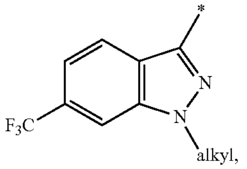

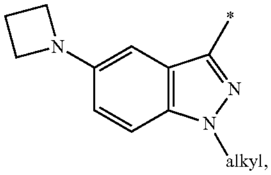

and

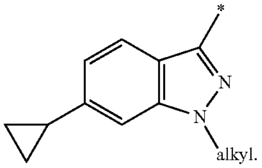

Embodiment 5. The compound of any of the foregoing embodiments, wherein Y is selected from phenyl, pyridinyl (e.g., pyridin-4-yl), and thiophenyl (e.g., thiphen-2-yl), optionally substituted at one or more positions with a substituent (e.g., $R^2$) selected from alkyl (e.g., methyl), cycloalkyl (e.g., cyclopropyl), cycloheteroalkyl (e.g., N-azetidinyl), alkoxy (e.g., methoxy), halo (e.g., fluoro or chloro such as dichloro), haloalkyl (e.g., trifluoromethyl), aryl (e.g., phenyl), amino, and cyano.

Embodiment 6. The compound of any of the foregoing embodiments, wherein Y is selected from:

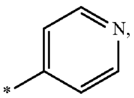

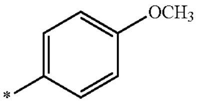

,

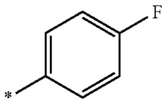

,

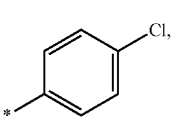

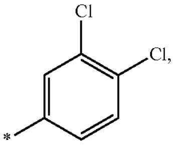

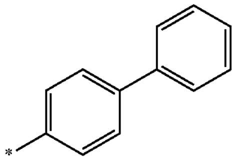

, and

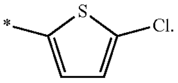

Embodiment 7. The compound of any of the foregoing embodiments, wherein Z is —$NR^3R^4$ and $R^3$ and $R^4$ are selected from hydrogen and alkyl.

Embodiment 8. The compound of any of embodiments 1-6, wherein Z is —$NR^3R^4$ and $R^3$ and $R^4$ together form a 5-membered or 6-membered heterocycle (e.g., an N-, O-, or S-containing heterocycle) which is saturated or unsaturated at one or more bonds and optionally is substituted at one or more positions with a substituent selected from alkyl (e.g., methyl), cycloalkyl (e.g., cyclopropyl), cycloheteroalkyl (e.g., N-azetidinyl), alkoxy (e.g., methoxy), halo (e.g., fluoro or chloro), haloalkyl (e.g., trifluoromethyl), amino, and cyano; $R^5$ is selected from hydrogen, alkyl, and cycloalkyl.

Embodiment 9. The compound of any of embodiments 1-6, wherein Z is —$OR^5$ and $R^5$ is selected from hydrogen, alkyl, and cycloalkyl.

Embodiment 10. The compound of any of the foregoing embodiments, wherein Z is selected from:

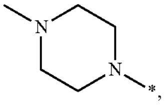

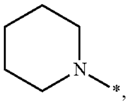

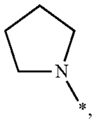

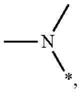

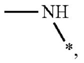

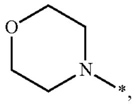

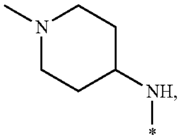

and

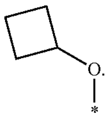

Embodiment 11. The compound of any of the foregoing embodiments having a formula selected from:

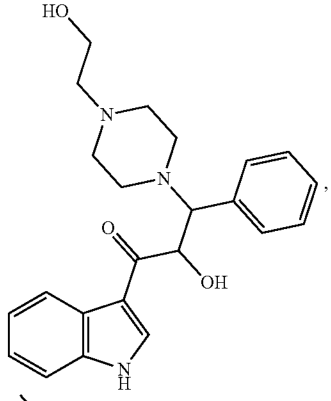

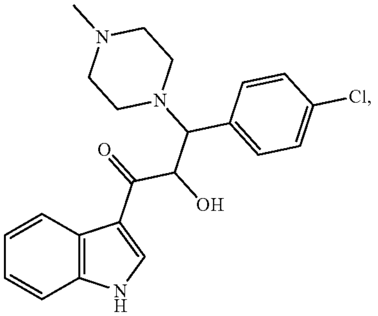

and

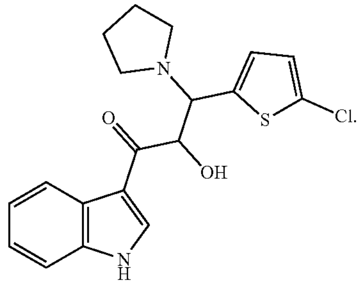

Embodiment 12. The compound of any of the foregoing embodiments of a formula:

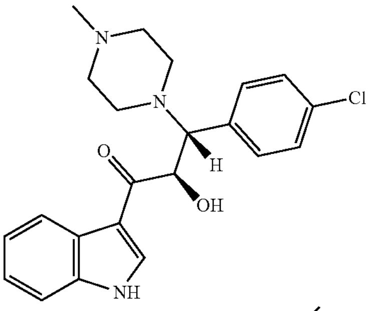

or

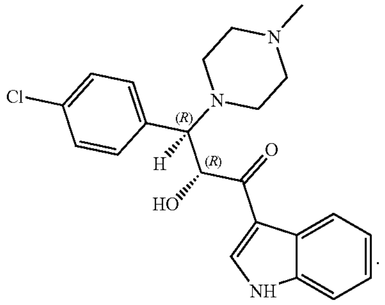

Embodiment 13. The compound of any of the foregoing embodiments further conjugated to an E3 ligase recruiter.

Embodiment 14. The compound of embodiment 13, wherein the E3 ligase recruiter has a formula:

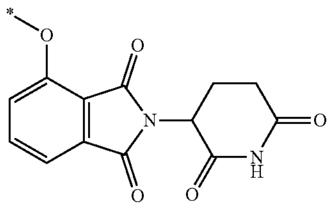 [SMILES: *Oc1cccc2c1C(=O)N(C1CCC(=O)NC1=O)C2=O]

Embodiment 15. The compound of embodiment 13 or 14, wherein the compound is conjugated to the E3 ligase recruiter via a linker, optionally wherein the linker comprises a moiety having a formula $-(OCH_2CH_2)_n-NHC(O)-$ and n is 1-6.

Embodiment 16. A pharmaceutical composition comprising the compound of any of the foregoing embodiments and a suitable pharmaceutical carrier.

Embodiment 17. A method for treating a cell proliferative disease or disorder in a subject in need thereof, the method comprising administering to the subject the pharmaceutical composition of embodiment 16.

Embodiment 18. The method of embodiment 17, wherein the cell proliferative disease or disorder is characterized by overexpression of Pleckstrin-2 (Plek2) or activation of the phosphatidylinositide 3-kinase (PI3K)/Akt pathway.

Embodiment 19. The method of embodiment 17 or 18, wherein the cell proliferative disease or disorder is a Philadelphia chromosome (Ph)-negative myeloproliferative neoplasm (MPN), optionally wherein the disease is acute myeloid leukemia (AML) or other hematological diseases.

Embodiment 20. The method of embodiment 17 or 18, wherein the cell proliferative disease or disorder is a cancer characterized by a solid tumor.

Embodiment 21. A method for treating a cell proliferative disease or disorder in a subject in need thereof, the method comprising administering to the subject a pharmaceutical composition comprising a therapeutic agent that inhibits the biological activity or expression of Pleckstrin-2 (Plek2).

Embodiment 22. The method of embodiment 21, wherein the cell proliferative disease or disorder is characterized by overexpression of Pleckstrin-2 (Plek2) or activation of the phosphatidylinositide 3-kinase (PI3K)/Akt pathway.

Embodiment 23. The method of embodiment 21 or 22, wherein the cell proliferative disease or disorder is a Philadelphia chromosome (Ph)-negative myeloproliferative neoplasm (MPN), optionally wherein the disease is acute myeloid leukemia (AML) or other hematological diseases.

Embodiment 24. The method of embodiment 21 or 22, wherein the cell proliferative disease or disorder is a cancer characterized by a solid tumor.

EXAMPLES

The following Examples are illustrative and should not be interpreted to limit the scope of the claimed subject matter.

Example 1—Targeting Pleckstrin-2 (Plek2) for Treating Myeloproliferative Neoplasms (MPNs) and Other Cancers Abstract Myeloproliferative neoplasms (MPNs) are a group of bone marrow diseases with excessive production of myeloid cells and increased risk of evolving to acute myeloid leukemia. JAK2V617F mutation is the leading cause of the Philadelphia chromosome (Ph)-negative MPNs (1-5). The discovery of this driver mutation led to the development of JAK inhibitors for the treatment of MPNs. Reduction in spleen size and blood cell counts has been reported in MPN patients treated with JAK inhibitor ruxolitinib (6, 7). However, distinct from the targeted therapy of BCR-ABL positive chronic myeloid leukemia, JAK2 is indispensable for normal hematopoiesis. Significant side effects including anemia and thrombocytopenia were inevitable when high doses of ruxolitinib were attempted (8). In addition, JAK inhibitor is not curative for the disease. Most patients with chronic JAK inhibitor treatment failed to reach molecular and pathologic remissions (6). MPN cells can also acquire adaptive resistance to chronic JAK inhibitor treatment through heterodimerization and transactivation of JAK2 by JAK1 and TYK2 (9). Furthermore, increased incidence of skin tumors or high grade B-cell lymphoma has been revealed in ruxolitinib-treated patients who have prior history of nonmelanoma skin cancers or pre-existing B cell clones, respectively (10, 11). These studies indicate that new targeted therapeutic strategies are needed to treat the disease.

Our recently unpublished study identified that Pleckstrin-2 (Plek2), a paralog of Pleckstrin-1 (Plek1) involved in actin dynamics (12-14), was a downstream effector of the JAK2-STAT5 pathway (15). We revealed that Plek2 was overexpressed in JAK2V617F positive MPN patients. Through a mouse genetic approach, we further discovered that knockout of Plek2 significantly ameliorated the MPN phenotypes in JAK2V617F knockin mice including reticulocytosis, thrombocytosis, neutrophilia, and splenomegaly. More significantly, loss of Plek2 reverted the widespread vascular occlusions and lethality of JAK2V617F knockin mice (15). These studies demonstrate that Plek2 is critical for the pathogenesis of MPNs with the activated JAK2-STAT5 pathway, and form a strong foundation for the development of Plek2 inhibitors for the treatment of MPNs. Importantly, our published study showed that Plek2 knockout mice did not develop anemia or cytopenia, indicating Plek2's oncogenic potential is only in the disease background and makes Plek2 inhibitor less likely to cause severe side effects. To this end, we have used an in silico approach to screen putative Plek2 binding small molecules and identified hit and lead compounds that showed potent in vitro and in vivo effects to block myeloproliferation in our studies. Our data also reveal that Plek2 binds to several PI3K effectors and loss of Plek2 reduces Akt activation, which leads to our hypothesis that Plek2 inhibitors revert myeloproliferation through the inhibition of the PI3K-Akt signaling.

Strategy

Significance. The Philadelphia chromosome (Ph)-negative myeloproliferative neoplasms (MPNs) are a group of bone marrow diseases with excessive production of myeloid cells and increased risk of evolving to acute myeloid leukemia. There are three main types of MPNs: polycythemia vera (PV), essential thrombocythemia (ET), and primary myelofibrosis (PMF). Clinically, PV and ET are characterized by an increased risk of thrombosis, hemorrhage, and evolution to myelofibrosis or acute myeloid leukemia (AML). The major therapeutic goals of PV and ET are to prevent the first occurrence and recurrence of thrombotic complications in the early stages of the diseases (16). Current first-line therapy includes aspirin, hydroxyurea, interferon α, anagrelide, or hydroxycarbamide. However, these treatment approaches remain suboptimal with ongoing risks for thrombosis, hemorrhage, impaired quality of life, and risk of transformation (7, 16). Poor tolerability for interferon α, contradictory leukemogenic risk of hydroxyurea, unresponsive aspirin treatment, and increased risk of arterial thrombosis with anagrelide therapy are all among the major challenges and unmet medical needs in the MPN field.

The JAK2V617F mutation is the leading cause of Ph-negative MPNs (1-5). The discovery of this driver mutation led to the development of JAK inhibitors for the treatment of MPNs (7). Reduction in spleen size and blood cell counts has been reported in MPN patients treated with JAK inhibitor ruxolitinib (6). However, distinct from the targeted therapy of BCR-ABL positive chronic myelogenous leukemia, JAK2 is indispensable for normal hematopoiesis. Significant side effects including anemia and thrombocytopenia were inevitable when high doses of JAK inhibitor were attempted (6, 8). In addition, JAK inhibitor therapy is not curative for the disease. Most patients treated chronically with JAK inhibitors failed to reach molecular and pathologic remissions (8). MPN cells can also acquire adaptive resistance to chronic JAK inhibitor treatment through heterodimerization and transactivation of JAK2 by JAK1 and TYK2 (9). Furthermore, increased incidence of skin tumors or high grade B-cell lymphoma has been revealed in ruxolitinib-treated patients who have prior history of nonmelanoma skin cancers or preexisting B-cell clones, respectively (11, 16). These studies indicate that new targeted therapeutic strategies are urgently needed to treat the disease.

Significantly, patients with Ph-negative MPNs are characterized by a distinct gene expression profile with upregulation of JAK-STAT downstream genes, regardless of the JAK2 mutational status (17). More recent studies further confirmed that patients with calreticulin (CALR) or MPL mutations, the other two major genetic abnormalities in Ph-negative MPNs (18), also involve activation of the JAK-STAT pathway (19, 20). These reports underscore the JAK-STAT pathway in the pathogenesis of MPNs as a valid target for therapy. However, there are currently no therapeutic approaches targeting JAK-STAT effectors.

This provided motivation for our research efforts to develop novel compounds targeting the JAK-STAT pathway for the treatment of myeloproliferative neoplasms. In this respect, our recently published study demonstrated a critical role of Plek2, a novel downstream target of JAK2-STAT5 pathway, in MPN pathogenesis in patients and in a JAK2V617F knock-in mouse model. Using a mouse genetic approach, we demonstrated that loss of Plek2 dramatically ameliorated JAK2V617F-induced reticulocytosis, increased body red cell mass, splenomegaly, and vascular occlusions (15). Importantly, Plek2 knockout mice did not show phenotypic abnormalities including hematologic disorders, indicating Plek2's role in a disease-specific manner (15). These data form the strong foundation for drug development targeting Plek2 for the treatment of MPNs.

To this end, we have performed in silico screening of putative Plek2 binding small molecules and identified hit compounds that showed potent in vitro and in vivo effects to block myeloproliferation. Our mechanistic investigation also reveals that Plek2 functions through the phosphoinositide 3-kinase (PI3K) pathway. The hit compound and its analog inhibit Plek2's function through interference of the PI3K pathway and reduction of the phosphorylation of protein kinase B (PKB)/Akt. Therefore, Plek2 functions as a central hub to mediate JAK2-STAT and PI3K-Akt pathways to promote tumor cell proliferation (FIG. 1). Development of Plek2 inhibitors will be critical to disrupt this connection. This mechanistic study also provides yet another mechanism how PI3K-Akt pathway is activated in MPNs (21-23). The potential therapeutic use of Plek2 inhibitors involves not only the reduction of myeloproliferation through targeting JAK2-STAT5 effector and PI3K-Akt activation, but also the amelioration of thrombosis through the reduction of whole-body red blood cell mass.

Innovation. To the best of our knowledge, Plek2 has not been identified as a target for MPN or other cancer therapies. If successful, Plek2 inhibitors will represent an important "first-in-class" compound in the field. The novelty of our project also lies in our discovery of Plek2 as a new target of the JAK2-STAT5 pathway, which is previously undescribed. Loss of Plek2 significantly ameliorates JAK2V617F-induced myeloproliferation and vascular occlusion. More important, our hit and lead compounds showed in vitro and in vivo efficacies similar to what have been found with our Plek2 knockout study. Equally important, our mechanistic study will reveal novel functions of Plek2 as a scaffolding protein enhancing the PI3K-Akt pathway.

Approach

Rationale of Targeting Plek2 as a Novel Approach to Treat MPNs.

Figure 2:
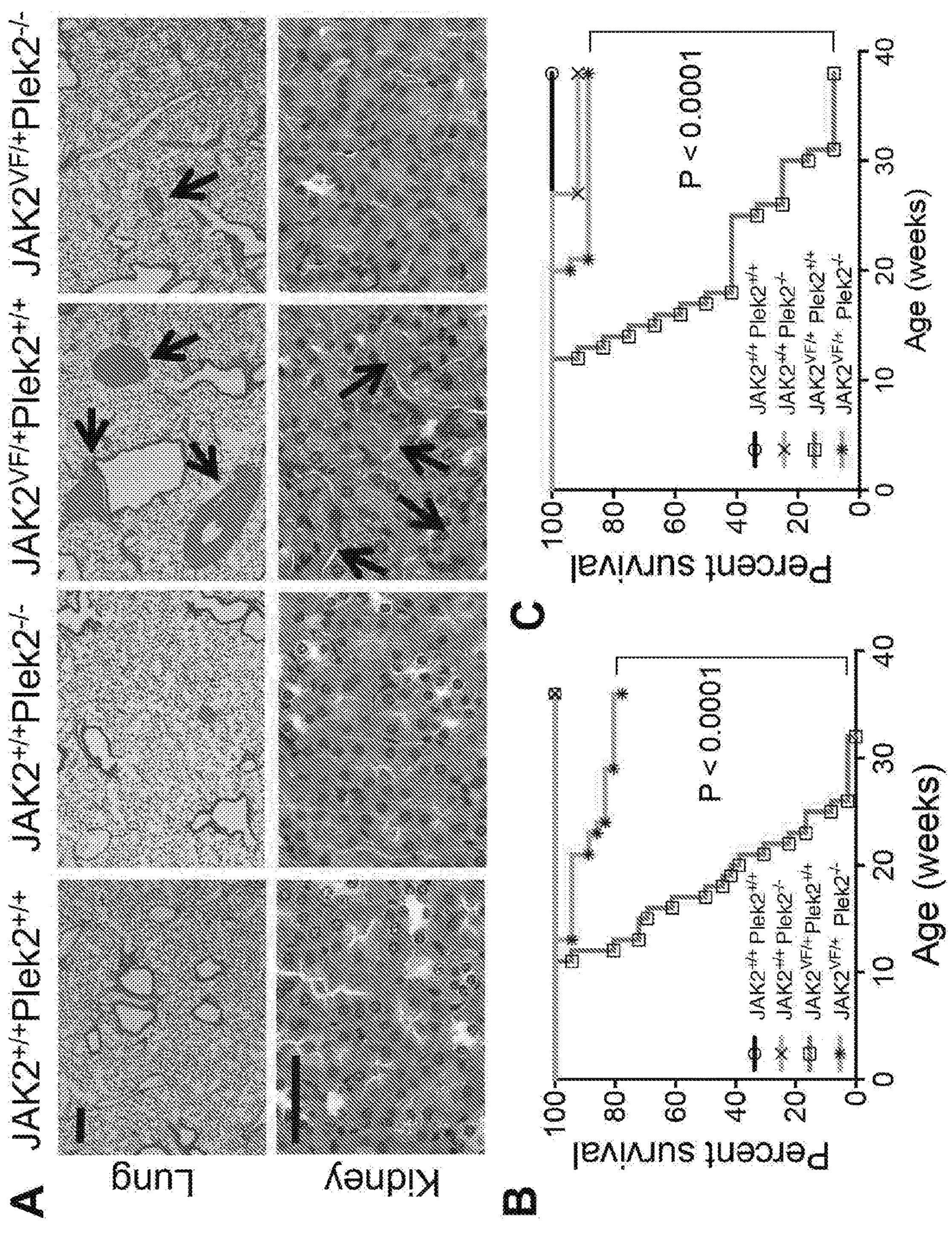
FIG. 2. Loss of Plek2 ameliorates JAK2V617F-induced myeloproliferation and reverts vascular occlusion and lethality. (A) Histologic examination of the lungs and kidneys of the indicated mice. The histologic images are representative of 5 mice in each group analyzed. Arrows indicate vascular occlusions with diameters larger than 50 μm in the lungs (top panels) and numerous small occlusions in the kidneys (bottom panels). Scale bars, 100 μm. (B) Kaplan-Meier survival analysis of indicated mice. Both males and females were included in each group. JAK2+/+ Plek2+/+ mice, n=34; JAK2+/+Plek2−/− mice, n=34; JAK2VF/+Plek2+/+ mice, n=36; JAK2VF/+Plek2−/− mice, n=36. (C) Bone marrow mononuclear cells from the indicated mice were transplanted into lethally irradiated wild type mice and monitored for survival as in B. N=10-17 in each group.

Our recently published studies identify that Pleckstrin-2 (Plek2), a widely-expressed paralog of Pleckstrin-1 (Plek1) involved in actin dynamics (13, 14), is a downstream effector of the JAK2-STAT5 pathway (15). Importantly, we showed that Plek2 is overexpressed in JAK2V617F positive MPN patients using real-time PCR, western blotting, and immunohistochemical stain techniques. Through a mouse genetic approach, we further discovered that knockout of Plek2 significantly ameliorated the MPN phenotypes in JAK2V617F knockin mice including reticulocytosis, thrombocytosis, neutrophilia, and splenomegaly. More significant, loss of Plek2 reverted the widespread thrombosis and lethality of JAK2V617F knockin mice (FIG. 2A-B). Transplantation of bone marrow cells from these mice to wild type recipients also revealed the same phenotypes, conforming the hematopoietic-specific roles of Plek2 (FIG. 2C). Significantly, our results revealed that Plek2 knockout mice did not exhibit hematologic abnormalities at a young age. Mild anemia was observed in mice over one year of age, which did not affect the overall survival of Plek2 knockout mice (15). These studies indicate that the pathophysiologic significance of Plek2 was mainly exhibited in the JAK2V617F mutant background, which is important for the development of Plek2 inhibitors to treat MPNs since these agents would be less likely to have severe side effects compared to JAK2 inhibitors. Based on these published work, we have screened for small molecule inhibitors of Plek2 for the treatment of MPNs and thrombosis in these patients.

High throughput screening and hit compound discovery. Plek2 contains two Pleckstrin Homology (PH) domains on the N and C terminus of the protein, which flank a Dishevelled, Egl-10 and Pleckstrin (DEP) domain in between. Pervious loss of function studies on the different domains of Plek2 showed that loss of DEP domain induced the most significant functional defects in Plek2 (14). The crystal structure of Plek2 is currently not available, so we built a homology model of Plek2. Considering the primary amino acid sequence of Plek2 as the query, we identified relevant template structures by homology search using BLAST and PSI-BLAST engines. The search did not yield a single template with more than 40% sequence homology to the query and hence multiple template with sequence homology more than 25% were considered. We built a comparative homology model of Plek2 following the method described before (24).

The Plek2 model was then subjected to MolProbity validation and model scored more than 95%, indicating its suitability to carry out further in silico work (25). After validating the model, the Site-Map module from Schrodinger was used to identify the putative ligand binding site along with the druggability score (26). A well-defined binding pocket was identified which also contained the critical residues identified earlier through mutagenesis study (14). We then performed a virtual high throughput screening (vHTS) using a 3-tier Glide platform implemented in Schrodinger suite (27). We screened approximately 100,000 drug-like small molecule compounds that could bind to Plek2 DEP domain. From this set, we identified 40 compounds that potentially bind to and inhibit the function of Plek2.

To screen these compounds, we performed an assay using a well-developed Plek2 functional screening system (28). In this system, we purified the mouse fetal liver erythroid progenitors and cultured them in erythropoietin containing medium. These cells underwent rapid proliferation closely mimicking accelerated erythropoiesis in MPNs. In these cells, Plek2 is also highly expressed during the culture (FIG. 3A). We tested each of the 40 hits from the vHTS in this culture system and found compounds NUP-2 and NUP-17 to be effective. Compound NUP-17 (FIG. 3B) showed a more specific and dramatic inhibition of cell proliferation and terminal enucleation of the erythroblasts (FIG. 3C-D). The IC50 is approximately 40 μM. Modeling the Plek2 DEP domain and its binding to NUP-17 shows putative binding residues on Plek2 (FIG. 3E involved amino acids are highlighted in yellow). Notably, lysine 157, arginine 194, and aspartic acid 166 have been shown in a previous mutagenesis study to be specific and functionally indispensable for Plek2 (14), which further implies the binding specificity and inhibitory potential of NUP-17 on Plek2.

Figure 4:
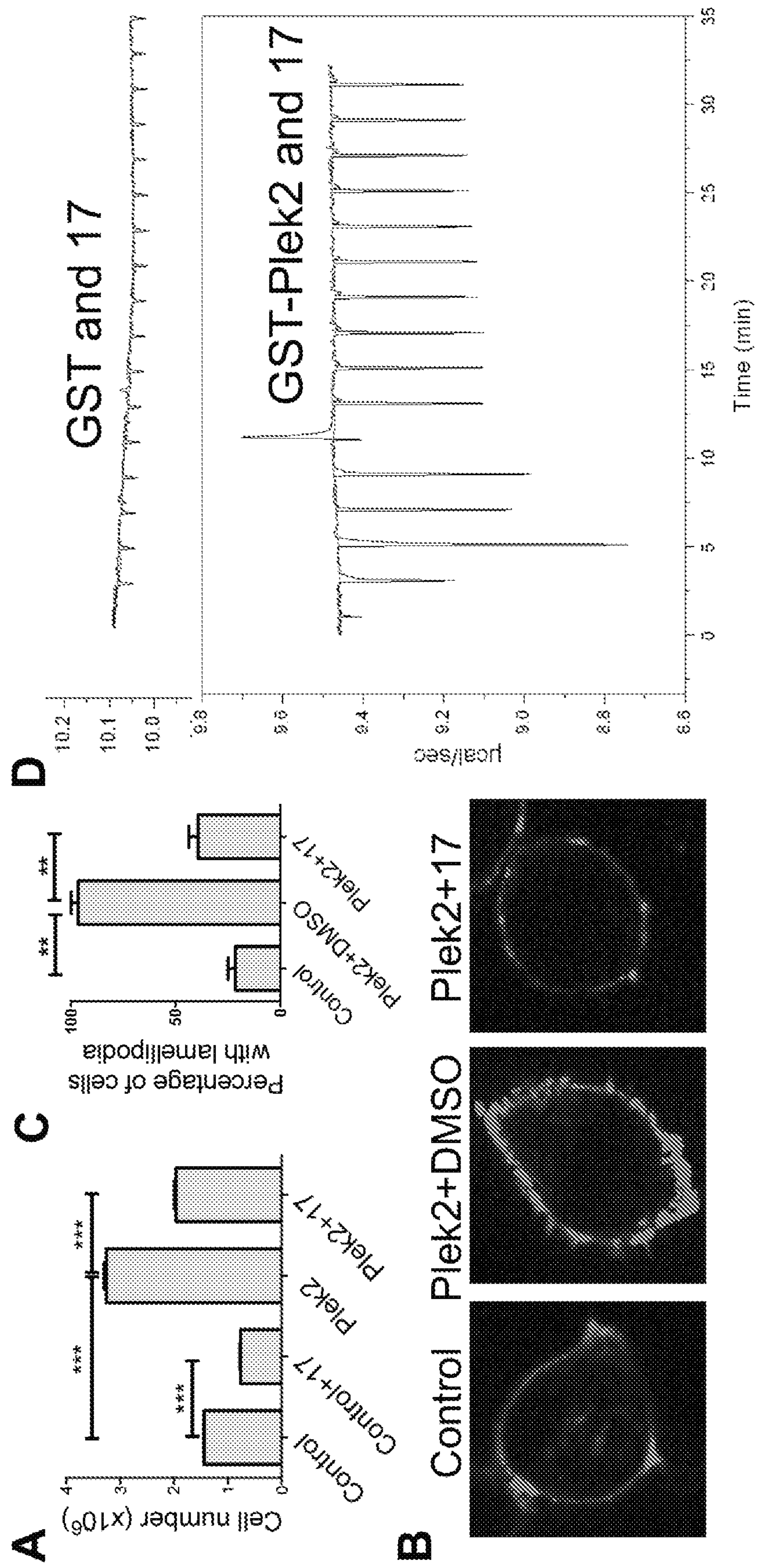
FIG. 4. NUP-17 directly targets and binds to Plek2. (A) Plek2 was overexpressed in mouse fetal liver Ter119 negative erythroblasts. NUP-17 (40 μM) were added in the control cells and Plek2 overexpressed cells. Cell number was calculated 48 hours after culture. (B) Plek2 was overexpressed in Cos-7 cells. Phalloidin 647 was used to stain actin in the indicated cells. 10 μM of NUP-17 was used. (C) Quantitative analysis of B. (D) ITC experiments using the microCal ITC200 instrument. 200 μM NUP-17 was titrated into a solution of 20 μM GST control or GST-Plek2. *P<0.05; *** P<0.001. 17 represents NUP-17.

To confirm that the inhibitory effect of NUP-17 on the proliferation and differentiation of fetal liver erythroid cells is due to Plek2 binding, we overexpressed Plek2 in the fetal liver cells and treated the cells with NUP-17. Indeed, although the compound is effective, cells with Plek2 overexpression partially reverted the inhibitory effects by NUP-17 (FIG. 4A). In addition, we also overexpressed Plek2 in Cos-7 cells, which induced prominent lamellipodia formation as previously reported (13). NUP-17 dramatically reverted lamellipodia in Plek2 overexpressed cells (FIG. 4B-C). These results further support the direct inhibitory effect of NUP-17 on Plek2 function. More important, we performed a binding assay between NUP-17 and GST-tagged Plek2 using isothermal calorimetry (ITC) collaborating with the Keck Biophysics Facility of Northwestern University, which showed specific interaction between the compound and Plek2 (FIG. 4D).

Similarity searching identified eight (8) close analogs of NUP-17 to show that NUP-17 is not a singleton and that similar compounds can also bind to Plek2. NUP-17d showed strongly enhanced inhibition of Plek2 with IC50<10 μM in the fetal liver proliferation assay (FIG. 5A-B). We also performed the same lamellipodia formation assay in Plek2-overexpressed Cos-7 cells using NUP-17d and achieved more potent inhibition (FIG. 5C-D).

Figure 6:
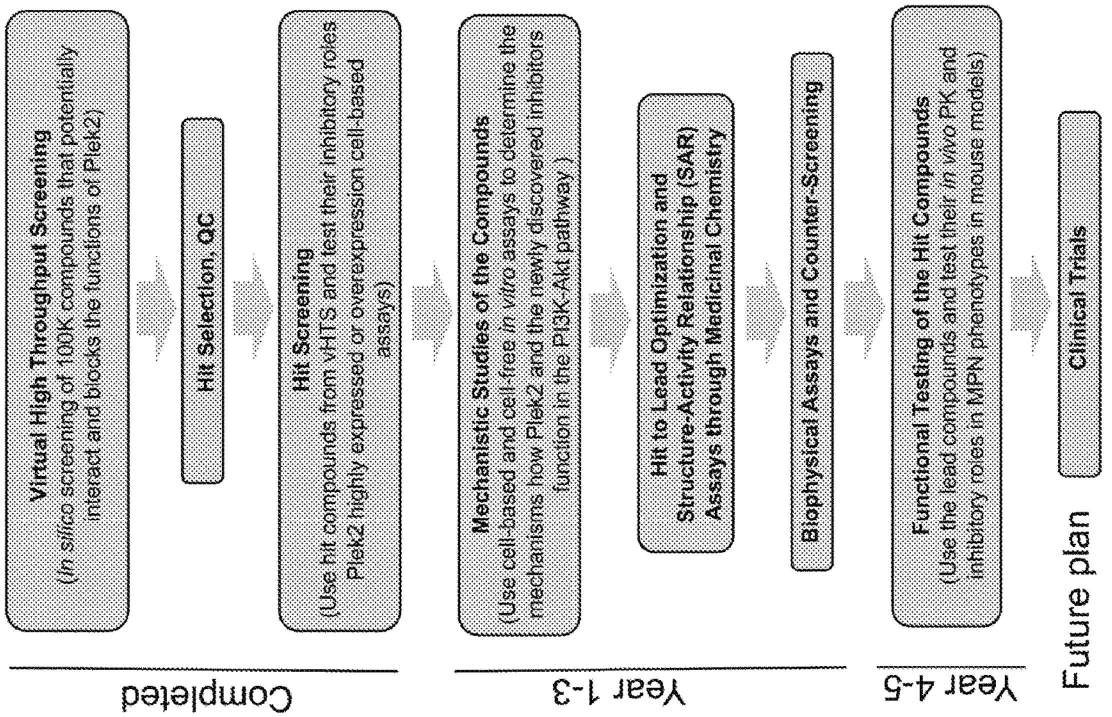
FIG. 6. Proposed screening, mechanistic study, and functional validation workflow.

The overall project plan and workflow is illustrated in FIG. 6. We have completed primary in silico vHTS, hit selection, quality control, hit screening using cell-based assays, and testing of new hit analogs. With these assays, we have obtained relatively potent NUP-17d in several in vitro assays and showed its specificity to Plek2. To reveal the mechanism of action of these compounds and further develop more potent inhibitors that can be used in the in vivo animal assays and future clinical trials, we will perform the rest of the steps in the workflow in the follow-up project. It is important to note that medicinal chemistry optimization will take place iteratively and closely integrated with our in vitro screening assays. Compounds meeting our criteria will advance to more relevant assays with the goal to produce compounds with robust in vitro efficacy.

Rationale and Preliminary Data. Plek2 is a lipid binding protein that has previously been suggested that both PH domains bear the motif to predict specificity for PI3K products (29). To define the lipid binding specificity of Plek2, we examined the ability of full-length protein to adhere to various phospholipids. We found that Plek2 displayed the highest binding to phosphoinositides that had phosphates in both the 3 and 4 positions (FIG. 7A). We next revealed that NUP-17 and NUP-17d did not disrupt Plek2-lipid binding (data not shown), which is expected since the targeting sequence of the compounds is the DEP domain. This result also suggests that the compounds are less likely to affect other PH domain containing proteins.

The binding of Plek2 to PtdIns(3,4)P2 suggests that Plek2 is a PI3K effector. To further determine the role of Plek2 in PI3K pathway, we overexpressed GFP-fusion Plek2 in Jurkat cells. GFP-Plek2 showed membrane as well as cytoplasmic distribution. When we treated the cells with PI3K inhibitor wortmannin, Plek2 cell membrane localization is significantly disrupted (FIG. 7B). We also purified bone marrow lineage negative cells from wild type and Plek2 knockout mice and treated the cells with erythropoietin to induce their differentiation to the erythroid cells. Erythropoietin significantly activated the PI3K pathway leading to the phosphorylation of Akt in the wild type cells. In contrast, the phosphorylated Akt is significantly decreased in Plek2 knockout cells (FIG. 7C). To directly test the effect of our hit compound, we added NUP-17d in Plek2 wild type bone marrow lineage negative cells treated with erythropoietin. Indeed, NUP-17d significantly inhibited phosphorylation of Akt (FIG. 7D).

These in vitro studies strongly indicate the critical roles of Plek2 in PI3K pathway. To test this in vivo and in a genetic approach, we crossed the Plek2 knockout mice with PTEN knockout to provide a proof-of-concept for the role of Plek2 in PI3K-Akt pathway. PTEN is a negative regulator of PI3K through the dephosphorylation of PI3K generated PtdIns(3,4,5)P3 to inhibit PI3K downstream Akt pathway. Loss of PTEN in the hematopoietic tissue in mice induces the activation of the PI3K pathway leading to a widely infiltrative myeloproliferative neoplasm to various organs and lethality around 40 days post-induced PTEN deletion (30). We crossed Plek2 knockout (KO) mice with Ptenfl/flMx-Cre mice and induced Pten deletion by polyinosinic:polycytidylic acid (poly-IC) injection. Strikingly, loss of Plek2 largely rescued the lethality in Ptenfl/flMx-Cre (FIG. 7E). The Ptenfl/flMx-Cre, Plek2 KO mice remained alive when this proposal was submitted. Histologic examinations of these mice indeed revealed significant amelioration of myelocyte infiltration to the lung (FIG. 7F), liver, and spleen (not shown). The bone marrow myeloproliferation was also significantly reduced (not shown).

Figure 8:
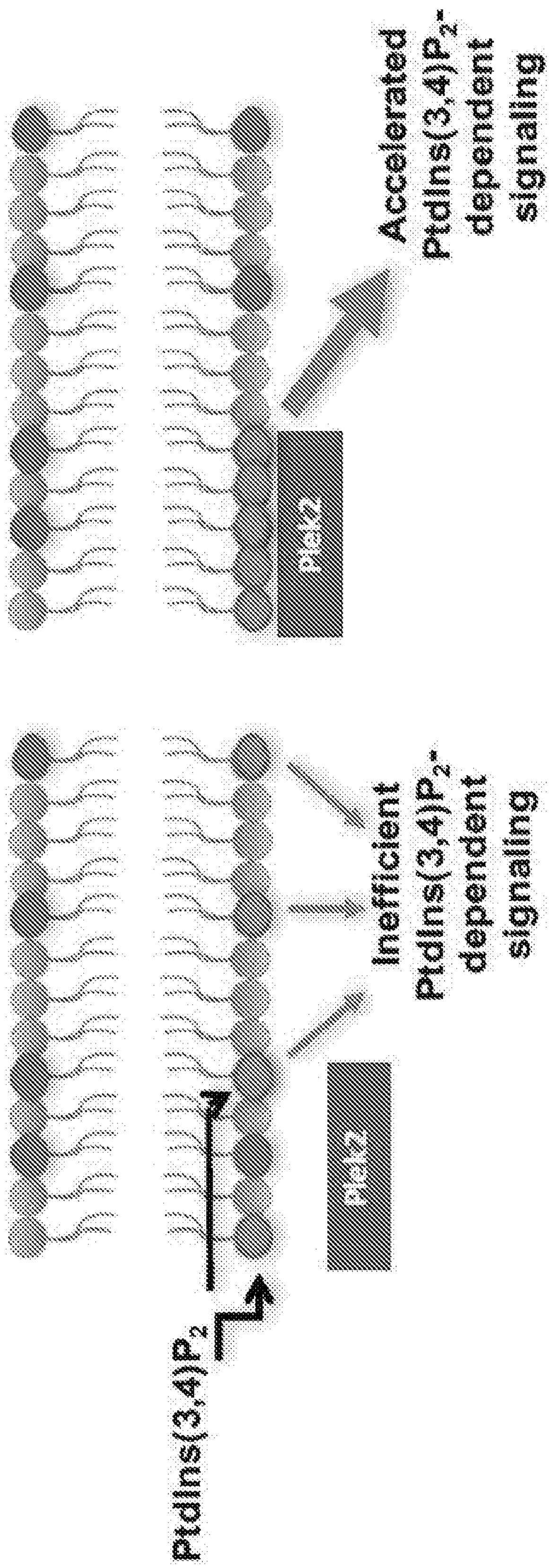
FIG. 8. Model of Plek2's function. In the absence of PtdIns(3,4)P2, Plek2 is located in the cytoplasm. Upon PI3K-mediated phosphorylation of phosphoinositides and generation of PtdIns(3,4)P2 on the inner leaflet of the cell membrane, Plek2 moves to the cell membrane and binds to multiple PtdIns(3,4)P2 molecules, thereby clustering this lipid and enhancing its ability to participate in signaling of the PI3K-Akt pathway.

Determination of the Extend by which Plek2 Regulations the Cellular Distribution of PtdIns(3,4)$P^2$. Previous studies have shown (31, 32) that hematopoietic cells contain discrete, non-communicating pools of phosphoinositides. Stabilization and modulation of these pools is likely to be very important for phosphoinositide function, and proteins that regulate the distribution of local pools of phosphoinositides are thought to be able to regulate signaling without affecting the overall cellular concentration of these lipids (33, 34). For example, gelsolin binds PtdIns(4,5)P2, and may physically alter its distribution within a membrane bilayer (35). The MARCKS protein is thought to have similar effects (34), and together with GAP43 and CAP23 belongs to a class of proteins called ‘PIPmodulins’ because they modulate phosphoinositides (36). These proteins are thought to sequester PtdIns(4,5)P2 in the plasma membrane, and they regulate phosphoinositide-mediated signaling (37, 38). We hypothesize that Plek2 plays a similar role as a PIPmodulin in that through its reported self-interaction as a homodimer (39), Plek2 promotes phosphoinositide clustering, which could also be facilitated through simple electrostatic effects as described before (34) (FIG. 8).

Figure 3:
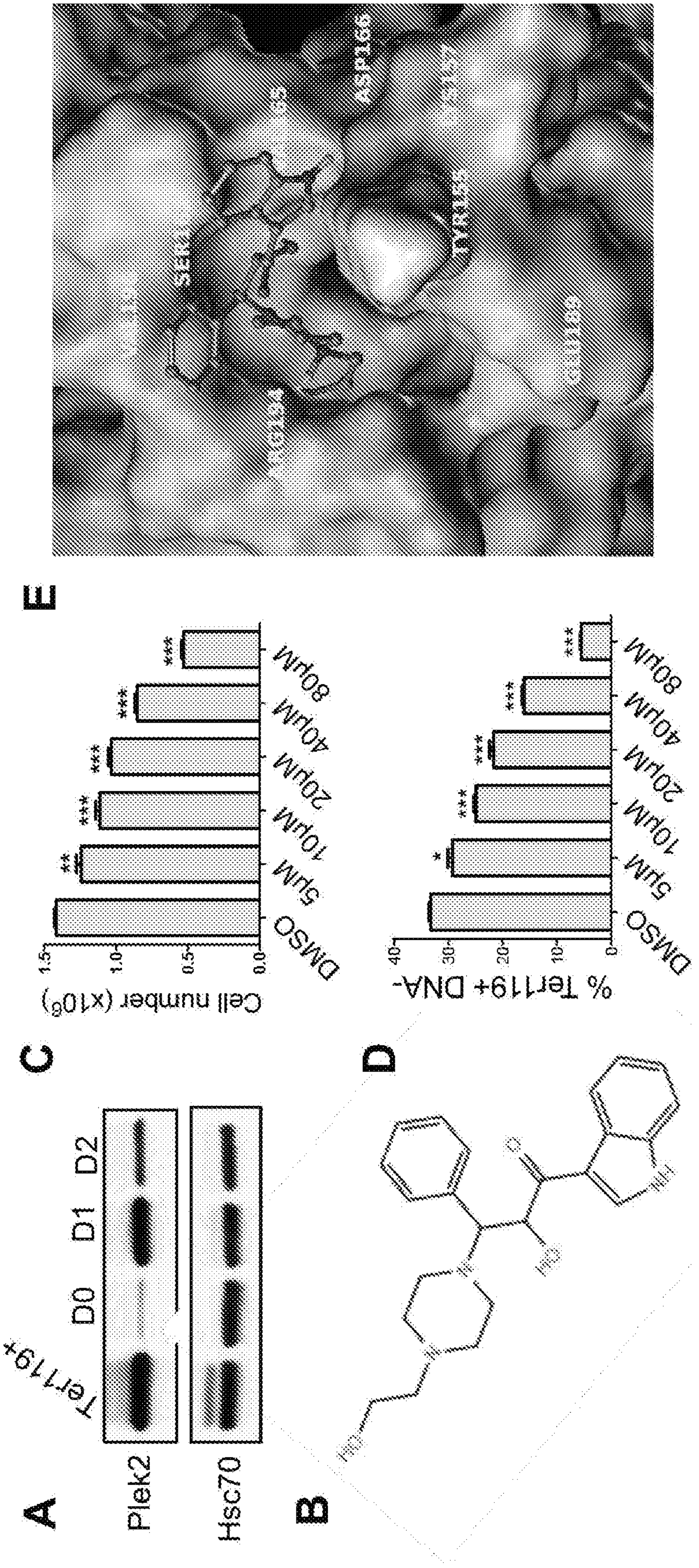
FIG. 3. NUP-17 inhibits Plek2 function in fetal liver erythropoiesis. (A) Mouse Ter119 (a mature erythroid cell marker) negative erythroblasts were purified and cultured for two days (D0-D2). The protein levels of Plek2 and Hsc70 loading control were analyzed by a Western blot assay. (B) The structure of NUP-17. (C-D) The proliferation and enucleation (DNA negative) profiles of cells from A treated with different concentration of NUP-17 for 48 hours. (E) Simulated Plek2 DEP domain interaction with NUP-17 using Schrodinger software. Amino acids that are potentially critical for the interaction are highlighted in yellow. *P<0.05;  P<0.01; * P<0.001.

To detect the intracellular localization of PtdIns(3,4)P2, retroviruses will be used to express GFP-tagged PH domains of TAPP1 and DAPP1 in the Ter119 negative erythroid progenitor cells treated with erythropoietin as in FIG. 3. In this case, fetal liver cells from wild type and Plek2 knockout mice will be used for comparison. The PH domains of TAPP1 and DAPP1 have quite different primary sequences, yet both have been well-characterized as specific PtdIns(3,4)P2-binding domains (37, 40). The strength in using these two different fluorescent probes is that the GFP-TAPP1 PH domain and the GFP-DAPP1 PH domain should give identical results if their distribution genuinely reflects the localization of PtdIns(3,4)P2. We will also perform the same experiment in erythropoietin-stimulated wild type fetal liver erythroblasts with NUP-17 and NUP-17d, as well as the optimized analogs we will obtain from the experiments described above. The IC50 levels of NUP-17 and NUP-17d will be used. We expect that the distribution of fluorescent PtdIns(3,4)P2 will be altered in Plek2 knockout cells and Plek2 inhibitor treated wild type cells. For comparison, we will also analyze whether Plek2 affects the localization of other phosphoinositides by using GFP probes that are specific for PtdIns(3,4,5)P3 (such as the PH domains of Grp1) (41) and PtdIns(4,5)P2 (such as the PH domains of *S. cerevisiae* Num1p) (42-44).

As we hypothesized, since NUP-17 and NUP-17d do not affect the lipid binding capacity of Plek2, the compounds likely disrupt Plek2 oligomerization through binding to the DEP domain. To test this, we have generated a Plek2 mutant with mutations of amino acids lysine 157, arginine 194, and aspartic acid 166 to alanine. These three amino acids were known to be critical for Plek2 function and are the predicted binding sites of the compounds (FIG. 3E). We will overexpress the mutant in Plek2 knockout fetal liver erythroblasts, which is expected to be unable to rescue the altered distribution of PtdIns(3,4)P2 in Plek2 null cells. Wild type Plek2 will be used as the positive control to transduce Plek2 knockout fetal liver erythroblasts.

Figure 9:
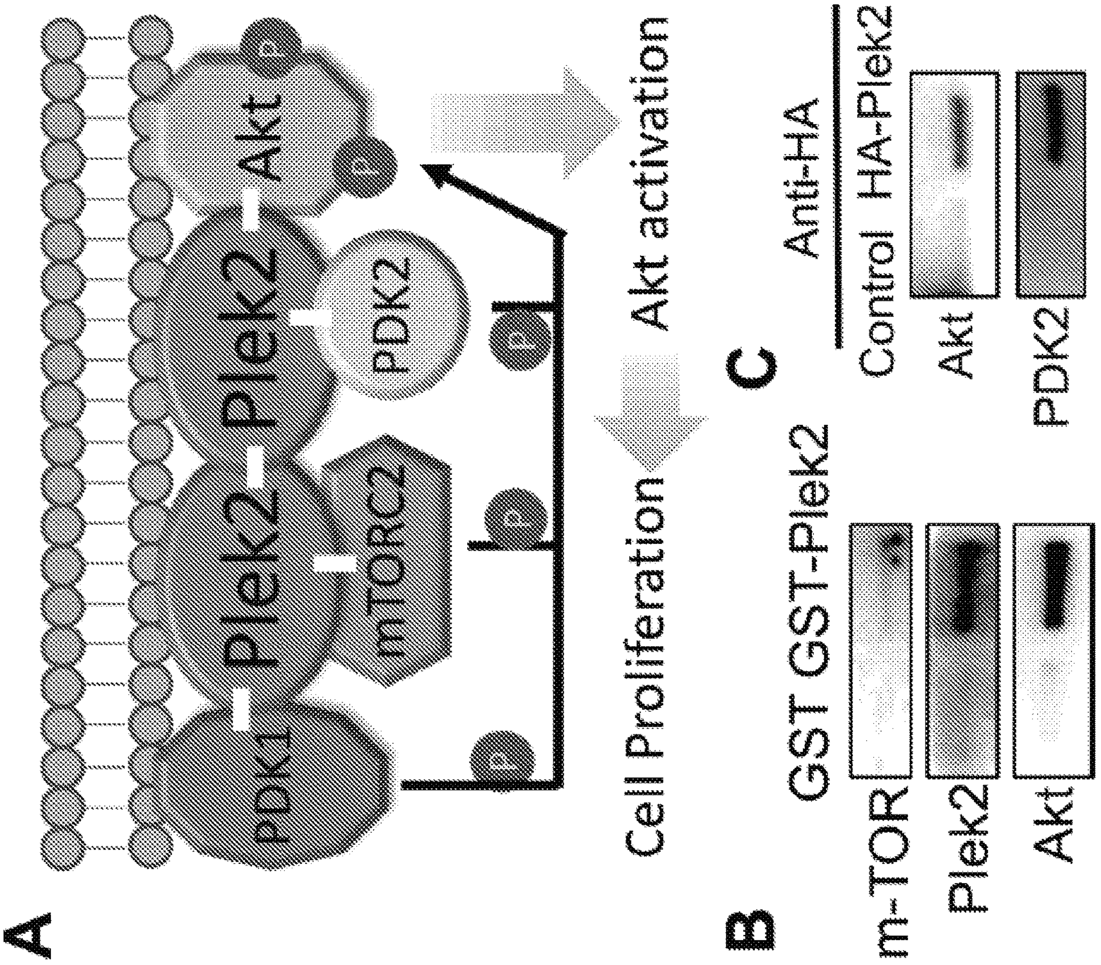
FIG. 9. Plek2 forms a membrane complex with PI3K effectors. (A) Schematic illustration of the recruitment of Akt, PDK1, PDK2, or mTORC2 by Plek2 to enhance PI3K signaling. White blocks indicate interaction and possible Plek2 inhibitor targeting sites. (B) GST pull-down assay of GSTPlek2 with Hela cell lysate. The binding of indicated proteins were detected by a Western blot assay. (C) Immunoprecipitation of HA tag with cell lysate from Hela cells transfected with HA-Plek2 followed by a Western blot assay of the indicated proteins.

Determination of the Roles of Plek2 and Plek2 Inhibitors in Akt Phosphorylation in vitro. In vitro cell-free assays will be important to specifically determine the role of Plek2 and our newly identified Plek2 inhibitors without concerns of off-target effects in vivo in the cells. In vitro assays are available to test Plek2 in clustering phosphoinositides as described in MARCKS and in other PIPmodulins. However, these assays do not directly reveal how Plek2 enhances the PI3K signaling through phosphorylation of Akt. PI3K phosphorylates PtdIns(4,5)P2 to generate PtdIns(3,4,5)P3, which is rapidly dephosphorylated to generate PtdIns(3,4)P2. The 3-phosphate group serves as a docking site on the plasma membrane for the PH domain of Akt, which partially activates Akt. Full activation of Akt requires membrane binding of PH domain containing kinase PDK1 and other kinases including PDK2 or mTORC2 complex to phosphorylate Akt. In the experiments described above, we will test the hypothesis that the compounds disrupt Plek2's PtdIns(3,4)P2 clustering ability. It is also possible that Plek2 interacts with Akt, PDK1, PDK2, or mTORC2 to influence the phosphorylation of Akt (FIG. 9A). Plek2 inhibitors would therefore block these interactions to inhibit the PI3K-Akt pathway. These two possibilities are not mutually exclusive in that the compounds could play dual roles to inhibit PI3K-Akt pathway through disruption of PtdIns(3,4)P2 clustering and Plek2's interactions with other proteins in the PI3K pathway.

To this end, we have performed GST pull down assays of GST-Plek2 with lysates from Hela cells that express high endogenous levels of Plek2, Akt, and mTOR. Indeed, Plek2 binds with itself and Akt with high affinity and relatively weakly with mTOR (FIG. 9B). In vivo co-immunoprecipitation (IP) assay also showed endogenous interaction of Plek2 with the complex (FIG. 9C). We will continue to test other proteins in the complex, including HA-Plek2 and mTOR or PDK1 endogenous binding. We will also perform the binding assays with recombinant Akt, PDK1, PDK2, and mTOR proteins in vitro to demonstrate their direct interaction. We hypothesize that the DEP domain will be critical for these bindings. To test this, we will use GST-Plek2 mutant with lysine 157, arginine 194, and aspartic acid 166 mutated to alanine as above. We expect that the mutant will not show similar interactions. With this information, we will test compounds NUP-17 and NUP-17d to determine the extent they abolish Plek2's interactions with any of these proteins. To ensure that the compounds are specific in blocking the interaction(s), in vitro binding assays using recombinant proteins will be used. To determine that the compounds are specific to Plek2, we will also perform ITC (FIG. 4D) to ensure that the compounds do not bind to these proteins. In addition, we will also determine whether the compounds can block Plek2-Plek2 self-interaction in an in vitro GST-pull down assay using GST-Plek2 and Flag-tagged Plek2 as previously reported (12, 45).

To directly assess the role of Plek2 in clustering phosphoinositide and phosphorylating Akt in vitro. We will perform an in vitro kinase assay (46). Recombinant Plek2 will be added (at ~0.1 nM) to vesicles of the desired composition that contain PtdIns(3,4)P2. The ability of this protein-lipid mixture to bind to PDK1, PDK2, or mTORC2, and to stimulate their in vitro kinase activity will be assessed by using Akt as the exogenous substrate. The results of these studies should allow us to reconcile the effects of Plek2 to affect PI3K signaling. If we are correct in our assumption, this finding will provide insight into the 'capacity' of Plek2 to serve as a phosphoinositide clustering and scaffolding protein for the activation of the PI3K-Akt signaling. We will then add different amount of compounds NUP-17 and NUP-17d in this in vitro kinase assay to determine whether they can inhibit Akt phosphorylation.

Figure 10:
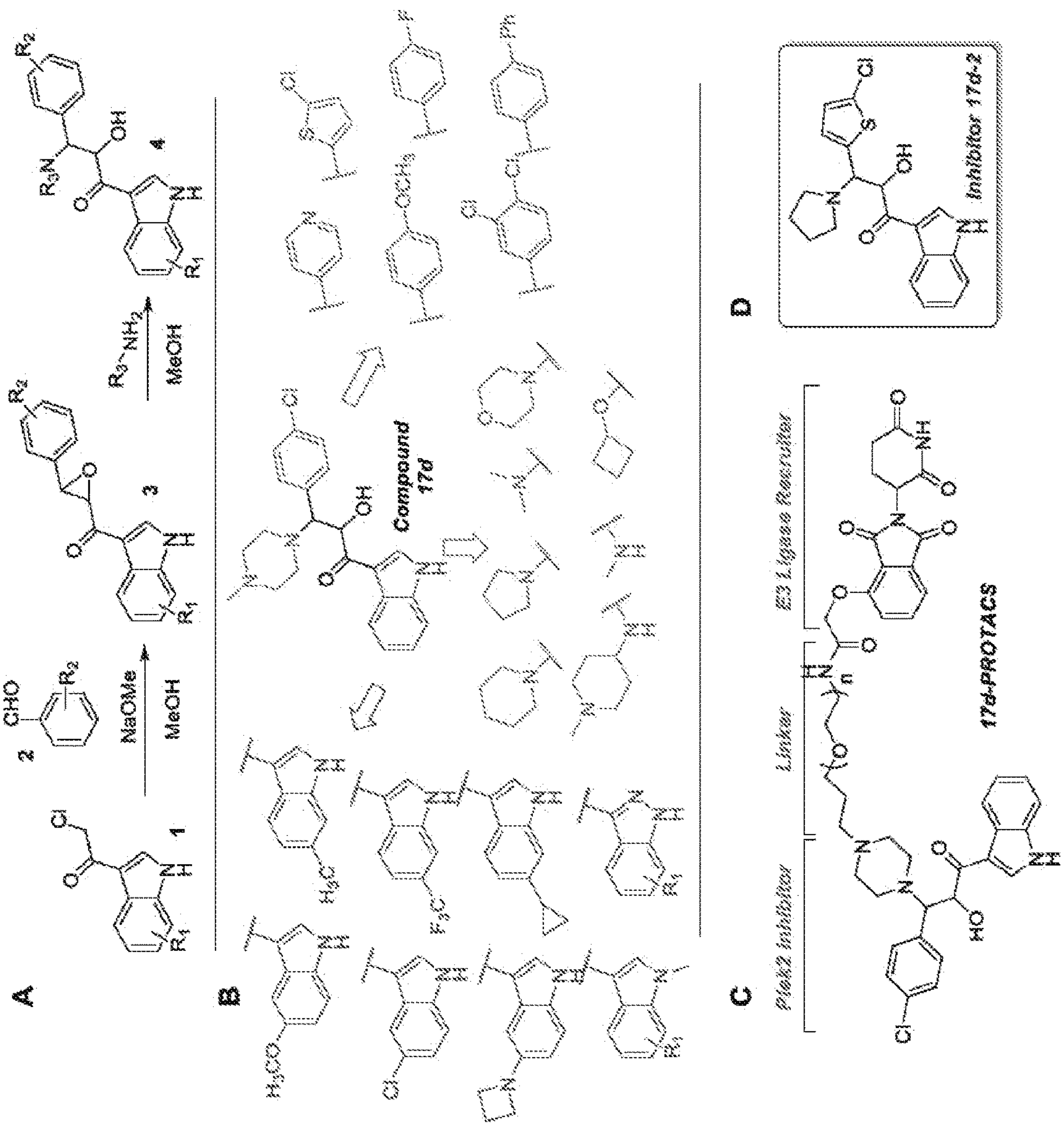
FIG. 10. Lead Optimization of Plek2 inhibitor NUP-17d. (A) Synthetic scheme used to prepare new analogs with diversification at all areas of the molecule. (B) Representative examples of new compounds to be prepared. (C) Structure of NUP-17d PROTACS to be synthesized, with variations envisioned in inhibitor, linker, and recruiter sections. (D) Structure of NUP-17d2.
Figure 11:
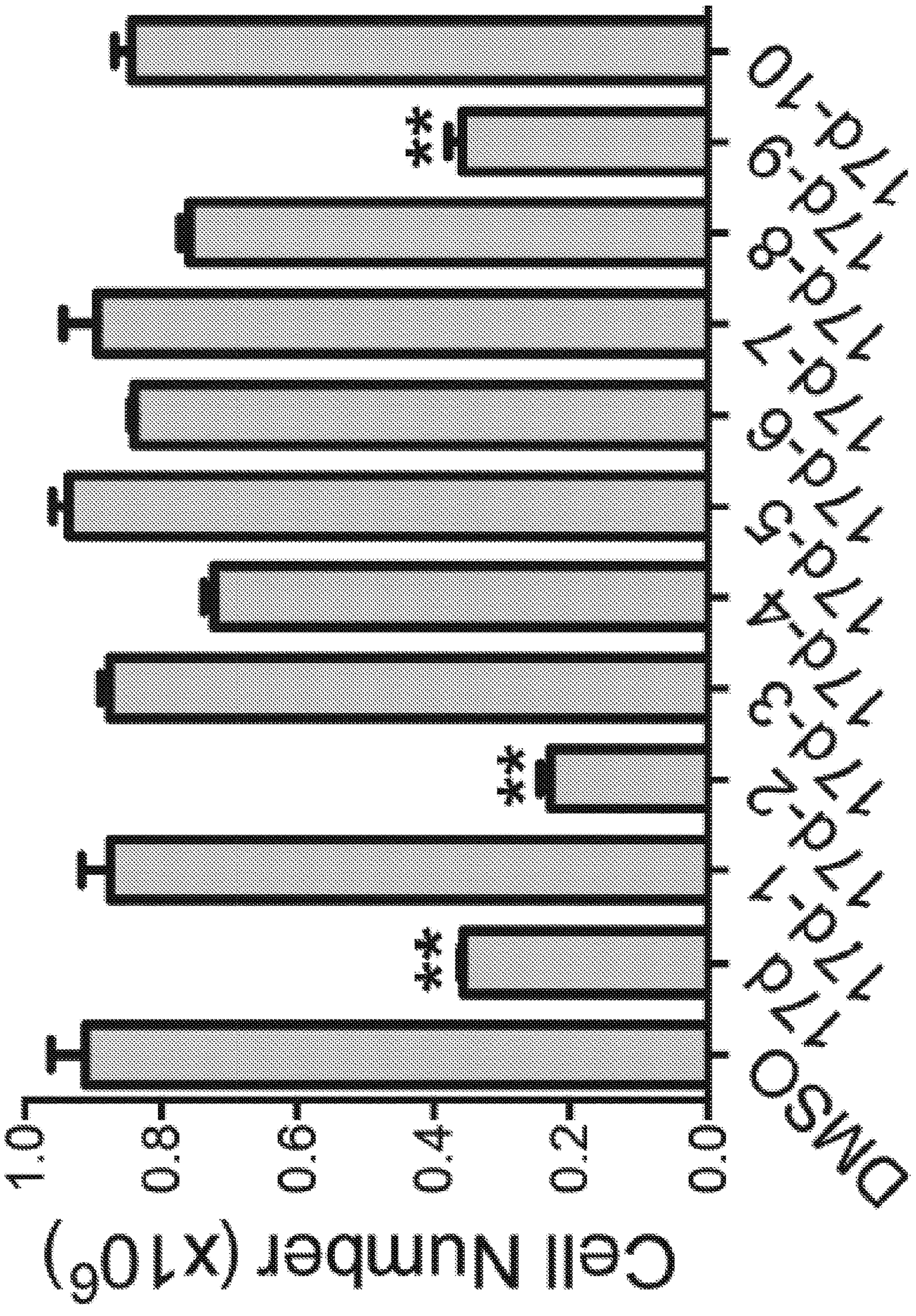
FIG. 11. Compound NUP-17d2 shows increased potency. Analogs of NUP-17d were analyzed for their effect on fetal liver erythroblast proliferation as in FIG. 3. 10 μM was used for each compound. ** P<0.01.

Lead Optimization Medicinal Chemistry. Compound NUP-17d will be used as the starting point in rational and iterative medicinal chemistry optimization. We have developed an efficient 2-step synthetic route to enable production of a wide variety of analogs (FIG. 10A). In our synthesis, commercial chloromethyl ketones (1) are reacted with aldehydes and sodium methoxide to produce the intermediate epoxide (3). Opening the epoxide with diverse amines gives the final compounds (4). This route has allowed us to synthesize ~20 new analogs so far in our initial hit-to-lead studies. We tested these new analogs and found compound NUP-17d-2 (FIG. 10D) to be more potent than 17d (FIG. 11). This analog will be further tested in cell-based and cell-free systems, as well as the binding and kinase assays.

We will build structure-activity relationships (SAR) by preparing new compounds with modifications at all major positions of the hit structure. Examples of new analogs are shown in FIG. 10B. These include substituents on the indole (e.g. methoxy, halogen, alkyl) to modify the steric and electronic nature of the ring system. We will also examine whether the indole N—H is necessary by making the N-Methyl derivative. Besides indole, we will also study different heterocyclic scaffolds such as indazole. The central amine position also allows for wide diversification, including pyrroldine, piperidine, morpholine, and other primary and secondary amines. We will also study whether the basic amine is necessary by preparing other potential hydrogen-bond acceptors such as ethers (as shown in FIG. 10B). The central ketone and hydroxyl groups will also be modified to determine if they are essential for activity. For instance, removal of the hydroxyl group or conversion to the methyl ether are potential analogs, and we may also reduce/remove the ketone to help define its role. Finally, a wide variety of aryl groups on the right-side can be introduced from readily available aldehyde precursors, and we will explore different hydrogen bond acceptor/donor combinations, and the effects of steric and lipophilic properties.

Synthesis will take place using parallel chemistry to increase synthetic throughput whenever possible. Each final compound will be purified using reverse-phase preparative HPLC to ensure high (i.e. >95%) purity. Inhibitors will be fully characterized using 1H- and 13C-NMR, HPLC, and MS, and our goal will be to produce 10-20 mg of each compound to support all initial in vitro studies. We anticipate synthesizing at least 100 new analogs per year to support lead optimization.

Designed compounds will be docked into our model (FIG. 3E) to assess their potential target binding using docked score, binding energy, and overall binding mode (using Schrodiner Glide). In addition, we will calculate the predicted physiochemical and ADME properties of proposed compounds to support the synthesis of compounds expected to possess more pharmaceutical-like characteristics. These parameters include C Log P, molecular weight, solubility, permeability, and microsomal stability. These will be calculated in both Biovia Pipeline Pilot and ACD/Labs Percepta for increased prediction accuracy and rigor.

Figure 5:
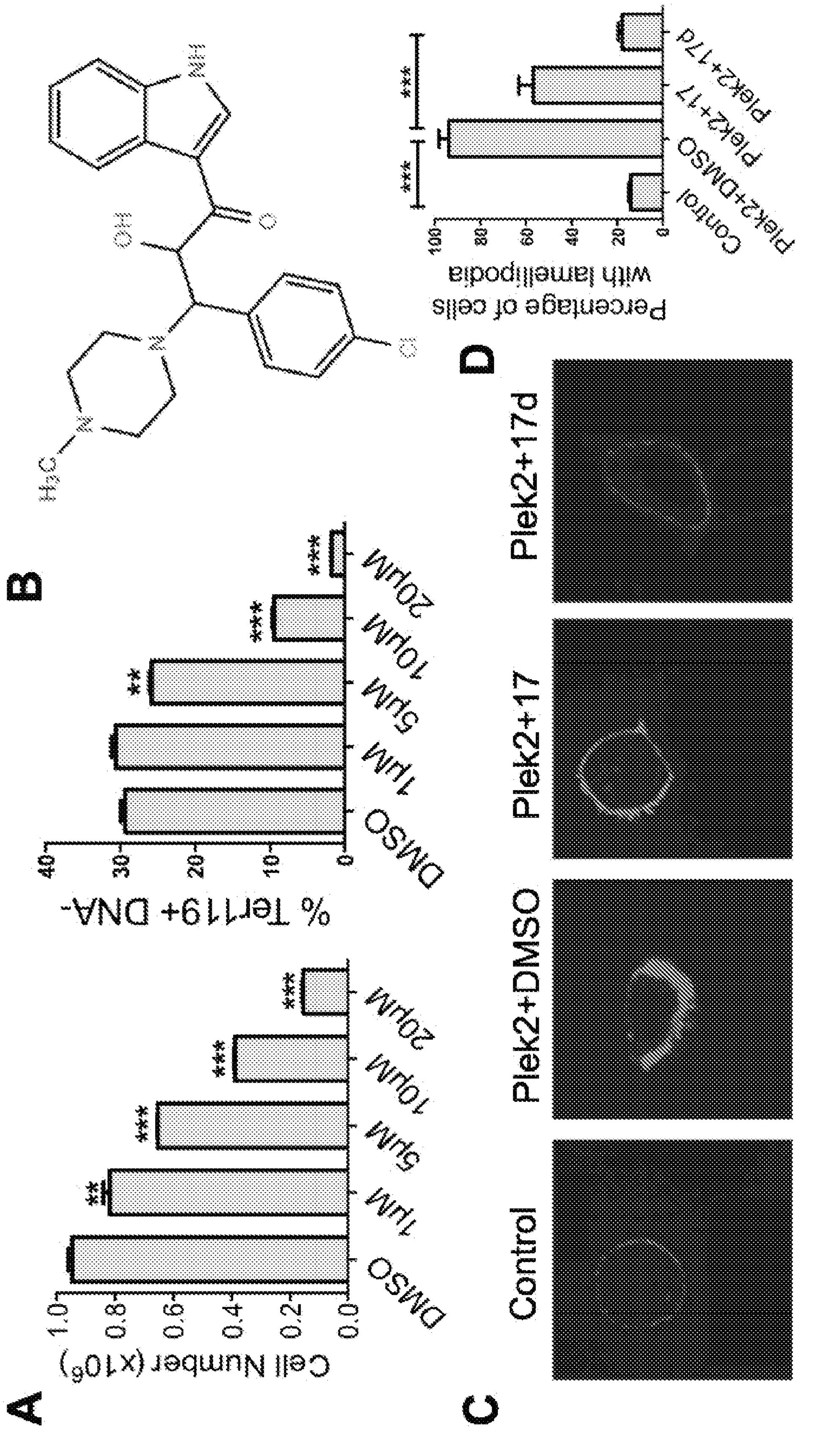
FIG. 5. Identification of a potent analog of NUP-17. (A) NUP-17d was analyzed for the inhibitory effects on fetal liver erythroblasts as in FIG. 3. Indicated doses were used. (B) The structure of NUP-17d. (C) Plek2 was overexpressed in Cos-7 cells. Phalloidin 647 was used to stain actin in the indicated cells. 10 μM of NUP-17 and NUP-17d were used. (D) Quantitative analysis of C. P<0.01; * P<0.001. 17 and 17d represent NUP-17 and NUP-17d, respectively.

Compounds with favorable results in our computational experiments will be prioritized for synthesis (see synthesis section above). Each new final compound will initially be screened in our cell-based functional assays of proliferation and enucleation (see FIG. 3). We will also use the in vitro cell-free binding and kinase assays to test the efficiency of the newly designed analogs. Inhibitors with IC50<10 μM in these assays will be advanced into secondary assays to measure their effects on fetal liver erythroid cells or Cos-7 cells that overexpress Plek2 to confirm Plek2-specificity (FIG. 5).

In addition to the design and synthesis of new NUP-17d analogs with improved potency as Plek2 inhibitors, we will also pursue the synthesis of compounds that can induce the degradation of Plek2 as another means by which to block the function of Plek2 in MPN. For this, we will prepare PROTACS (47-50) analogs of our lead compounds. While the approach described above focuses on reversible inhibitors of Plek2 function, the PROTACS strategy is complementary in that it leads to complete degradation of the protein and abolishes all of its functions. An example of the type of PROTACS we will prepare is shown in FIG. 10C. This bifunctional molecule will include one of our potent Plek2-binding molecules (e.g. compound NUP-17d) attached through a linker to a molecule that binds to, and recruits, an E3 ligase which will cause ubiquitination of Plek2 and subsequent degradation via the 20S proteasome. For this strategy, we will design and synthesize a number of different PROTACS derivatives to identify those that cause the most potent and effective Plek2 degradation. These analogs will vary in 1) the point of attachment onto the inhibitor (we will use the SAR generated above to help select the most appropriate derivatization points), 2) the chemistry of the attachment (e.g. alkyl, amide), 3) the type and length of linker (e.g. polyethyleglycol (PEG), alkyl, triazole), 4) the site and chemistry of attachment to the E3 ligand, and 5) the E3-recruiting ligand itself (e.g. VHL ligand, cereblon ligand). New PROTACS compounds will be tested in erythroid or Hela cell western blot to characterize PROTACS-induced degradation. Compounds will be tested at several different concentrations and multiple time points to ensure we accurately define the degradation.

Biophysical Assays and Counter-Screening. To confirm the interaction of the optimized compounds with Plek2, we will perform isothermal calorimetry (ITC) using the recombinant protein GST-Plek2 or Flag-tagged Plek2 we have produced. Specifically, MicroCal ITC200 instrument (GE Healthcare) with the jacket temperature will set at 25° C. The protein and our compound solutions will be prepared in PBS with 0.5% DMSO. Titrations of 200 μM compound into 20 μM GST-Plek2 solutions will be sufficient for 15 injections of 2.5 μl each with 120 seconds spacing between injections and a mixing speed at 900 rpm. An initial 0.1 μl injection will subsequently be removed during data analysis. A control experiment will be performed by titrating 200 μM compound into a solution of 20 μM GST. Heat signals obtained in this control experiment will be used to correct the ones observed in the compound-GST-Plek2 titration.

We will also perform counter screens to eliminate possible off-target effects of NUP-17d and the optimized compounds. As discussed above and shown in our data (FIG. 7), Akt is a direct target of Plek2 in the PI3K pathway. It is unlikely that our compounds directly target Akt since Akt does not contain a DEP domain. The compounds also do not affect the PH domain binding with phosphoinositides. However, to exclude this possibility whether the compound directly inhibit Akt phosphorylation, we will use the same in vitro kinase assay as described above but without the addition of recombinant Plek2. Akt will be phosphorylated by PDK1, PDK2, or mTORC2 in vitro, albeit at a lower level than the assay with the addition of Plek2. We expect that the addition of the compounds will not affect Akt phosphorylation by PDK1, PDK2, or mTORC2.

Additional counter-screenings also include direct binding of the compounds to other DEP domain containing proteins. While this is unlikely since the three critical amino acids (FIG. 3E) that our compounds bind to are quite specific to Plek2, we will confirm that no additional proteins bind to the compounds. To this end, we have started generating biotin labeled compound NUP-17d that will be used in a pull-down assay. The biotinylated compound will be applied to Hela or erythroid cell lysate and streptavidin beads will be added. The biotinylated compound streptavidin-protein complex will first be confirmed by a Western blot assay for the presence of Plek2. The complex will then be applied to a mass spectrometry assay to determine whether additional proteins are present.

Figure 12:
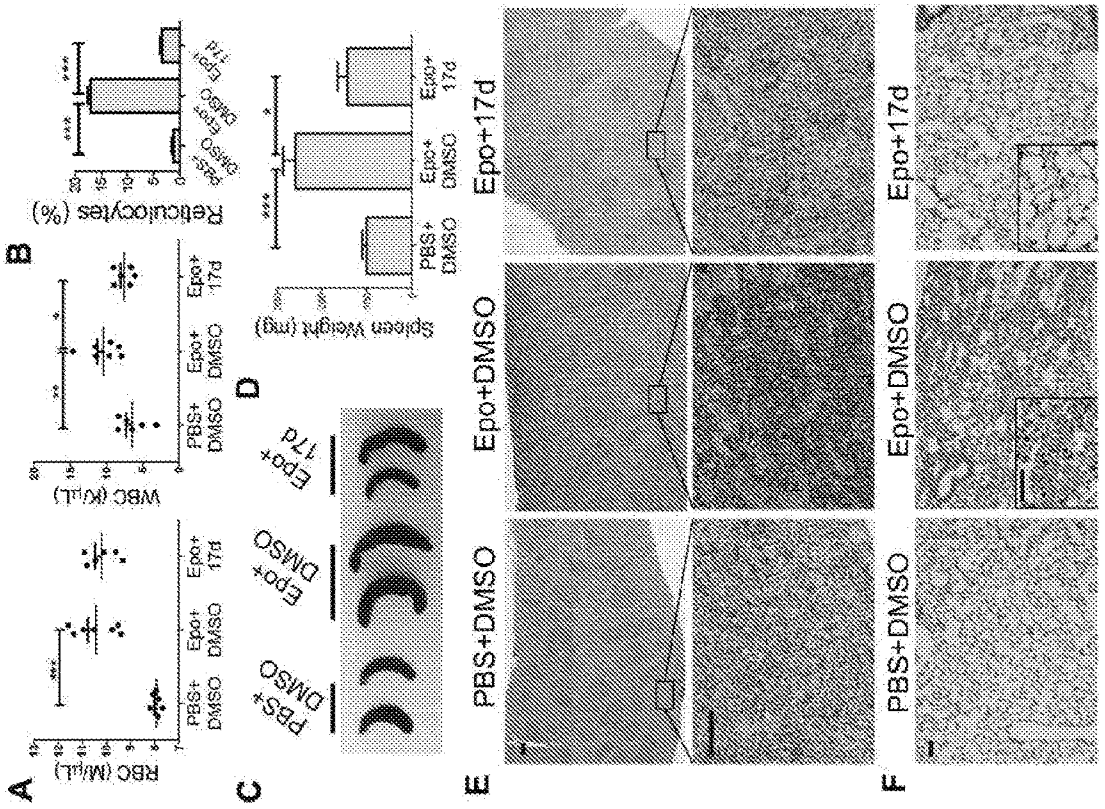
FIG. 12. NUP-17d ameliorates Erythropoietin-induced myeloproliferation. (A) RBC and WBC counts of indicated mice 3 weeks after Epo injection. Epo was dissolved in PBS. NUP-17d was dissolved in DMSO. N=5 in each group. (B) Quantitative analysis of reticulocyte count in indicated mice. N=5 in each group. (C) Representative pictures of the spleens from the indicated mice. (D) Quantitative analysis of C. N=5 in each group. (E) Hematoxylin and eosin stain of representative spleens from indicated mice. (F) Hematoxylin and eosin stain of lung sections. Inserted panels with high magnification reveal vascular occlusions. Scale bars: 100 μm. *P<0.05;  P<0.01; * P<0.001. 17d represents NUP-17d.

Determination of Lead Compound Toxicity. Compounds that possess desired bioactivity and in vitro metabolism/absorption as discussed above will be studied here. In these studies, we will establish a single dose 'No-Observed-Adverse-Effect-Level (NOAEL)' for our compounds in exploratory studies using only wild type mice. We will perform a rising dose acute toxicology study starting at 25 mg/kg (6 mice per compound, repeated at up to 6 concentrations) and follow each animal for 48 hours following a single intraperitoneal (IP) dose for evidence of acute toxicity. The dose will be escalated or decreased until a NOAEL is defined based on clinical observations. Terminal blood samples will be obtained and analyzed for complete blood count and chemistry. The NOAEL will be used to determine the highest dose for PK testing. Preliminary studies with compound NUP-17d (FIG. 12 see details below) showed that the inhibitor was well-tolerated for 2 days at 40 mg/kg and therefore, we anticipate that the analogs will also be tolerated at similar doses. Toxicity will be determined by standard criteria: hunched posture, lack of grooming, failure to thrive, failure to eat and drink, loss of 15-20% body weight, loss of righting reflex. Subsequent studies will use daily dosing for 5 days testing 2-3 dose levels (cohorts of 3-5 mice) selected from the single dose acute toxicity study and considering PK data.

Pharmacokinetic (PK) Assessment. PK studies using the highest safe dose will be conducted on lead compounds that were functionally validated and for which a single dose NOAEL could be established (above). While IP dosing may not be the preferred route of administration for an eventual MPN drug, these studies using IP dosing will give us data on many PK parameters, including bioavailability, which will be useful in prioritizing and triaging optimized compounds for testing using other routes, e.g., oral. PK parameters will be determined including Cmax, Tmax, VdSS, ClE, AUC, t, and oral bioavailability (% F) will be obtained (with the inclusion of an intravenous dosed cohort). These data will determine if the plasma concentrations are sufficient to provide satisfactory data in animals in the efficacy studies and to determine appropriate doses and dosing schedules for promising compounds. Our goal is to optimize NUP-17d-2 to have a plasma AUC>5× its cell viability EC50, a t½>2 hrs, and low-to-moderate clearance. Toxicology and pathology measures will be performed only after anti-tumor activity of lead compounds will be determined, if compounds are found worthy of detailed study based on MPN efficacy data. This approach will maximize use of animals and resources. In brief, complete blood counts will be obtained; selected organs and tissues (bone marrow, spleen, lung, liver, kidney) will be harvested.

Erythropoietin injection mouse model. We propose to test the compounds disclosed herein in MPN mouse models. However, we first tested the our lead compound in an erythropoietin (Epo) injection mouse model since it takes significantly less time (3 weeks) to determine the effects of the compounds in vivo. Our recently published work using this model demonstrated that repeated injection of Epo induced erythrocytosis, splenomegaly, and vascular occlusions in wild-type mice (15). In contrast, these phenotypes were significantly ameliorated when the same Epo injections were performed in Plek2 knockout mice (15). With the same system, we injected Epo in wild-type mice at 5,000 U/kg every 2 days for 2 weeks, and compound NUP-17d one week after Epo injection at 40 mg/kg every 2 days for 8 days. The mice were sacrificed after 3 weeks to determine their complete blood count, spleen size, and vascular occlusion.

Indeed, although NUP-17d did not significantly reduce the red blood cell count, which was also seen with the Plek2 knockout mice (15), the compound significantly reduced Epo-induced leukocytosis (FIG. 12A), reticulocytosis (FIG. 12B), splenomegaly (FIG. 12C-E), and vascular occlusions (FIG. 12F). Histologic examinations show that NUP-17d markedly ameliorated Epo-induced erythrocytosis in spleen red pulp (FIG. 12E) and lung vasculature (FIG. 12F). Importantly, NUP-17d-treated mice showed no hematologic or other abnormalities during the experiments. These data provide a proof-of-concept that our lead compound is effective in treating myeloproliferation, and form the basis for further in vivo investigation.

Figure 7:
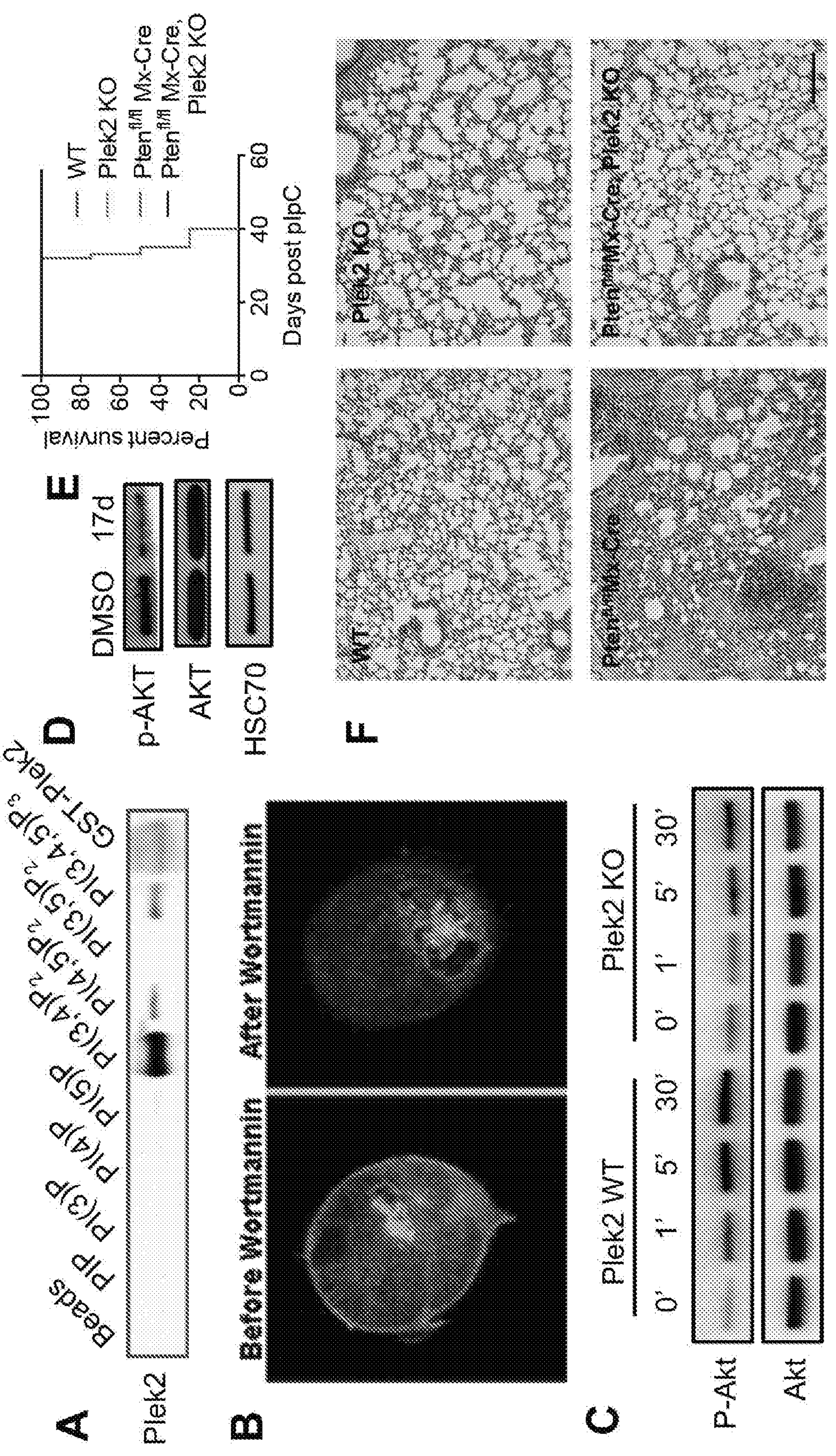
FIG. 7. Plek2 binds to PtdIns(3,4)P2 and is critical for the PI3K signaling pathway. (A) Plek2 shows strong affinity for PtdIns(3,4)P2 using a protein-lipid overlay assay. (B) Plek2 membrane association and cell spreading are PI3K dependent. Jurkat cells expressing GFP fused to the amino-terminus of wild-type Plek2 were plated on fibronectin. Real-time confocal imaging of live cells was performed. Shown is a cell expressing Plek2 before and after inhibition of PI3K with 100 nM wortmannin. (C) Bone marrow lineage negative cells from the indicated mice were treated with 2 units erythropoietin for the indicated amount of time (minutes). The level of Phospho-Akt and total Akt were analysis by Western blot assays. (D) Same as C except wild type bone marrow cells were used. 10 μM NUP-17d was used. The levels of the indicated proteins were analyzed by Western blot assays. (E) Kaplan-Meier survival analysis of indicated mice. Ptenfl/fl mice were crossed with Mx-Cre and Plek2 whole body knockout mice. The deletion of Pten in the hematopoietic tissues was induced by poly-IC injection. N=5 in each group. P=0.0067 between Ptenfl/flMx-Cre and Ptenfl/flMx-Cre, Plek2 KO. (F) Hematoxylin and eosin stain of the lungs from representative mice in E. Scale bar: 100 μm.
Figure 13:
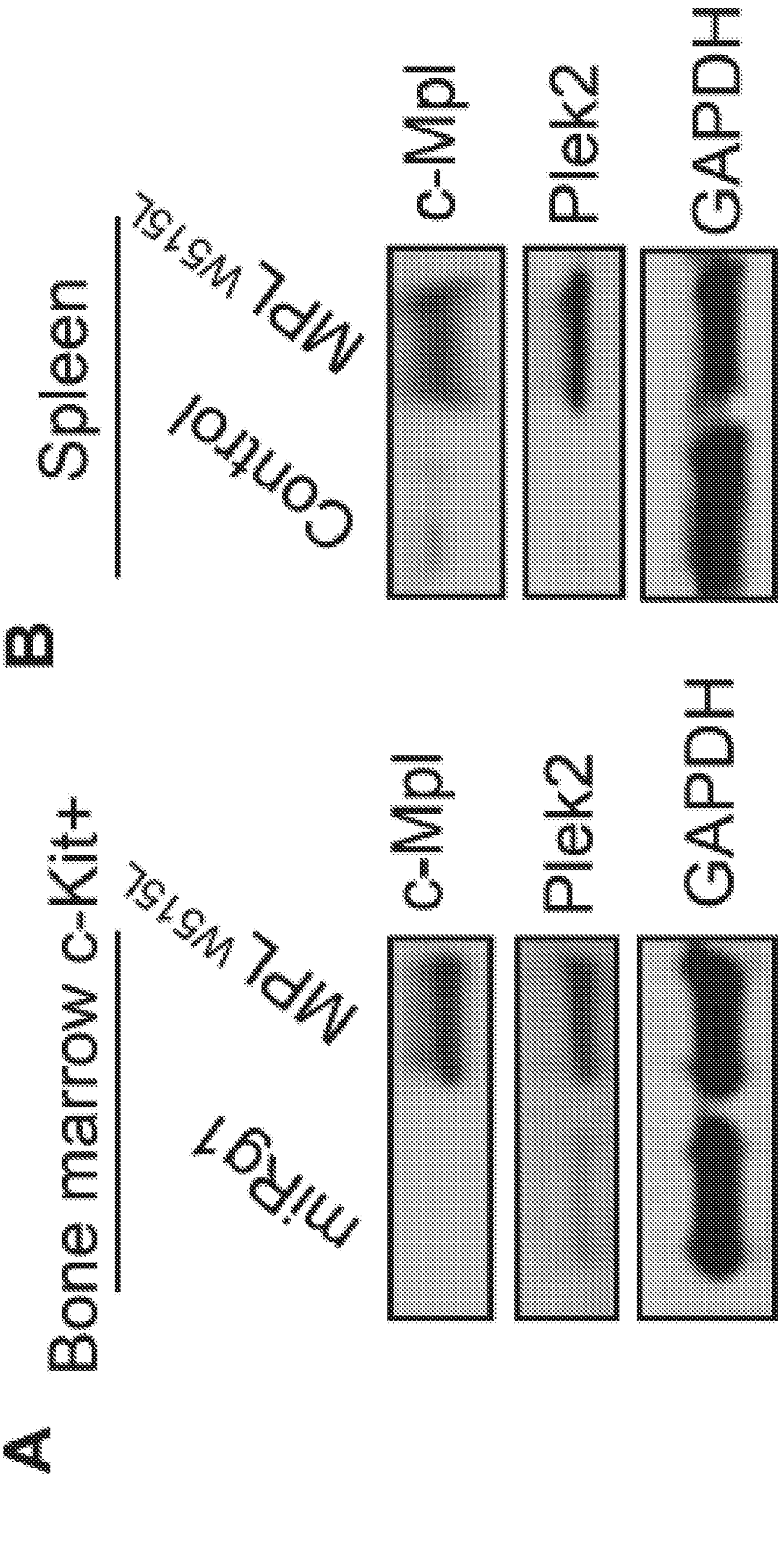
FIG. 13. Plek2 is upregulated by MPLW515L. (A) Western blot assay of Plek2 in bone marrow c-Kit+ cells transduced with MPLW515L and vector control. (B) Western blot assay of Plek2 from spleen cells of mice transplanted with MPLW515L transduced c-Kit+ bone marrow cells. GAPDH was used as a loading control.

In vivo MPN Mouse Models. The MPN mouse models we plan to use include a JAK2V617F knock-in model (FIG. 2), mouse transplantation models of bone marrow cells transduced with MPL or CALR mutants, and Ptenfl/flMx-Cre model (FIG. 7). Mutations in MPL and CALR represent the other two major causes Ph-negative MPNs. MPL functions physiologically as the thrombopoietin (Tpo) receptor and requires JAK2 to mediate its signaling. MPLW515L is one of the most common mutations and leads to receptor activation independent of Tpo (52). MPL mutations are commonly seen in ET and PMF. A mouse transplantation model using MPLW515L transduced bone marrow cells recapitulates human MPNs including myelofibrosis (53). Mutations in CALR are also commonly seen in patients with ET and PMF. More recent studies reveal that MPL is required for mutant CALR-driven transformation through JAK2-STAT pathway activation. (17, 20). These studies underscore the significance of JAK2-STAT pathway in the pathogenesis of Ph-negative MPNs, which is also confirmed by gene expression profiling data (17, 54). Therefore, it is very likely that Plek2 could also be involved in the pathogenesis of MPL and CALR mutation-driven MPNs. As expected, Plek2 protein levels were significantly upregulated in MPLW515L in vitro transduced bone marrow cells (FIG. 13A) and the spleen cells from mice transplanted with MPLW515L expressing bone marrows (FIG. 13B).

We will first test the optimized analogs of NUP-17d obtained in the experiments described above in the JAK2V617F knockin mouse model based on the PK information obtained in the experiments described above. JAK inhibitor ruxolitinib will be used as a positive control and the control for the measurement of toxicity. DMSO will be used as the negative control. The in vitro IC50, dosages used for NUP-17d (FIG. 12) and ruxolitinib, as well as dosages used in the experiments described above will be considered to determine the optimal dosage and dosing schedule of the Plek2 inhibitors to treat JAK2V617F mice. With this information, we will inject the optimized lead compound retroperitoneally in JAK2V617F MPN mice. The complete blood count every other week and survival will be monitored. The bone marrow and spleen from these mice will be analyzed to determine whether the lead compounds could revert the activated JAK2-STAT5-induced myeloproliferative phenotypes such as hypercellular bone marrow, increased megakaryocytes, granulocytic and erythroid hyperplasia, splenomegaly, and thrombosis (vascular occlusions) at the completion of these injections and when the DMSO control mice start to show phenotype and lethality. With the success of compound NUP-17d in the in vitro and in vivo studies, a critical measure of success here is to demonstrate that the lead compounds show minimal side effects (compared to ruxolitinib) but significant rescue of JAK2V617F MPN mice.

We will also determine the effect of our lead compounds in MPLW515L and CALR mutant-induced MPNs. The most studied model with these two mutants is bone marrow transplantation. We will first purify the lineage negative, c-Kit positive bone marrow stem/progenitor cells (HSPCs) from wild type mice. These cells will be transduced with lentiviruses expressing wild-type MPL, MPLW515L mutant, or vector control. The cells ($5\times10^5$, CD45.2+) will then be transplanted into lethally irradiated recipient mice together with wild-type supporting cells ($5\times10^6$, CD45.1+). Similar to JAK2V617F mutation, transplantation of bone marrow cells expressing MPLW515L is known to be able to induce MPN phenotypes in the recipient mice, which include erythrocytosis, leukocytosis, thrombocytosis, and splenomegaly (53). These phenotypes initiate around one month after transplantation and progressively become worse. We will treat the mice one month after transplantation with our optimized analogs with doses and dosing schedule similar to what we discussed in JAK2V617F mice above. As a positive control, we will also perform transplantation of mice with mutant-transduced HSPCs from Plek2 knockout mice. Vascular occlusions and lethality in MPLW515L model will be analyzed. In contrast to the JAK2V617F knockin mouse model, mice transplanted with bone marrow cells expressing MPLW515L exhibit prominent myelofibrosis (53). Therefore, we will also investigate whether the optimized analogs would ameliorate fibrosis in the bone marrow and spleen, through reticulin stain. We expect that treatment of Plek2 inhibitors will significantly ameliorate the phenotypes in mice transplanted with HSPCs expressing MPLW515L.

The CALR mutant contains abundant positively charged amino acid and binds to MPL to induce MPL-dependent myeloproliferative phenotypes (20). Similar to the MPLW515L model, we will transplant the lethally irradiated mice with HSPCs transduced with wild-type human CALR, or a CALRMUT. These mice will also be treated with the optimized analogs similar to the MPLW515L model. CALRMUT-expressing mice develop megakaryocytic lineage-specific MPN phenotypes including isolated thrombocytosis and megakaryocytic hyperplasia with hyper-lobated nuclei and emperipolesis, which are MPL dependent (13). Since Plek2 is also downstream of the MPL signaling involving JAK2-STAT pathway, and mitigated the megakaryocytic phenotypes in JAK2V617F mice (FIG. 2), we expect that treatment of Plek2 inhibitors would ameliorate thrombocytosis and megakaryocytic hyperplasia.

Importantly, the MPL and CALR mutant transplantation model will enable us to determine whether our lead compound will reduce the allele frequency of the mutant clones after extended period of treatment. In this respect, we will use flow cytometry or PCR to analyze the peripheral white blood cells periodically to determine the percentage of mutant clones (CD45.2+) compared to the normal ones (supporting cells during transplant, CD45.1+). Given this significance, transplantation model using JAK2V617F will also be performed. Equally important, the long-term treatment with our compound will reveal whether there is a chronic toxicity to the mice as the JAK inhibitors. In these experiments, JAK inhibitor will be used as the positive control and the control for toxicity analysis.

We will also use the Ptenfl/flMx-Cre model to test our lead compounds. While PTEN is not commonly mutated in patients with MPNs, the activation of the PI3K-Akt pathway is known to be involved in the pathogenesis of MPN (21-23). Our proof-of-principle mouse genetic study in FIG. 7 validated the critical role of Plek2 in PI3K-Akt pathway. Therefore, treating mice with Pten-deficiency-induced MPNs with our lead compounds will directly test their mechanism of action in vivo. We will treat the Ptenfl/flMx-Cre mice with our optimized analogs 10-20 days after poly-IC injection with the dosing and dosing schedules similar as above. We will then determine whether the compounds will rescue or delay the lethality of these mice. One of the advantages of the Ptenfl/flMx-Cre model, compared to the JAK2V617F knockin model and the MPL, CALR mutant transplantation models, is that these mice die of the disease fairly quickly in approximately 40 days (FIG. 7E). Therefore, we will be able to adjust the dosage to be able to observe the rescue phenotype within a short period. As shown in FIG. 7F, Ptenfl/flMx-Cre mice after poly-IC injection developed prominent myeloproliferation with widespread organ infiltration. We will also determine whether our optimized analogs will reduce myeloid cell organ infiltration and myeloproliferation in the bone marrow in these mice.

REFERENCES

1. Levine R L, Wadleigh M, Cools J, Ebert B L, Wernig G, Huntly B J, Boggon T J, Wlodarska I, Clark J J, Moore S, Adelsperger J, Koo S, Lee J C, Gabriel S, Mercher T, D'Andrea A, Frohling S, Dohner K, Marynen P, Vandenberghe P, Mesa R A, Tefferi A, Griffin J D, Eck M J, Sellers W R, Meyerson M, Golub T R, Lee S J, Gilliland D G. Activating mutation in the tyrosine kinase JAK2 in polycythemia vera, essential thrombocythemia, and myeloid metaplasia with myelofibrosis. Cancer Cell. 2005; 7(4):387-97. Epub 2005 Apr. 20. doi: 10.1016/j.ccr.2005.03.023. PubMed PMID: 15837627.
2. Kralovics R, Passamonti F, Buser A S, Teo S S, Tiedt R, Passweg J R, Tichelli A, Cazzola M, Skoda R C. A gain-of-function mutation of JAK2 in myeloproliferative disorders. N Engl J Med. 2005; 352(17):1779-90. Epub 2005 Arp. 29. doi: 10.1056/NEJMoa051113. PubMed PMID: 15858187.

3. James C, Ugo V, Le Couedic J P, Staerk J, Delhommeau F, Lacout C, Garcon L, Raslova H, Berger R, Bennaceur-Griscelli A, Villeval J L, Constantinescu S N, Casadevall N, Vainchenker W. A unique clonal JAK2 mutation leading to constitutive signalling causes polycythaemia vera. Nature. 2005; 434(7037):1144-8. Epub 2005 Mar. 29. doi: 10.1038/nature03546. PubMed PMID: 15793561.
4. Baxter E J, Scott L M, Campbell P J, East C, Fourouclas N, Swanton S, Vassiliou G S, Bench A J, Boyd E M, Curtin N, Scott M A, Erber W N, Green A R, Cancer Genome P. Acquired mutation of the tyrosine kinase JAK2 in human myeloproliferative disorders. Lancet. 2005; 365(9464):1054-61. Epub 2005 Mar. 23. doi: 10.1016/50140-6736(05)71142-9. PubMed PMID: 15781101.
5. Kralovics R, Teo S S, Buser A S, Brutsche M, Tiedt R, Tichelli A, Passamonti F, Pietra D, Cazzola M, Skoda R C. Altered gene expression in myeloproliferative disorders correlates with activation of signaling by the V617F mutation of Jak2. Blood. 2005; 106(10):3374-6. Epub 2005 Aug. 6. doi: 10.1182/blood-2005-05-1889. PubMed PMID: 16081684.
6. Cervantes F, Vannucchi A M, Kiladjian J J, Al-Ali H K, Sirulnik A, Stalbovskaya V, McQuitty M, Hunter D S, Levy R S, Passamonti F, Barbui T, Barosi G, Harrison C N, Knoops L, Gisslinger H, investigators C-I. Three-year efficacy, safety, and survival findings from COMFORT-II, a phase 3 study comparing ruxolitinib with best available therapy for myelofibrosis. Blood. 2013; 122(25):4047-53. Epub 2013 Nov. 1. doi: 10.1182/blood-2013-02-485888. PubMed PMID: 24174625.
7. Sonbol M B, Firwana B, Zarzour A, Morad M, Rana V, Tiu R V. Comprehensive review of JAK inhibitors in myeloproliferative neoplasms. Ther Adv Hematol. 2013; 4(1):15-35. Epub 2013 Apr. 24. doi:10.1177/2040620712461047. PubMed PMID: 23610611; PMCID: PMC3629759.
8. Harrison C, Kiladjian J J, Al-Ali H K, Gisslinger H, Waltzman R, Stalbovskaya V, McQuitty M, Hunter D S, Levy R, Knoops L, Cervantes F, Vannucchi A M, Barbui T, Barosi G. JAK inhibition with ruxolitinib versus best available therapy for myelofibrosis. N Engl J Med. 2012; 366(9):787-98. Epub 2012 Mar. 2. doi: 10.1056/NEJMoa1110556. PubMed PMID: 22375970.
9. Koppikar P, Bhagwat N, Kilpivaara O, Manshouri T, Adli M, Hricik T, Liu F, Saunders L M, Mullally A, Abdel-Wahab O, Leung L, Weinstein A, Marubayashi S, Goel A, Gonen M, Estrov Z, Ebert B L, Chiosis G, Nimer S D, Bernstein B E, Verstovsek S, Levine R L. Heterodimeric JAK-STAT activation as a mechanism of persistence to JAK2 inhibitor therapy. Nature. 2012; 489(7414):155-9. Epub 2012 Jul. 24. doi: 10.1038/naturel 1303. PubMed PMID: 22820254; PMCID: PMC3991463.
10. Passamonti F, Maffioli M. The role of JAK2 inhibitors in MPNs 7 years after approval. Blood. 2018; 131(22):2426-35. Epub 2018 Apr. 14. doi: 10.1182/blood-2018-01-791491. PubMed PMID: 29650801.
11. Porpaczy E, Tripolt S, Hoelbl-Kovacic A, Gisslinger B, Bago-Horvath Z, Casanova-Hevia E, Clappier E, Decker T, Fajmann S, Fux D A, Greiner G, Gueltekin S, Heller G, Herkner H, Hoermann G, Kiladjian J J, Kolbe T, Komauth C, Krauth M T, Kralovics R, Muellauer L, Mueller M, Prchal-Murphy M, Putz E M, Raffoux E, Schiefer A I, Schmetterer K, Schneckenleithner C, Simonitsch-Klupp I, Skrabs C, Sperr W R, Staber P B, Strobl B, Valent P, Jaeger U, Gisslinger H, Sexl V. Aggressive B-cell lymphomas in patients with myelofibrosis receiving JAK1/2 inhibitor therapy. Blood. 2018. Epub 2018/06/17. doi: 10.1182/blood-2017-10-810739. PubMed PMID: 29907599.
12. Abrams C S, Zhang J, Downes C P, Tang X, Zhao W, Rittenhouse S E. Phosphopleckstrin inhibits gbetagamma-activable platelet phosphatidylinositol-4,5-bisphosphate 3-kinase. J Biol Chem. 1996; 271(41):25192-7. Epub 1996 Oct. 11. PubMed PMID: 8810277.
13. Hu M H, Bauman E M, Roll R L, Yeilding N, Abrams C S. Pleckstrin 2, a widely expressed paralog of pleckstrin involved in actin rearrangement. J Biol Chem. 1999; 274(31):21515-8. Epub 1999 Jul. 27. PubMed PMID: 10419454.
14. Bach T L, Kerr W T, Wang Y, Bauman E M, Kine P, Whiteman E L, Morgan R S, Williamson E K, Ostap E M, Burkhardt J K, Koretzky G A, Bimbaum M J, Abrams C S. PI3K regulates pleckstrin-2 in T-cell cytoskeletal reorganization. Blood. 2007; 109(3):1147-55. Epub 2006 Sep. 30. doi: 10.1182/blood-2006-02-001339. PubMed PMID: 17008542; PMCID: PMC1785144.
15. Zhao B, Mei Y, Cao L, Zhang J, Sumagin R, Yang J, Gao J, Schipma M J, Wang Y, Thorsheim C, Zhao L, Stalker T, Stein B, Wen Q J, Crispino J D, Abrams C S, Ji P. Loss of pleckstrin-2 reverts lethality and vascular occlusions in JAK2V617F-positive myeloproliferative neoplasms. J Clin Invest. 2018; 128(1):125-40. Epub 2017/12/05. doi: 10.1172/JC194518. PubMed PMID: 29202466.
16. Vannucchi A M, Harrison C N. Emerging treatments for classical myeloproliferative neoplasms. Blood. 2017; 129 (6):693-703. Epub 2016 Dec. 29. doi: 10.1182/blood-2016-10-695965. PubMed PMID: 28028027.
17. Rampal R, Al-Shahrour F, Abdel-Wahab O, Patel J P, Brunel J P, Mermel C H, Bass A J, Pretz J, Ahn J, Hricik T, Kilpivaara O, Wadleigh M, Busque L, Gilliland D G, Golub T R, Ebert B L, Levine R L. Integrated genomic analysis illustrates the central role of JAK-STAT pathway activation in myeloproliferative neoplasm pathogenesis. Blood. 2014; 123(22):e123-33. Epub 2014 Apr. 18. doi: 10.1182/blood-2014-02-554634. PubMed PMID: 24740812; PMCID: PMC4041169.
18. Tefferi A, Pardanani A. Myeloproliferative Neoplasms: A Contemporary Review. JAMA Oncol. 2015; 1(1):97-105. Epub 2015 Jul. 17. doi: 10.1001/jamaoncol.2015.89. PubMed PMID: 26182311.
19. Araki M, Yang Y, Masubuchi N, Hironaka Y, Takei H, Morishita S, Mizukami Y, Kan S, Shirane S, Edahiro Y, Sunami Y, Ohsaka A, Komatsu N. Activation of the thrombopoietin receptor by mutant calreticulin in CALR-mutant myeloproliferative neoplasms. Blood. 2016; 127 (10):1307-16. Epub 2016 Jan. 29. doi: 10.1182/blood-2015-09-671172. PubMed PMID: 26817954.
20. Elf S, Abdelfattah N S, Chen E, Perales-Paton J, Rosen E A, Ko A, Peisker F, Florescu N, Giannini S, Wolach O, Morgan E A, Tothova Z, Losman J A, Schneider R K, Al-Shahrour F, Mullally A. Mutant Calreticulin Requires Both Its Mutant C-terminus and the Thrombopoietin Receptor for Oncogenic Transformation. Cancer Discov. 2016; 6(4):368-81. Epub 2016 Mar. 10. doi: 10.1158/2159-8290.CD-15-1434. PubMed PMID: 26951227; PMCID: PMC4851866.
21. Bartalucci N, Guglielmelli P, Vannucchi A M. Rationale for targeting the PI3K/Akt/mTOR pathway in myeloproliferative neoplasms. Clin Lymphoma Myeloma Leuk.

2013; 13 Suppl 2:5307-9. Epub 2013 Dec. 7. doi: 10.1016/j.clml.2013.07.011. PubMed PMID: 24290217.

22. Choong M L, Pecquet C, Pendharkar V, Diaconu C C, Yong J W, Tai S J, Wang S F, Defour J P, Sangthongpitag K, Villeval J L, Vainchenker W, Constantinescu S N, Lee M A. Combination treatment for myeloproliferative neoplasms using JAK and pan-class I PI3K inhibitors. J Cell Mol Med. 2013; 17(11):1397-409. Epub 2013 Nov. 21. doi: 10.1111/jcmm.12156. PubMed PMID: 24251790; PMCID: PMC4117552.

23. Fiskus W, Verstovsek S, Manshouri T, Smith J E, Peth K, Abhyankar S, McGuirk J, Bhalla K N. Dual PI3K/AKT/mTOR inhibitor BEZ235 synergistically enhances the activity of JAK2 inhibitor against cultured and primary human myeloproliferative neoplasm cells. Mol Cancer Ther. 2013; 12(5):577-88. Epub 2013/03/01. doi: 10.1158/1535-7163.MCT-12-0862. PubMed PMID: 23445613.

24. Mishra R K, Wei C, Hresko R C, Bajpai R, Heitmeier M, Matulis S M, Nooka A K, Rosen S T, Hruz P W, Schiltz G E, Shanmugam M. In Silico Modeling-based Identification of Glucose Transporter 4 (GLUT4)-selective Inhibitors for Cancer Therapy. J Biol Chem. 2015; 290 (23):14441-53. Epub 2015 Apr. 8. doi: 10.1074/jbc.M114.628826. PubMed PMID: 25847249; PMCID: PMC4505511.

25. Chen V B, Arendall W B, 3rd, Headd J J, Keedy D A, Immormino R M, Kapral G J, Murray L W, Richardson J S, Richardson D C. MolProbity: all-atom structure validation for macromolecular crystallography. Acta Crystallogr D Biol Crystallogr. 2010; 66(Pt 1):12-21. Epub 2010 Jan. 9. doi: 10.1107/S0907444909042073. PubMed PMID: 20057044; PMCID: PMC2803126.

26. Schulz-Gasch T, Stahl M. Binding site characteristics in structure-based virtual screening: evaluation of current docking tools. J Mol Model. 2003; 9(1):47-57. Epub 2003 Mar. 15. doi: 10.1007/s00894-002-0112-y. PubMed PMID: 12638011.

27. Sherman W, Day T, Jacobson M P, Friesner R A, Farid R. Novel procedure for modeling ligand/receptor induced fit effects. J Med Chem. 2006; 49(2):534-53. Epub 2006 Jan. 20. doi: 10.1021/jm050540c. PubMed PMID: 16420040.

28. Ji P, Jayapal S R, Lodish H F. Enucleation of cultured mouse fetal erythroblasts requires Rac GTPases and mDia2. Nat Cell Biol. 2008; 10(3):314-21. Epub 2008 Feb. 12. doi: 10.1038/ncb1693. PubMed PMID: 18264091.

29. Isakoff S J, Cardozo T, Andreev J, Li Z, Ferguson K M, Abagyan R, Lemmon M A, Aronheim A, Skolnik E Y. Identification and analysis of P H domain-containing targets of phosphatidylinositol 3-kinase using a novel in vivo assay in yeast. EMBO J. 1998; 17(18):5374-87. Epub 1998 Sep. 16. doi: 10.1093/emboj/17.18.5374. PubMed PMID: 9736615; PMCID: PMC1170863.

30. Yilmaz O H, Valdez R, Theisen B K, Guo W, Ferguson D O, Wu H, Morrison S J. Pten dependence distinguishes haematopoietic stem cells from leukaemia-initiating cells. Nature. 2006; 441(7092):475-82. Epub 2006 Apr. 7. doi: 10.1038/nature04703. PubMed PMID: 16598206.

31. Wang Y, Chen X, Lian L, Tang T, Stalker T J, Sasaki T, Kanaho Y, Brass L F, Choi J K, Hartwig J H, Abrams C S. Loss of PIP5KIbeta demonstrates that PIP5KI isoform-specific PIP2 synthesis is required for IP3 formation. Proc Natl Acad Sci USA. 2008; 105(37):14064-9. Epub 2008 Sep. 6. doi: 10.1073/pnas.0804139105. PubMed PMID: 18772378; PMCID: PMC2544579.

32. Wang Y, Litvinov R I, Chen X, Bach T L, Lian L, Petrich B G, Monkley S J, Kanaho Y, Critchley D R, Sasaki T, Bimbaum M J, Weisel J W, Hartwig J, Abrams C S. Loss of PIPSKIgamma, unlike other PIP5KI isoforms, impairs the integrity of the membrane cytoskeleton in murine megakaryocytes. J Clin Invest. 2008; 118(2):812-9. Epub 2008 Jan. 12. doi: 10.1172/JCI34239. PubMed PMID: 18188447; PMCID: PMC2176194.

33. Caroni P. New EMBO members' review: actin cytoskeleton regulation through modulation of PI(4,5)P(2) rafts. EMBO J. 2001; 20(16):4332-6. Epub 2001 Aug. 14. doi: 10.1093/emboj/20.16.4332. PubMed PMID: 11500359; PMCID: PMC125564.

34. McLaughlin S, Murray D. Plasma membrane phosphoinositide organization by protein electrostatics. Nature. 2005; 438(7068):605-11. Epub 2005 Dec. 2. doi: 10.1038/nature04398. PubMed PMID: 16319880.

35. Liepina I, Czaplewski C, Janmey P, Liwo A. Molecular dynamics study of a gelsolin-derived peptide binding to a lipid bilayer containing phosphatidylinositol 4,5-bisphosphate. Biopolymers. 2003; 71(1):49-70. Epub 2003 Apr. 25. doi: 10.1002/bip.10375. PubMed PMID: 12712500.

36. Laux T, Fukami K, Thelen M, Golub T, Frey D, Caroni P. GAP43, MARCKS, and CAP23 modulate PI(4,5)P(2) at plasmalemmal rafts, and regulate cell cortex actin dynamics through a common mechanism. J Cell Biol. 2000; 149(7):1455-72. Epub 2000 Jun. 28. PubMed PMID: 10871285; PMCID: PMC2175130.

37. Lemmon M A. Membrane recognition by phospholipid-binding domains. Nat Rev Mol Cell Biol. 2008; 9(2):99-111. Epub 2008 Jan. 25. doi: 10.1038/nrm2328. PubMed PMID: 18216767.

38. Sheetz M P. Cell control by membrane-cytoskeleton adhesion. Nat Rev Mol Cell Biol. 2001; 2(5):392-6. Epub 2001 May 2. doi: 10.1038/35073095. PubMed PMID: 11331914.

39. Hamaguchi N, Ihara S, Ohdaira T, Nagano H, Iwamatsu A, Tachikawa H, Fukui Y. Pleckstrin-2 selectively interacts with phosphatidylinositol 3-kinase lipid products and regulates actin organization and cell spreading. Biochem Biophys Res Commun. 2007; 361(2):270-5. Epub 2007 Jul. 31. doi: 10.1016/j.bbrc.2007.06.132. PubMed PMID: 17658464.

40. Kurokawa T, Takasuga S, Sakata S, Yamaguchi S, Horie S, Homma K J, Sasaki T, Okamura Y. 3' Phosphatase activity toward phosphatidylinositol 3,4-bisphosphate [PI (3,4)P2] by voltage-sensing phosphatase (VSP). Proc Natl Acad Sci USA. 2012; 109(25):10089-94. Epub 2012 MAy 31. doi: 10.1073/pnas.1203799109. PubMed PMID: 22645351; PMCID: PMC3382541.

41. Lemmon M A, Ferguson K M, Abrams C S. Pleckstrin homology domains and the cytoskeleton. FEBS Lett. 2002; 513(1):71-6. Epub 2002 Mar. 26. PubMed PMID: 11911883.

42. Fischer B, Luthy K, Paesmans J, De Koninck C, Maes I, Swerts J, Kuenen S, Uytterhoeven V, Verstreken P, Versees W. Skywalker-TBC1D24 has a lipid-binding pocket mutated in epilepsy and required for synaptic function. Nat Struct Mol Biol. 2016; 23(11):965-73. Epub 2016 Nov. 1. doi: 10.1038/nsmb.3297. PubMed PMID: 27669036.

43. Lemmon M A, Ferguson K M, O'Brien R, Sigler P B, Schlessinger J. Specific and high-affinity binding of inositol phosphates to an isolated pleckstrin homology domain. Proc Natl Acad Sci USA. 1995; 92(23):10472-6. Epub 1995 Nov. 7. PubMed PMID: 7479822; PMCID: PMC40633.

44. Yu J W, Mendrola J M, Audhya A, Singh S, Keleti D, DeWald D B, Murray D, Emr S D, Lemmon M A. Genome-wide analysis of membrane targeting by *S. cerevisiae* pleckstrin homology domains. Mol Cell. 2004; 13(5):677-88. Epub 2004 Mar. 17. PubMed PMID: 15023338.
45. Ma A D, Abrams C S. Pleckstrin induces cytoskeletal reorganization via a Rac-dependent pathway. J Biol Chem. 1999; 274(40):28730-5. Epub 1999 Sep. 25. PubMed PMID: 10497244.
46. Hresko R C, Murata H, Mueckler M. Phosphoinositide-dependent kinase-2 is a distinct protein kinase enriched in a novel cytoskeletal fraction associated with adipocyte plasma membranes. J Biol Chem. 2003; 278(24):21615-22. Epub 2003/04/19. doi: 10.1074/jbc.M302937200. PubMed PMID: 12682057.
47. Bondeson D P, Smith B E, Burslem G M, Buhimschi A D, Hines J, Jaime-Figueroa S, Wang J, Hamman B D, Ishchenko A, Crews C M. Lessons in PROTAC Design from Selective Degradation with a Promiscuous Warhead. Cell Chem Biol. 2018; 25(1):78-87 e5. Epub 2017 Nov. 14. doi: 10.1016/j.chembiol.2017.09.010. PubMed PMID: 29129718; PMCID: PMC5777153.
48. Neklesa T K, Winkler J D, Crews C M. Targeted protein degradation by PROTACs. Pharmacology & therapeutics. 2017; 174:138-44. Epub 2017 Feb. 23. doi: 10.1016/j.pharmthera.2017.02.027. PubMed PMID: 28223226.
49. Lonsdale R, Ward R A. Structure-based design of targeted covalent inhibitors. Chemical Society reviews. 2018; 47(11):3816-30. Epub 2018 Apr. 6. doi: 10.1039/c7cs00220c. PubMed PMID: 29620097.
50. Butler K V, Ma A, Yu W, Li F, Tempel W, Babault N, Pittella-Silva F, Shao J, Wang J, Luo M, Vedadi M, Brown P J, Arrowsmith C H, Jin J. Structure-Based Design of a Covalent Inhibitor of the SET Domain-Containing Protein 8 (SETD8) Lysine Methyltransferase. J Med Chem. 2016; 59(21):9881-9. Epub 2016 Nov. 3. doi: 10.1021/acs.jmedchem.6b01244. PubMed PMID: 27804297; PMCID: PMC5148670.
51. Zhou L P, Yang L H, Tilton S, Wang J L. Development of a high throughput equilibrium solubility assay using miniaturized shake-flask method in early drug discovery. J Pharm Sci-Us. 2007; 96(11):3052-71. doi: Doi 10.1002/Jps.20913. PubMed PMID: WOS:000250618700018.
52. Pikman Y, Lee B H, Mercher T, McDowell E, Ebert B L, Gozo M, Cuker A, Wernig G, Moore S, Galinsky I, DeAngelo D J, Clark J J, Lee S J, Golub T R, Wadleigh M, Gilliland D G, Levine R L. MPLW515L is a novel somatic activating mutation in myelofibrosis with myeloid metaplasia. PLoS Med. 2006; 3(7):e270. Epub 2006/07/13. doi: 10.1371/journal.pmed.0030270. PubMed PMID: 16834459; PMCID: PMC1502153.
53. Wen Q J, Yang Q, Goldenson B, Malinge S, Lasho T, Schneider R K, Breyfogle L J, Schultz R, Gilles L, Koppikar P, Abdel-Wahab O, Pardanani A, Stein B, Gurbuxani S, Mullally A, Levine R L, Tefferi A, Crispino J D. Targeting megakaryocytic-induced fibrosis in myeloproliferative neoplasms by AURKA inhibition. Nat Med. 2015; 21(12):1473-80. Epub 2015 Nov. 17. doi: 10.1038/nm.3995. PubMed PMID: 26569382; PMCID: PMC4674320.
54. Kleppe M, Kwak M, Koppikar P, Riester M, Keller M, Bastian L, Hricik T, Bhagwat N, McKenney A S, Papalexi E, Abdel-Wahab O, Rampal R, Marubayashi S, Chen J J, Romanet V, Fridman J S, Bromberg J, Teruya-Feldstein J, Murakami M, Radimerski T, Michor F, Fan R, Levine R L. JAK-STAT pathway activation in malignant and non-malignant cells contributes to MPN pathogenesis and therapeutic response. Cancer Discov. 2015; 5(3):316-31. Epub 2015 Jan. 13. doi: 10.1158/2159-8290.CD-14-0736. PubMed PMID: 25572172; PMCID: PMC4355105.

Example 2—Further Testing and Development of Plek2 Inhibitors

Figure 15A:
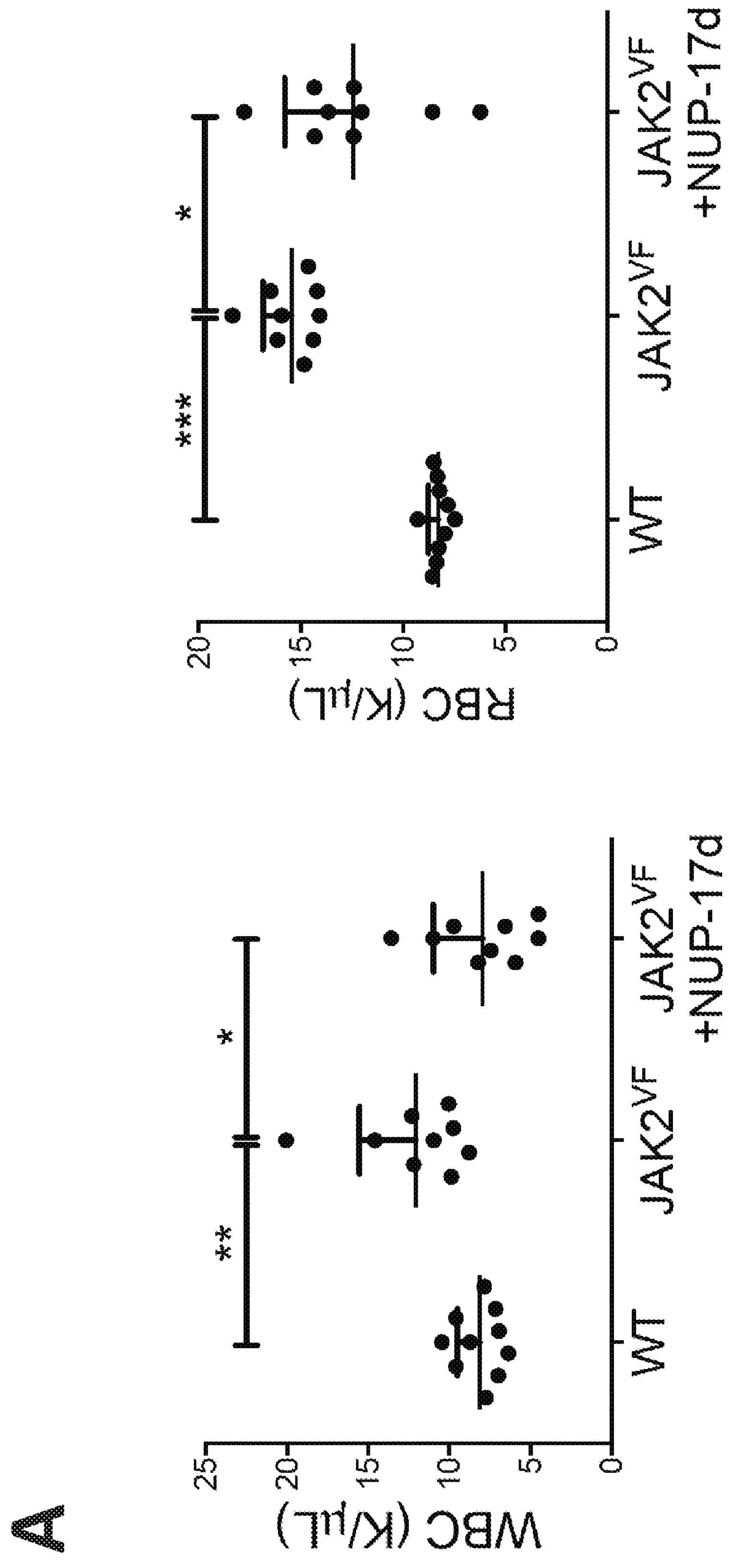
FIG. 15A and FIG. 15B. Compound NUP-17d ameliorates myeloproliferation and thrombosis in $JAK2^{V617F}$ knockin mice.
Figure 15B:
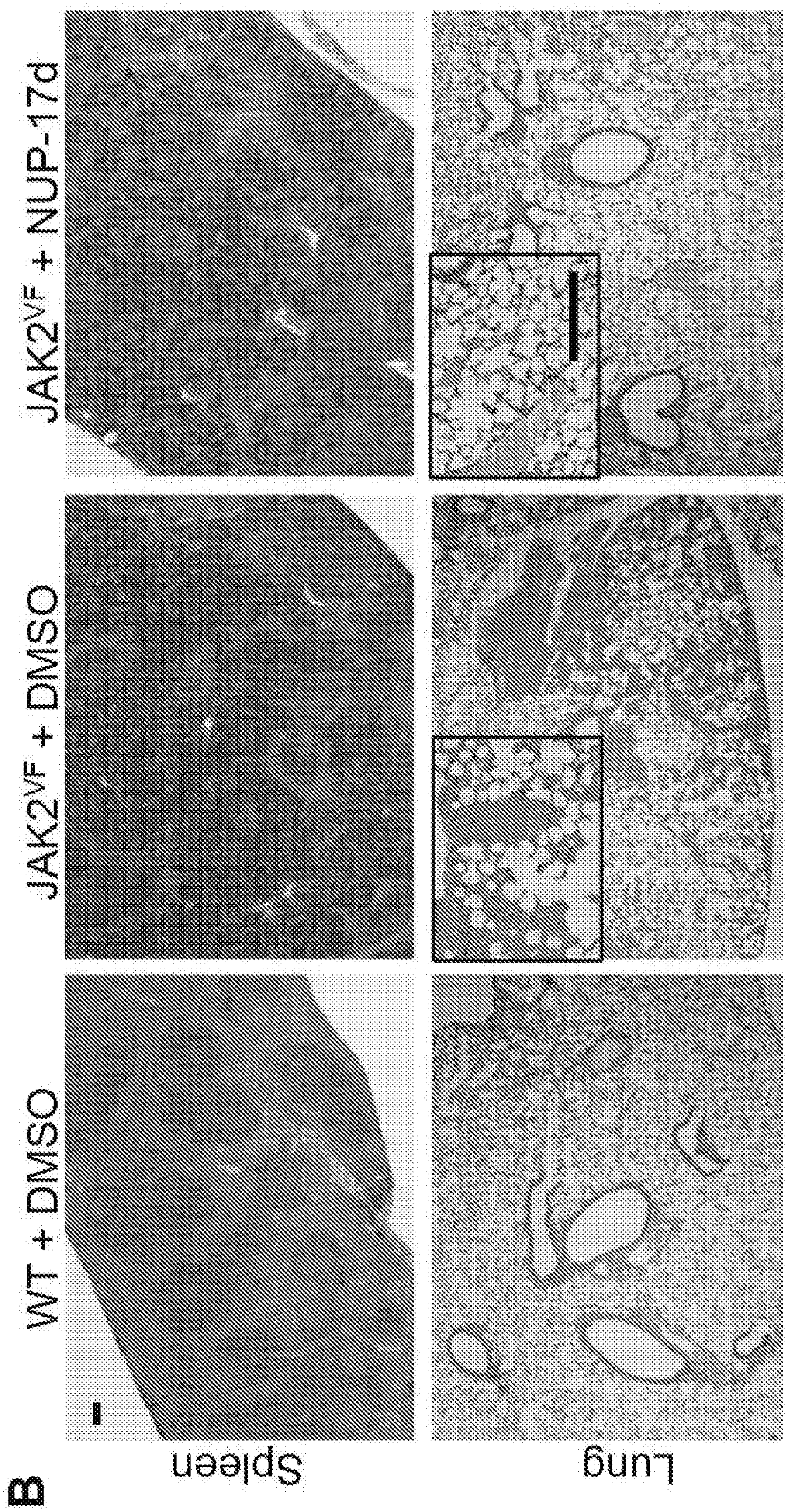

We tested the effects of Plek2 inhibitors in the $JAK2^{V617F}$ knockin MPN mouse model. (See FIGS. 15A and 15B). The same dosage and dosing schedule of NUP-17d (25 mg/kg, once every two days) were applied to $JAK2^{V617F}$ knockin mice as those applied to the Epo model. We have treated the mice for one month. As expected, chronic treatment of NUP-17d largely normalized WBC count and significantly reduced the red blood cell count. (See FIG. 15A). The spleen size and extramedullary erythropoiesis were markedly reduced. Vascular occlusions in the lungs were also dramatically ameliorated. (See FIG. 15B). The treated mice also showed no gross side effects with the treatment. These data provide a proof-of-concept that Plek2 inhibitors are effective in treating myeloproliferation.

Figure 16:
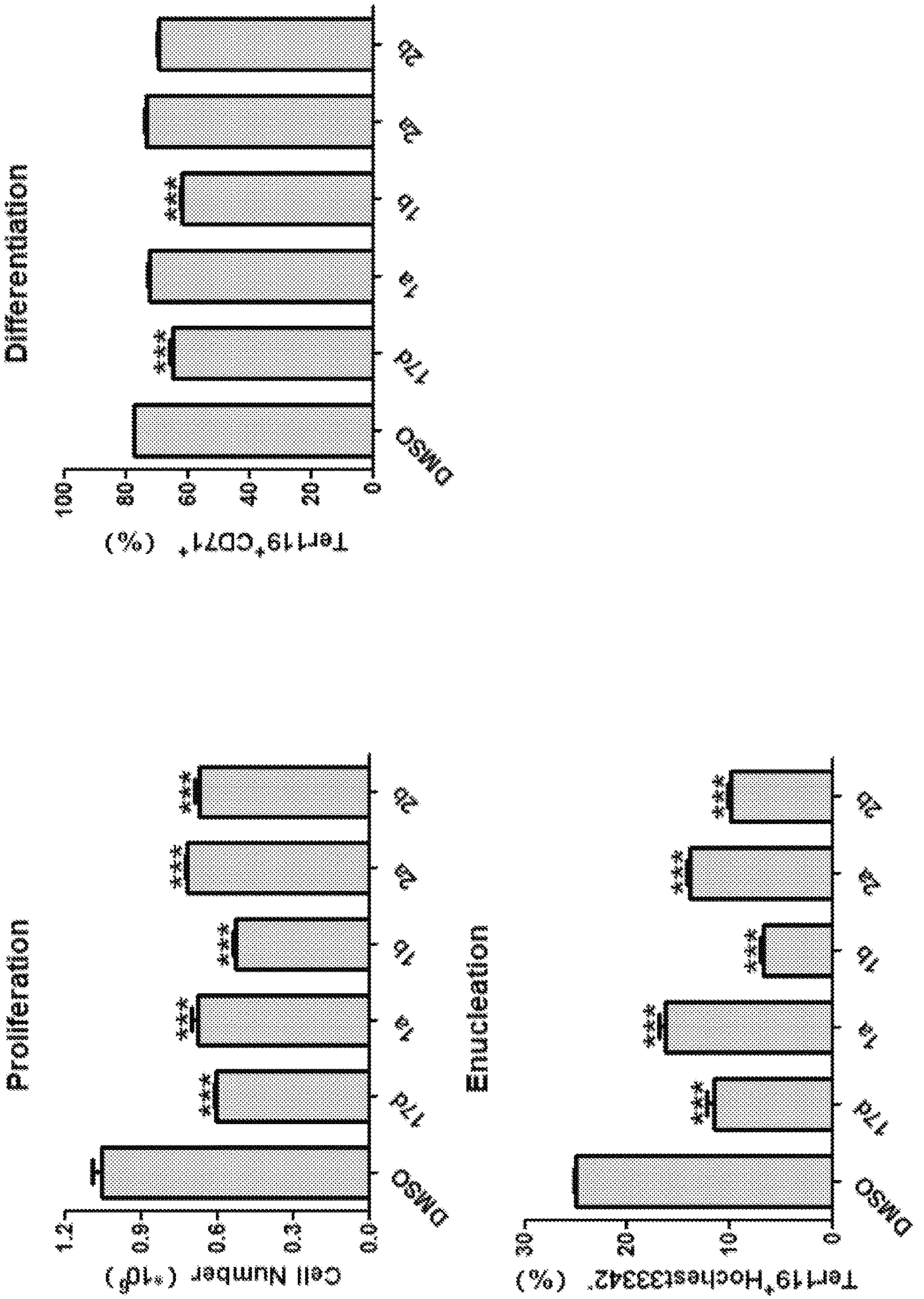
FIG. 16. Cell proliferation, differentiation, and enucleation assays of enantiomers obtained from NUP-17d racemate. Concentrations used: 10 uM. The cells used were Ter119 negative bone marrow progenitor cells cultured in erythropoietin (Epo) containing medium for 2 days.

We also assessed cell proliferation, differentiation, and enucleation assays of enantiomers obtained from NUP-17d racemate. (See FIG. 16). Enantiomer NUP-17d-1b showed the best bioactivities.

Figure 17:
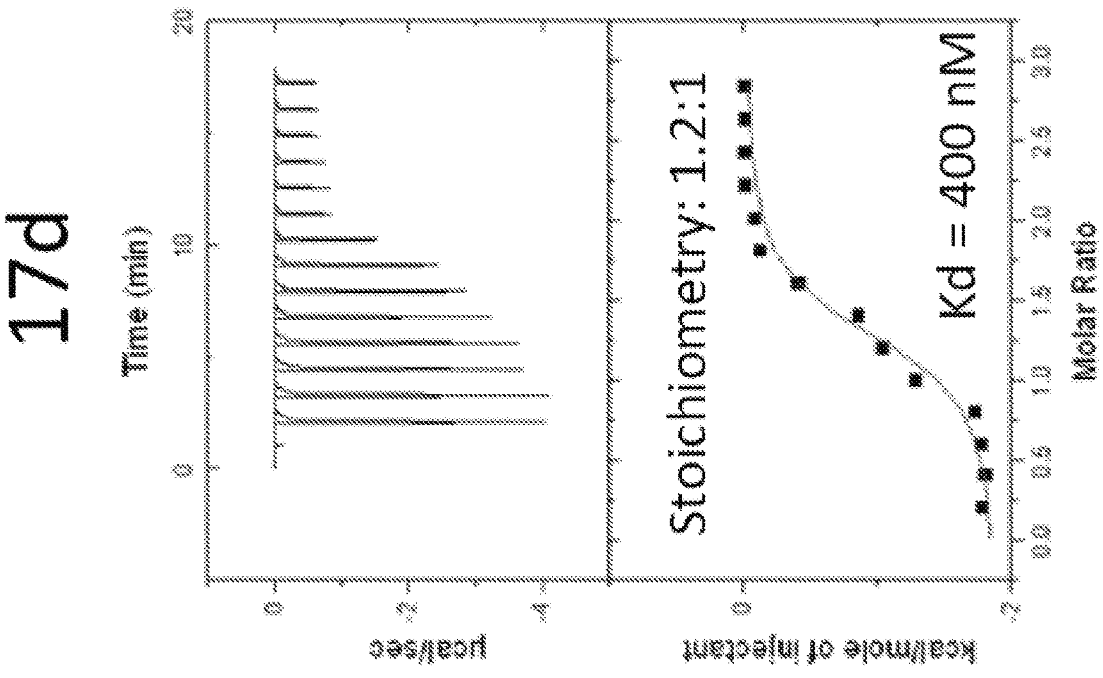
FIG. 17. Isothermal titration calorimetry (ITC) experiments of NUP-17d and its enantiomers. -17-d: delta H=−1.9 kcal/mol delta S=+22.9 cal/molK; -17-1b: delta H=−2.2 kcal/mol delta S=+22.8 cal/molK; -17-2b: delta H=−1.5 kcal/mol delta S=+24.3 cal/molK; -17-1a: delta H=−5.3 kcal/mol delta S=+7.3 cal/molK; and -17-2a: delta H=−4.2 kcal/mol delta S=+13.9 cal/molK.
Figure 17:
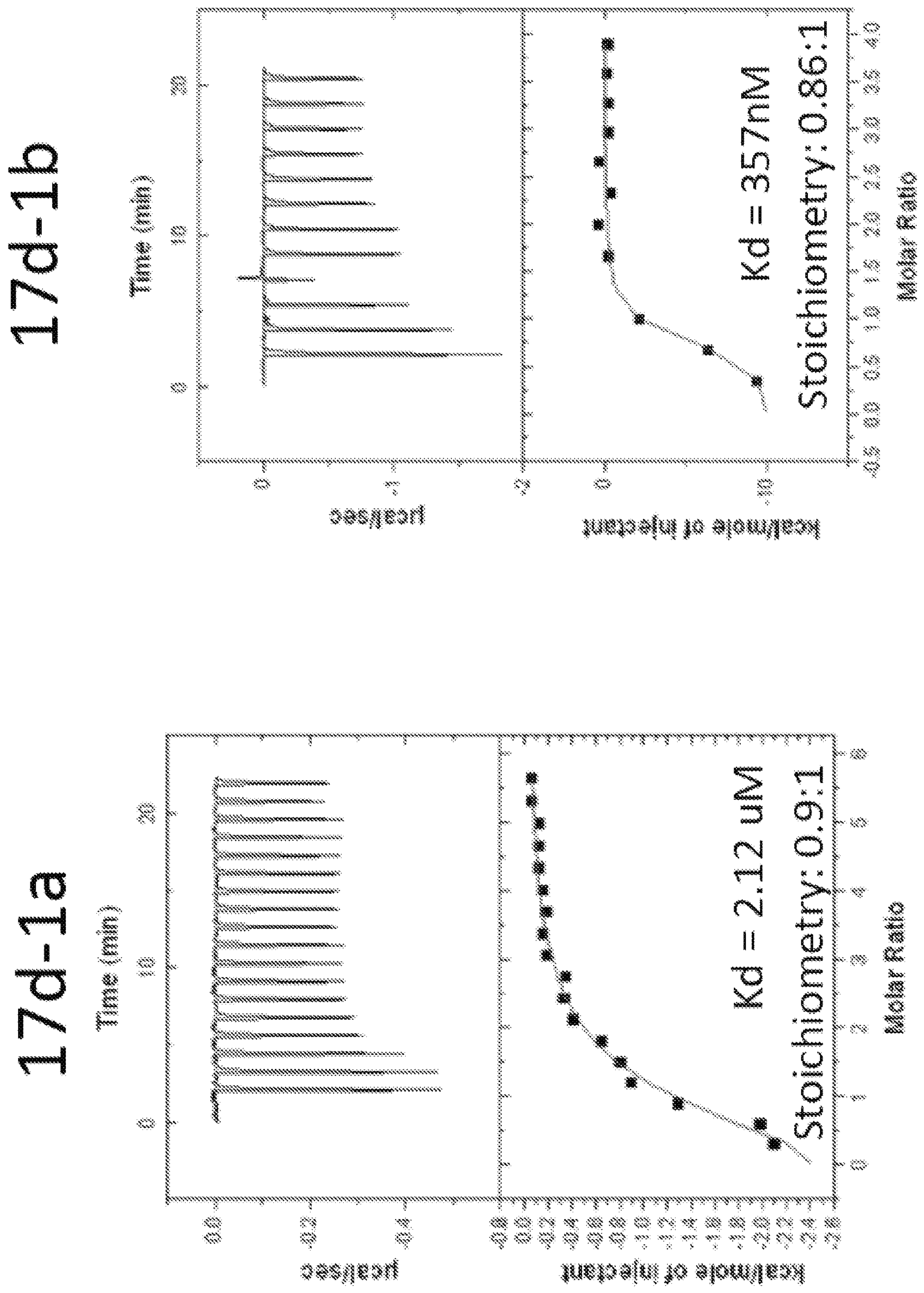
Figure 17:
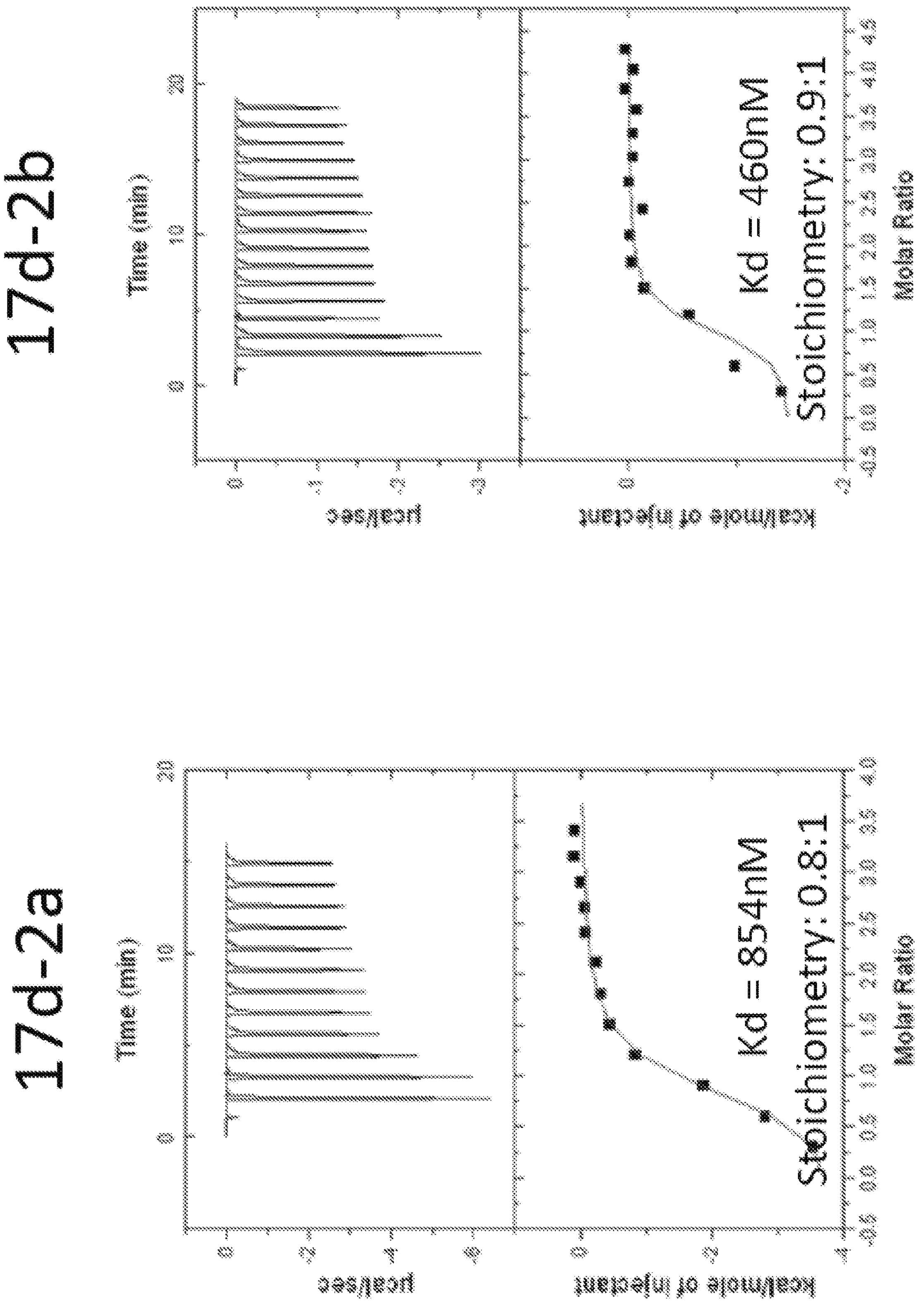

We also performed isothermal titration calorimetry (ITC) experiments of NUP-17d and its enantiomers. (See FIG. 17). NUP-17d-1b was observed to have the best Kd in these experiments.

Figure 18:
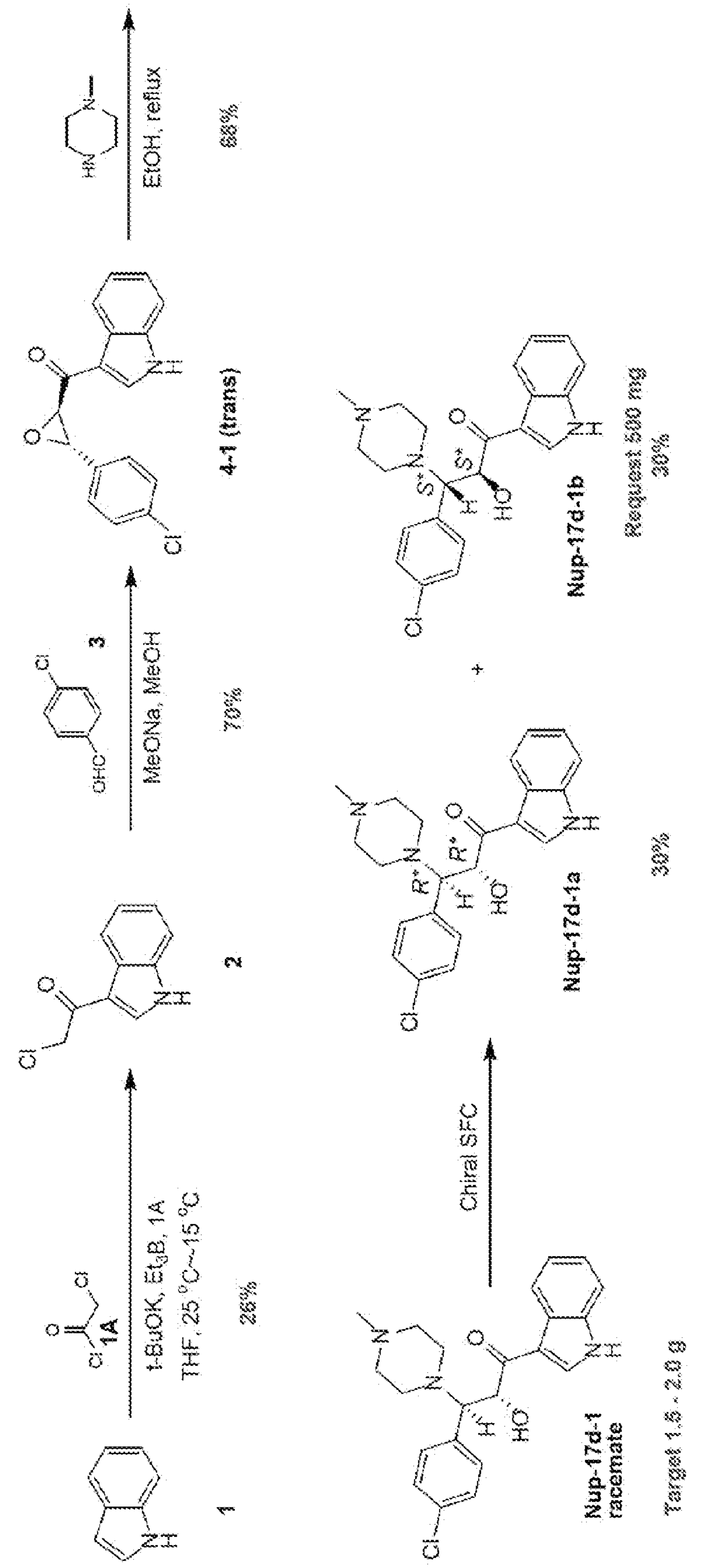
FIG. 18. Steps to scale up NUP-17d-1b for further development of additional compounds.
Figure 19:
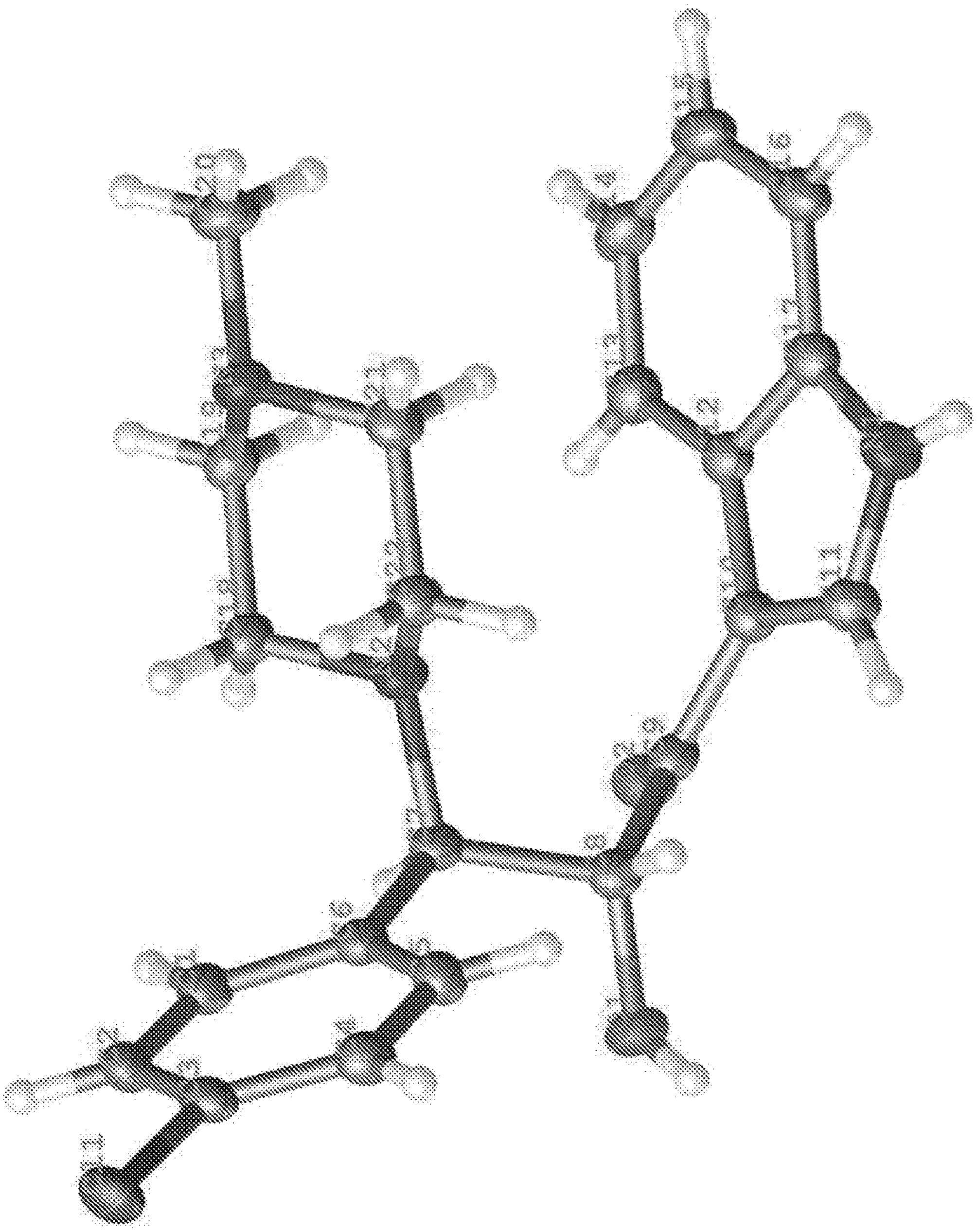
FIG. 19. Oak Ridge Thermal Ellipsoid Plot (ORTEP) of crystal structure of NUP-17d-1b as determined by X-ray diffraction.

In order to scale up NUP-17d-1b for further development of more potent compounds, we developed a scheme as illustrated in FIG. 18.

We crystallized NUP-17d-1b. The crystal was a colorless prism with the following dimensions: 0.20×0.04×0.04 mm3. The symmetry of the crystal structure was assigned the orthorhombic space group P212121 with the following parameters: a=5.98290(10) Å, b=15.47800(10) Å, c=20.8811(2) Å, α=90°, β=90°, γ=90°, V=1933.66(4) Å3, Z=4, Dc=1.367 Mg/m3, F(000)=840.0, μ(Cu Kα)=1.936 mm-1, and T=100.0 (2) K.

Example 3—Loss of Pleckstrin-2 Reverts Lethality and Vascular Occlusions in JAK2V617F-Positive Myeloproliferative Neoplasms Reference is made to Zhao et al., "Loss of pleckstrin-2 reverts lethality and vascular occlusions in JAK2V617F-positive myeloproliferative neoplasms, J. Clin. Invest., Nov. 20, 2017, the content of which is incorporated herein by reference in its entirety.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/ or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A compound having the following formula or a salt, hydrate, or solvate thereof:

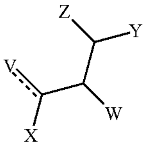

wherein:

V is hydrogen, hydroxyl, or keto;

W is hydrogen, hydroxyl, or alkyoxy;

X is 1H-indol-3-yl, N-alkyl-indol-3-yl, 1H-indazol-3-yl, or N-alkyl-indazol-3-yl optionally substituted at one or more positions with a substituent selected from alkyl, cycloalkyl, cycloheteroalkyl, alkoxy, halo, haloalkyl, amino, and cyano;

Y is a 5-membered or 6-membered carbocycle or heterocycle which optionally is saturated or unsaturated at one or more bonds and optionally is substituted at one or more positions with a substituent selected from alkyl, cycloalkyl, cycloheteroalkyl, alkoxy, halo, haloalkyl, amino, and cyano; and Z is selected from —$NR^3R^4$ or —$OR^5$, wherein $R^3$ and $R^4$ together form a 5-membered heterocycle which is saturated or unsaturated at one or more bonds and optionally is substituted at one or more positions with a substituent selected from alkyl, cycloalkyl, cycloheteroalkyl, alkoxy, halo, haloalkyl, hydroxyalkyl, amino, and cyano; $R^5$ is selected from hydrogen, alkyl, and cycloalkyl.

2. The compound of claim 1, wherein V is keto and W is hydroxyl.

3. The compound of claim 1 having a formula selected from:

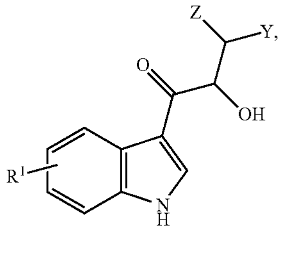

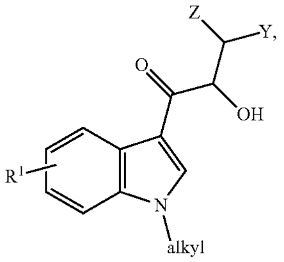

-continued

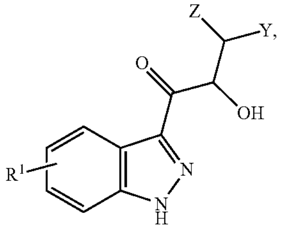

and

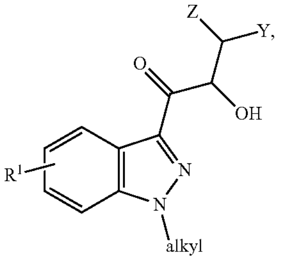

wherein $R^1$ is selected from alkyl, cycloalkyl, cycloheteroalkyl, alkoxy, halo, haloalkyl, amino, and cyano.

4. The compound of claim 1, wherein X is selected from:

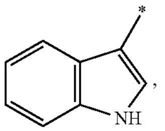

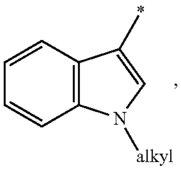

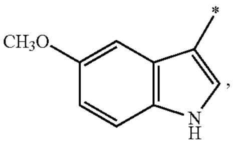

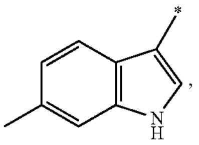

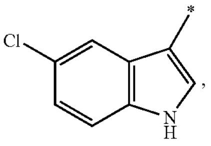

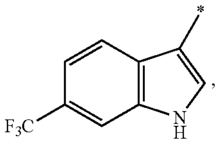

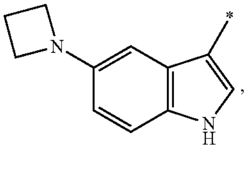

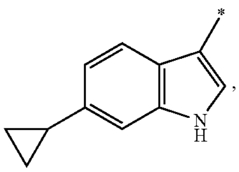

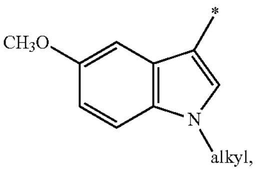

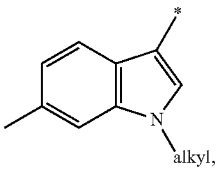

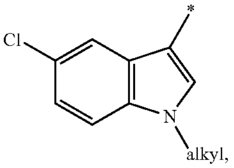

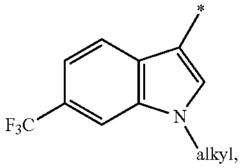

-continued

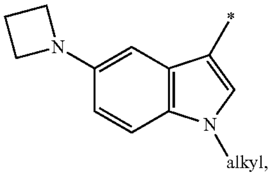
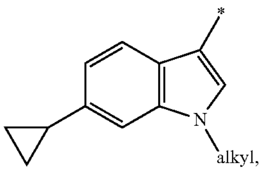
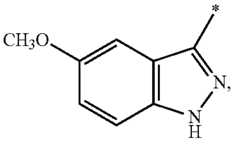
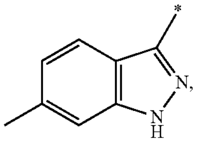
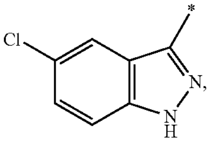
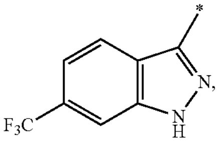
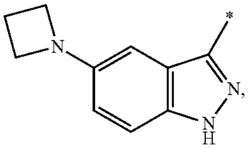
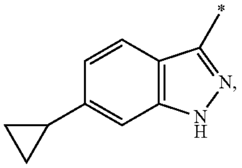
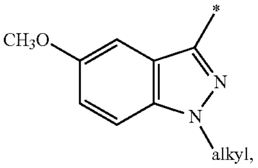
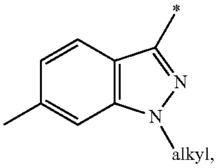
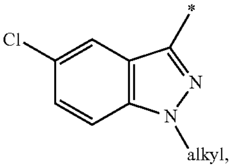
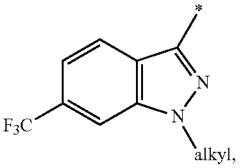
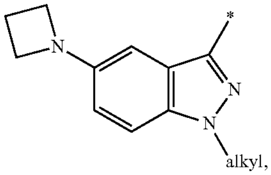
and
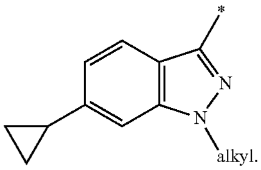

5. The compound of claim 1, wherein Y is selected from phenyl, pyridinyl, and thiophenyl, optionally substituted at one or more positions with a substituent selected from alkyl, cycloalkyl, cycloheteroalkyl, alkoxy, halo, haloalkyl, aryl, amino, and cyano.

6. The compound of claim 1, wherein Y is selected from:

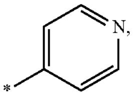
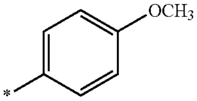
,
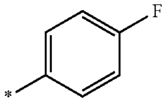
,

-continued

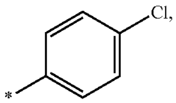
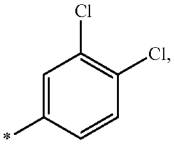
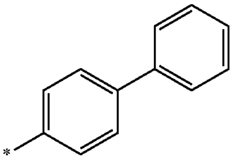
, and
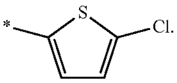

7. The compound of claim 1, wherein Z is —$NR^3R^4$ and $R^3$ and $R^4$ together form a 5-membered heterocycle which is saturated or unsaturated at one or more bonds and optionally is substituted at one or more positions with a substituent selected from alkyl, cycloalkyl, cycloheteroalkyl, alkoxy, halo, haloalkyl, amino, and cyano.

8. The compound of claim 1, wherein Z is —$OR^5$ and $R^5$ is selected from hydrogen, alkyl, and cycloalkyl.

9. The compound of claim 1, wherein Z is selected from:

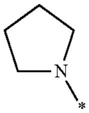
, and
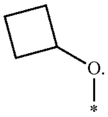

10. The compound of claim 1, having a formula of:

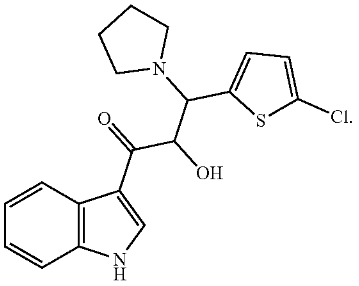 [SMILES: O=C(c1c[nH]c2ccccc12)C(O)C(c1ccc(Cl)s1)N1CCCC1]

11. A conjugate comprising the compound of claim 1 further conjugated to an E3 ligase recruiter of a formula:

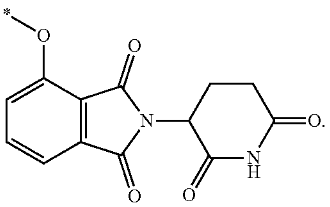 [SMILES: *Oc1cccc2c1C(=O)N(C1CCC(=O)NC1=O)C2=O]

12. The conjugate of claim 11, wherein the conjugation is via a linker, optionally wherein the linker comprises a moiety having a formula —$(OCH_2CH_2)_n$—NHC(O)— and n is 1-6.

13. A pharmaceutical composition comprising the compound of claim 1 and a suitable pharmaceutical carrier.

14. A method for treating a cell proliferative disease or disorder in a subject in need thereof, the method comprising administering to the subject the pharmaceutical composition of claim 13, wherein the cell proliferative disease or disorder is a Philadelphia chromosome (Ph)-negative myeloproliferative neoplasm (MPN) or acute myeloid leukemia (AML).

* * * * *